United States Patent
Matsumoto et al.

(10) Patent No.: US 8,916,549 B2
(45) Date of Patent: Dec. 23, 2014

(54) THIENOOXAZEPINE DERIVATIVE

(75) Inventors: Takahiro Matsumoto, Kanagawa (JP); Izumi Nomura, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 336 days.

(21) Appl. No.: 13/388,362

(22) PCT Filed: Aug. 3, 2010

(86) PCT No.: PCT/JP2010/063120
§ 371 (c)(1),
(2), (4) Date: Apr. 16, 2012

(87) PCT Pub. No.: WO2011/016459
PCT Pub. Date: Feb. 10, 2011

(65) Prior Publication Data
US 2012/0196848 A1 Aug. 2, 2012

(30) Foreign Application Priority Data
Aug. 4, 2009 (JP) .................. 2009-181360

(51) Int. Cl.
*A61K 31/553* (2006.01)
*C07D 498/04* (2006.01)

(52) U.S. Cl.
CPC ............ *C07D 498/04* (2013.01); *A61K 31/553* (2013.01)
USPC ....................................... 514/211.1; 540/552

(58) Field of Classification Search
USPC ....................................... 514/211.1; 540/552
See application file for complete search history.

(56) References Cited

U.S. PATENT DOCUMENTS

| | | | |
|---|---|---|---|
| 7,625,887 B2 | 12/2009 | Itoh et al. | |
| 2006/0199795 A1 | 9/2006 | Itoh et al. | |
| 2009/0131402 A1 | 5/2009 | Shirai et al. | |
| 2009/0318412 A1 | 12/2009 | Matsumoto et al. | |
| 2010/0004249 A1 | 1/2010 | Matsumoto et al. | |
| 2010/0087418 A1 | 4/2010 | Shirai et al. | |
| 2010/0266504 A1 | 10/2010 | Matsumoto et al. | |
| 2010/0286120 A1 | 11/2010 | Matsumoto et al. | |

FOREIGN PATENT DOCUMENTS

| | | |
|---|---|---|
| JP | 2006-056881 | 3/2006 |
| WO | 2004/067008 | 8/2004 |
| WO | 2007/132841 | 11/2007 |
| WO | 2008/007661 | 1/2008 |
| WO | 2008/007664 | 1/2008 |
| WO | 2008/108445 | 9/2008 |
| WO | 2009/063991 | 5/2009 |
| WO | 2009/063992 | 5/2009 |
| WO | 2009-063993 | 5/2009 |
| WO | 2009/063993 | 5/2009 |

OTHER PUBLICATIONS

International Search Report issued Nov. 2, 2010 in International (PCT) Application No. PCT/JP2010/063120.

*Primary Examiner* — Brenda Coleman
(74) *Attorney, Agent, or Firm* — Wenderoth, Lind & Ponack, L.L.P.

(57) ABSTRACT

Provision of a compound having a serotonin 5-HT$_{2C}$ receptor activating action.
A compound represented by the formula (I):

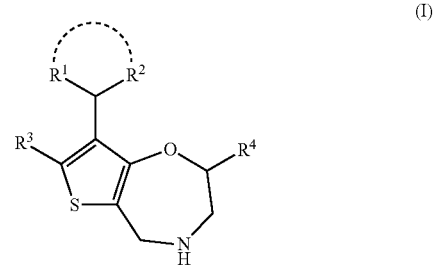

wherein each symbol is as described in the description, or a salt thereof.

15 Claims, No Drawings

THIENOOXAZEPINE DERIVATIVE

This application is a U.S. national stage of International Application No. PCT/JP2010/063120 filed Aug. 3, 2010.

TECHNICAL FIELD

The present invention relates to a thienooxazepine derivative having an excellent serotonin 5-HT$_{2C}$ receptor activating action, and useful as a therapeutic or prophylactic agent and the like for a lower urinary tract symptom, obesity and/or organ prolapse and the like.

BACKGROUND OF THE INVENTION

Serotonin 5-HT$_{2C}$ receptor is one of the receptors of the biological transmitter serotonin, which is distributed mainly in the central nervous system and controls many physiological functions in vivo. A representative example is the control of appetite. It has been demonstrated in a study using rodents that stimulation of the central serotonin 5-HT$_{2C}$ receptor decreases eating behavior, resulting in decreased body weight. It has also been reported that, in human as well, administration of a serotonin 5-HT$_{2C}$ receptor activator suppresses appetite and decreases body weight (see non-patent document 1). In addition, it has been demonstrated in a rat test using a serotonin 5-HT$_{2C}$ receptor activator that stimulation of the central serotonin 5-HT$_{2C}$ receptor suppresses depression-related behaviors (see non-patent document 2), and has also been reported to be effective for many central nervous diseases such as anxiety etc. (see non-patent document 3). The serotonin 5-HT$_{2C}$ receptor is also highly expressed in the parasympathetic nucleus and motorial nerve cell bodies in the sacral spinal cord, and is considered to control the peripheral nervous functions (see non-patent document 4). It has been reported that when a serotonin 5-HT$_{2C}$ receptor activator is administered to rats, penile erection is induced (see non-patent document 5), and urethral resistance is increased (see patent document 1); all these actions are attributed to stimulation of the serotonin 5-HT$_{2C}$ receptor in the sacral spinal cord. For serotonin 5-HT$_{2C}$ receptor activators, many clinical applications are likely, with particular expectations for anti-obesity drugs, anti-depressants, anti-anxiety drugs, therapeutic drugs for male erectile dysfunction, and therapeutic drugs for stress urinary incontinence and the like.

In addition, a serotonin 5-HT$_{2C}$ receptor activator is useful as a drug for the prophylaxis or treatment of diseases caused by prolapse of organ from the normal position due to weakened pelvic floor muscles, for example, organ prolapse (e.g., pelvic organ prolapse, genital prolapse, uterine prolapse, bladder prolapse, rectal prolapse, urethral prolapse, urethral hypermobility, enteroceles, rectoceles, cystoceles, laceration of perineal body, pelvic floor hernia etc.) (see, for example, patent document 2).

"Pelvic organ prolapse" is a disease wherein the anterior wall of the vagina, the posterior wall of the vagina, the uterus, the vaginal stump after hysterectomy or the urinary bladder descends and protrudes beyond the vaginal orifice, and further, rectal prolapse is characterized by the symptom of descent and protrusion of the rectum from the anal area. In addition, cystoceles and enteroceles are diseases wherein bladder and small intestine descend and protrude beyond the vaginal orifice (see, for example, non-patent document 6 and non-patent document 7). Such descent becomes conspicuous when abdominal pressure rises transiently as a result of straining or bearing a heavy load and the like. These diseases are prevalent in females, with childbirth, aging, and obesity being known as risk factors, and one of suggested causes thereof is the weakening of the pelvic floor muscles, fascias and perivisceral connective tissue that support pelvic organs including the bladder and the like. The pelvic floor muscles are skeletal muscles that unite with the pelvis in a hammock-like way, serving constantly to maintain some contraction and support the organs in the pelvis from below. In pelvic organ prolapse, rectal prolapse, cystoceles and enteroceles, organ weights reportedly become unendurable because of the weakening of these pelvic floor muscles, resulting in the descent of the pelvic organs and the rectum (see, for example, non-patent document 6 and non-patent document 7); it is thought that when abdominal pressure rises particularly, the increased pressure becomes unendurable and the protrusion becomes more conspicuous. On the other hand, it has been reported that when abdominal pressure rises, the urinary bladder is compressed, reflex via the urinary bladder—spinal cord—pelvic floor muscles and the urethra causes the pelvic floor muscles and the urethral sphincter to contract to increase urethral internal pressure, whereby urinary incontinence is prevented (see, for example, non-patent document 8). Similarly, upon a rise in abdominal pressure, the pelvic floor muscles contract reflexly to prevent not only urinary incontinence, but also the descent of the pelvic organs including bladder and small intestine (see, for example, patent document 2). When there is a disorder in this reflex pathway or the pelvic floor muscles, sufficient contraction of the pelvic floor muscles cannot be obtained and support for the pelvic organs including bladder and small intestine becomes inadequate. Organ prolapse is a disease wherein the pelvic floor organs (urinary tract, bladder, uterus, small intestine, rectal and the like) and the like protrude from the vaginal orifice or rectal orifice to the outside due to the insufficient contractile strength of the pelvic floor muscles. Organ prolapse includes the forms of rectal prolapse, uterine prolapse, urethral prolapse, cystoceles, enteroceles and the like depending on the kind of the protruded organ.

Fused heterocyclic compounds having a serotonin 5-HT$_{2C}$ receptor activating action are known (see, for example, patent documents 3, 4, 12 and 13). In addition, it is also known that a compound bound to a serotonin 5-HT$_{2C}$ receptor is useful for the treatment of stress urinary incontinence and the like (see, for example, patent documents 5-9).

In addition, fused heterocyclic compounds of the benzodiazepine system, the pyridooxazepine system and the like are also known (see, for example, patent documents 10 and 11).

DOCUMENT LIST

Patent Documents patent document 1: WO04/096196
patent document 2: WO07/132,841
patent document 3: WO02/040457
patent document 4: WO08/108,445
patent document 5: WO02/083863
patent document 6: WO03/097636
patent document 7: WO04/000829
patent document 8: WO04/000830
patent document 9: WO02/008178
patent document 10: WO04/067008
patent document 11: JP-A-2006-056881
patent document 12: WO08/007,661
patent document 13: WO08/007,664

Non-Patent Documents non-patent document 1: Expert Opinion on Investigational Drugs, 2006, vol. 15, p. 257-266
non-patent document 2: J. Pharmacol. Exp. Ther., 1998, vol. 286, p. 913-924
non-patent document 3: Pharmacology Biochemistry Behavior, 2002, vol. 71, p. 533-554
non-patent document 4: Neuroscience, 1999, vol. 92, p. 1523-1537
non-patent document 5: Eur. J. Pharmacol., 2004, vol. 483, p. 37-43
non-patent document 6: Lancet, 2007, vol. 369, p. 1027-38
non-patent document 7: Europian Urology, 2007, vol. 51, p. 884-886
non-patent document 8: American Journal of Physiology Renal Physiology, 2004, vol. 287, p. F434-441

SUMMARY OF THE INVENTION

Problems to be Solved by the Invention

There is a demand on the development of a compound having a serotonin 5-$HT_{2C}$ receptor activating action, which is useful as an agent for the treatment or prophylaxis of lower urinary tract symptom, obesity and/or organ prolapse and the like, and has superior properties in terms of receptor selectivity, efficacy, duration of action, specificity, lower toxicity and the like.

The present invention aims to provide an agent for the prophylaxis or treatment of diseases such as a lower urinary tract symptom, obesity and/or organ prolapse and the like, comprising a thienooxazepine derivative having a serotonin 5-$HT_{2C}$ receptor activating action and the like, which has a chemical structure different from that of known compounds (including the aforementioned compounds).

Means of Solving the Problems

The present inventors have conducted intensive studies in an attempt to solve the aforementioned problems and found that a compound represented by the following formula (I) or a salt thereof has a superior serotonin 5-$HT_{2C}$ receptor activating action, and conducted further studies, which resulted in the completion of the present invention.

Accordingly, the present invention relates to
[1] a compound represented by the formula (I)

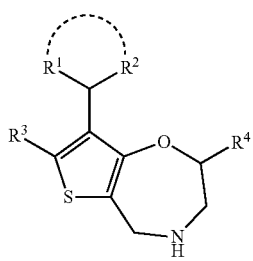

(I)

wherein
$R^1$ and $R^2$ are the same or different and each is a hydrogen atom, or a $C_{1-3}$ alkyl group optionally substituted by a halogen atom(s) (at least one of $R^1$ and $R^2$ is a $C_{1-3}$ alkyl group optionally substituted by halogen atom(s)), or $R^1$ and $R^2$ form, together with the adjacent carbon atom, (a) a $C_{3-4}$ cycloalkyl group optionally substituted by halogen atom(s), (b) a phenyl group substituted by substituent(s) selected from a halogen atom and a $C_{1-3}$ alkoxy group, or (c) a furyl group; and
$R^3$ and $R^4$ are the same or different and each is a hydrogen atom or a $C_{1-3}$ alkyl group,
or a salt thereof (hereinafter sometimes to be referred to as "compound (I)");

[2] the compound of the above-mentioned [1], wherein $R^1$ and $R^2$ are the same or different and each is a hydrogen atom, or a $C_{1-3}$ alkyl group optionally substituted by halogen atom(s) (at least one of $R^1$ and $R^2$ is a $C_{1-3}$ alkyl group optionally substituted by halogen atom(s)), or
$R^1$ and $R^2$ form, together with the adjacent carbon atom, a $C_{3-4}$ cycloalkyl group, or a phenyl group substituted by substituent(s) selected from a halogen atom and a $C_{1-3}$ alkoxy group; and
$R^3$ and $R^4$ are the same or different and each is a hydrogen atom or a $C_{1-3}$ alkyl group,
or a salt thereof;

[3] the compound of the above-mentioned [1], wherein $R^1$ and $R^2$ are (1) both methyl groups optionally substituted by halogen atom(s), or (2) one is an ethyl group and the other is a hydrogen atom, or $R^1$ and $R^2$ form, together with the adjacent carbon atom, a cyclopropyl group, a cyclobutyl group, a 3-fluorophenyl group or a 3-methoxyphenyl group; and
$R^3$ and $R^4$ are the same or different and each is a hydrogen atom or a methyl group,
or a salt thereof;

[4] the compound of the above-mentioned [1], wherein $R^1$ and $R^2$ are the same or different and each is a $C_{1-3}$ alkyl group optionally substituted by halogen atom(s), or
$R^1$ and $R^2$ form, together with the adjacent carbon atom, a $C_{3-4}$ cycloalkyl group, or a phenyl group substituted by halogen atom(s); and
$R^3$ and $R^4$ are the same or different and each is a hydrogen atom or a $C_{1-3}$ alkyl group,
or a salt thereof;

[5] the compound of the above-mentioned [1], wherein $R^1$ and $R^2$ are both methyl groups optionally substituted by halogen atom(s), or
$R^1$ and $R^2$ form, together with the adjacent carbon atom, a cyclopropyl group, a cyclobutyl group or a 3-fluorophenyl group;
$R^3$ is a hydrogen atom; and
$R^4$ is a hydrogen atom or a methyl group, or a salt thereof;

[6] 8-(3-fluorophenyl)-2,3,4,5-tetrahydrothieno[2,3-f][1,4] oxazepine or a salt thereof;
[7] 8-cyclopropyl-2,3,4,5-tetrahydrothieno[2,3-f][1,4]oxazepine or a salt thereof;
[8] 8-(1-methylethyl)-2,3,4,5-tetrahydrothieno[2,3-f][1,4] oxazepine or a salt thereof;
[9] 8-cyclobutyl-2,3,4,5-tetrahydrothieno[2,3-f][1,4]oxazepine or a salt thereof;
[10] (2S)-8-(3-fluorophenyl)-2-methyl-2,3,4,5-tetrahydrothieno[2,3-f][1,4]oxazepine or a salt thereof;
[11] (2S)-2-methyl-8-(1-methylethyl)-2,3,4,5-tetrahydrothieno[2,3-f][1,4]oxazepine or a salt thereof;
[12] 8-(2,2,2-trifluoro-1-methylethyl)-2,3,4,5-tetrahydrothieno[2,3-f][1,4]oxazepine or a salt thereof;
[13] (2S)-2-methyl-8-(2,2,2-trifluoro-1-methylethyl)-2,3,4, 5-tetrahydrothieno[2,3-f][1,4]oxazepine or a salt thereof;
[14] a prodrug of the compound of the above-mentioned [1] or a salt thereof;

[15] a medicament comprising the compound of the above-mentioned
[1] or a salt thereof or a prodrug thereof;
[16] the medicament of the above-mentioned [15], which is a serotonin 5-HT$_{2C}$ receptor activator;
[17] the medicament of the above-mentioned [15], which is a drug for the prophylaxis or treatment of a lower urinary tract symptom, obesity and/or organ prolapse;
[18] a method for the prophylaxis or treatment of a lower urinary tract symptom, obesity and/or organ prolapse in a mammal, comprising administering an effective amount of the compound of the above-mentioned [1] or a salt thereof or a prodrug thereof to the mammal;
use of the compound of the above-mentioned [1] or a salt thereof or a prodrug thereof for the production of a drug for the prophylaxis or treatment of a lower urinary tract symptom, obesity and/or organ prolapse;
[20] the compound of the above-mentioned [1] or a salt thereof or a prodrug thereof for the prophylaxis or treatment of a lower urinary tract symptom, obesity and/or organ prolapse; and the like.

Effect of the Invention

Compound (I) or a prodrug thereof is useful as a drug for the prophylaxis or treatment of all serotonin 5-HT$_{2C}$ associated diseases, for example, lower urinary tract symptom, obesity and/or organ prolapse and the like, since it has a superior serotonin 5-HT$_{2C}$ receptor activating action.

DESCRIPTION OF EMBODIMENTS

The definition of each symbol in the formula (I) is explained in detail in the following.

The "halogen atom" in the present specification means a fluorine atom, a chlorine atom, a bromine atom, an iodine atom and the like.

The "$C_{1-3}$ alkyl group" in the present specification means, unless otherwise specified, a methyl group, an ethyl group, a propyl group, an isopropyl group and the like.

The "$C_{1-3}$ alkoxy group" in the present specification means, unless otherwise specified, a methoxy group, an ethoxy group, a propoxy group, an isopropoxy group and the like.

$R^1$ and $R^2$ are the same or different and each is a hydrogen atom or a $C_{1-3}$ alkyl group optionally substituted by halogen atom(s) (at least one of $R^1$ and $R^2$ is a $C_{1-3}$ alkyl group optionally substituted by halogen atom(s)), or $R^1$ and $R^2$ form, together with the adjacent carbon atom, (a) a $C_{3-4}$ cycloalkyl group optionally substituted by halogen atom(s), (b) a phenyl group substituted by substituent(s) selected from a halogen atom and a $C_{1-3}$ alkoxy group, or (c) a furyl group.

The "$C_{1-3}$ alkyl group" of the "$C_{1-3}$ alkyl group optionally substituted by halogen atom(s)" for $R^1$ or $R^2$ may be substituted by any number of substituents selected from the above-mentioned "halogen atom". The number of the "halogen atom" is not limited as long as substitution is possible, and is preferably 1-3 (more preferably 1 or 2, particularly preferably 1). When two or more "halogen atoms" are present, they may be the same or different.

As such "halogen atom", a fluorine atom is preferable.
As the "$C_{1-3}$ alkyl group optionally substituted by halogen atom(s)", a $C_{1-3}$ alkyl group optionally substituted by 1 to 3 halogen atoms (preferably, a fluorine atom) is preferable, and a methyl group, an ethyl group and a trifluoromethyl group are more preferable.

The "$C_{3-4}$ cycloalkyl group" of the "$C_{3-4}$ cycloalkyl group optionally substituted by halogen atom(s)" optionally formed by $R^1$ and $R^2$ together with the adjacent carbon atom may be substituted by any number of substituents selected from the above-mentioned "halogen atom". The number of the "halogen atom" is not limited as long as substitution is possible, and is preferably 1-3 (more preferably 1 or 2, particularly preferably 1). When two or more "halogen atoms" are present, they may be the same or different.

As such "halogen atom", a fluorine atom is preferable.
As the "$C_{3-4}$ cycloalkyl group optionally substituted by halogen atom(s)", a $C_{3-4}$ cycloalkyl group (preferably, a cyclopropyl group, a cyclobutyl group) is preferable.

The "phenyl group" of the "phenyl group substituted by substituent(s) selected from a halogen atom and a $C_{1-3}$ alkoxy group" optionally formed by $R^1$ and $R^2$ together with the adjacent carbon atom is substituted by any number of substituents selected from the above-mentioned "halogen atom" and the above-mentioned "$C_{1-3}$ alkoxy group". The number of the substituents is not limited as long as substitution is possible, and is preferably 1-3 (more preferably 1 or 2, particularly preferably 1). When two or more substituents are present, they may be the same or different.

As such "halogen atom", a fluorine atom is preferable.
As such "$C_{1-3}$ alkoxy group", a methoxy group is preferable.

As the "phenyl group substituted by substituent(s) selected from a halogen atom and a $C_{1-3}$ alkoxy group", a phenyl group substituted by a halogen atom (preferably, a fluorine atom) or a $C_{1-3}$ alkoxy group (preferably, a methoxy group) is preferable, and a 2-fluorophenyl group, a 3-fluorophenyl group and a 3-methoxyphenyl group are more preferable.

Examples of the "furyl group" optionally formed by $R^1$ and $R^2$ together with the adjacent carbon atom include a furan-2-yl group, a furan-3-yl group and the like, and a furan-3-yl group is preferable.

$R^1$ and $R^2$ are preferably the same or different and each is a hydrogen atom, or a $C_{1-3}$ alkyl group optionally substituted by halogen atom(s) (preferably, a fluorine atom) (at least one of $R^1$ and $R^2$ is a $C_{1-3}$ alkyl group optionally substituted by halogen atom(s) (preferably, a fluorine atom)), more preferably, the same or different and each is a hydrogen atom, a methyl group, an ethyl group, a trifluoromethyl group (at least one of $R^1$ and $R^2$ is a methyl group, an ethyl group or a trifluoromethyl group).

More preferably, $R^1$ and $R^2$ are (1) both methyl groups optionally substituted by halogen atom(s) (preferably, a fluorine atom), or (2) one is an ethyl group, and the other is a hydrogen atom.

In another embodiment, $R^1$ and $R^2$ are preferably the same or different and each is a $C_{1-3}$ alkyl group optionally substituted by halogen atom(s) (preferably, a fluorine atom), more preferably, both methyl groups optionally substituted by halogen atom(s) (preferably, a fluorine atom).

In addition, $R^1$ and $R^2$ also preferably form, together with the adjacent carbon atom, (a) a $C_{3-4}$ cycloalkyl group, (b) a phenyl group substituted by substituent(s) selected from a halogen atom and a $C_{1-3}$ alkoxy group, or (c) a furyl group.

Preferably, $R^1$ and $R^2$ form, together with the adjacent carbon atom, a $C_{3-4}$ cycloalkyl group; a phenyl group substituted by a halogen atom (preferably, a fluorine atom) or a $C_{1-3}$ alkoxy group (preferably, a methoxy group); or a furyl group, and more preferably form a cyclopropyl group, a cyclobutyl group, a 2-fluorophenyl group, a 3-fluorophenyl group, a 3-methoxyphenyl group or a furyl group (preferably, a furan-3-yl group).

In another embodiment, $R^1$ and $R^2$ preferably form, together with the adjacent carbon atom, a $C_{3-4}$ cycloalkyl group; or a phenyl group substituted by substituent (s) selected from a halogen atom and a $C_{1-3}$ alkoxy group, and more preferably form a cyclopropyl group, a cyclobutyl group, a 3-fluorophenyl group or a 3-methoxyphenyl group.

Particularly preferably, $R^1$ and $R^2$ form, together with the adjacent carbon atom, a cyclopropyl group, a cyclobutyl group or a 3-fluorophenyl group.

$R^3$ and $R^4$ are the same or different and each is a hydrogen atom or a $C_{1-3}$ alkyl group.

The "$C_{1-3}$ alkyl group" for $R^3$ or $R^4$ is preferably a methyl group.

$R^3$ is preferably a hydrogen atom or a methyl group, more preferably a hydrogen atom.

$R^4$ is preferably a hydrogen atom or a methyl group.

As compound (I), a compound wherein
$R^1$ and $R^2$ are the same or different and each is a hydrogen atom or a $C_{1-3}$ alkyl group (preferably, a methyl group, an ethyl group, a trifluoromethyl group) optionally substituted by halogen atom(s) (preferably, a fluorine atom) (at least one of $R^1$ and $R^2$ is a $C_{1-3}$ alkyl group (preferably, a methyl group, an ethyl group, a trifluoromethyl group) optionally substituted by halogen atom(s) (preferably, a fluorine atom)); or
$R^1$ and $R^2$ form, together with the adjacent carbon atom, (a) a $C_{3-4}$ cycloalkyl group, (b) a phenyl group substituted by a halogen atom (preferably, a fluorine atom) or a $C_{1-3}$ alkoxy group (preferably, a methoxy group), or (c) a furyl group; and
$R^3$ and $R^4$ are the same or different and each is a hydrogen atom or a $C_{1-3}$ alkyl group (preferably, a methyl group),
or a salt thereof is preferable.

More preferably, compound (I) is a compound wherein
$R^1$ and $R^2$ are the same or different and each is a $C_{1-3}$ alkyl group (preferably, a methyl group, an ethyl group, a trifluoromethyl group) optionally substituted by halogen atom(s) (preferably, a fluorine atom), or
$R^1$ and $R^2$ form, together with the adjacent carbon atom, a cyclopropyl group, a cyclobutyl group, a 2-fluorophenyl group, a 3-fluorophenyl group, a 3-methoxyphenyl group or a furyl group (preferably, a furan-3-yl group); and
$R^3$ and $R^4$ are the same or different and each is a hydrogen atom or a $C_{1-3}$ alkyl group (preferably, a methyl group),
or a salt thereof.

More preferably, compound (I) is a compound wherein
$R^1$ and $R^2$ are the same or different and each is a $C_{1-3}$ alkyl group (preferably, a methyl group, a trifluoromethyl group) optionally substituted by halogen atom(s) (preferably, a fluorine atom), or
$R^1$ and $R^2$ form, together with the adjacent carbon atom, a $C_{3-4}$ cycloalkyl group or a phenyl group substituted by halogen atom(s) (preferably, a fluorine atom); and
$R^3$ and $R^4$ are the same or different and each is a hydrogen atom or a $C_{1-3}$ alkyl group (preferably, a methyl group),
or a salt thereof.

Particularly preferably, compound (I) is a compound wherein
$R^1$ and $R^2$ are both methyl groups optionally substituted by halogen atom(s) (preferably, a fluorine atom), or
$R^1$ and $R^2$ form, together with the adjacent carbon atom, a cyclopropyl group, a cyclobutyl group or a 3-fluorophenyl group;
$R^3$ is a hydrogen atom; and
$R^4$ is a hydrogen atom or a methyl group,
or a salt thereof.

In another embodiment, as compound (I), a compound wherein
$R^1$ and $R^2$ are the same or different and each is a hydrogen atom or a $C_{1-3}$ alkyl group (preferably, a methyl group, an ethyl group, a trifluoromethyl group) optionally substituted by halogen atom(s) (preferably, a fluorine atom) (at least one of $R^1$ and $R^2$ is a $C_{1-3}$ alkyl group (preferably, a methyl group, an ethyl group, a trifluoromethyl group) optionally substituted by halogen atom(s) (preferably, a fluorine atom)); or
$R^1$ and $R^2$ form, together with the adjacent carbon atom, a $C_{3-4}$ cycloalkyl group, or a phenyl group substituted by substituent(s) selected from a halogen atom (preferably, a fluorine atom) and a $C_{1-3}$ alkoxy group (preferably, a methoxy group); and
$R^3$ and $R^4$ are the same or different and each is a hydrogen atom or a $C_{1-3}$ alkyl group (preferably, a methyl group),
or a salt thereof is preferable.

More preferably, compound (I) is a compound wherein
$R^1$ and $R^2$ are (1) both methyl groups optionally substituted by halogen atom(s) (preferably, a fluorine atom), or (2) one is an ethyl group and the other is a hydrogen atom, or
$R^1$ and $R^2$ form, together with the adjacent carbon atom, a cyclopropyl group, a cyclobutyl group, a 3-fluorophenyl group or a 3-methoxyphenyl group; and
$R^3$ and $R^4$ are the same or different and each is a hydrogen atom or a methyl group,
or a salt thereof.

In another embodiment, as compound (I), a compound wherein
$R^1$ and $R^2$ are the same or different and each is a $C_{1-3}$ alkyl group (preferably, a methyl group, an ethyl group, a trifluoromethyl group) optionally substituted by halogen atom(s) (preferably, a fluorine atom); or
$R^1$ and $R^2$ form, together with the adjacent carbon atom, a $C_{3-4}$ cycloalkyl group or a phenyl group substituted by halogen atom(s) (preferably, a fluorine atom); and
$R^3$ and $R^4$ are the same or different and each is a hydrogen atom or a $C_{1-3}$ alkyl group (preferably, a methyl group),
or a salt thereof is preferable.

More preferably, compound (I) is a compound wherein
$R^1$ and $R^2$ are the same or different and each is a $C_{1-3}$ alkyl group (preferably, a methyl group, an ethyl group, a trifluoromethyl group) optionally substituted by halogen atom(s) (preferably, a fluorine atom); or
$R^1$ and $R^2$ form, together with the adjacent carbon atom, a cyclopropyl group or a cyclobutyl group; and
$R^3$ and $R^4$ are the same or different and each is a hydrogen atom or a $C_{1-3}$ alkyl group (preferably, a methyl group),
or a salt thereof.

In a still another embodiment, as compound (I), a compound wherein
$R^1$ and $R^2$ are both methyl groups optionally substituted by halogen atom(s) (preferably, a fluorine atom), or
$R^1$ and $R^2$ form, together with the adjacent carbon atom, a cyclopropyl group, a cyclobutyl group or a 3-fluorophenyl group;
$R^3$ is a hydrogen atom; and
$R^4$ is a hydrogen atom or a methyl group,
or a salt thereof is preferable.

More preferably, compound (I) is a compound wherein
$R^1$ and $R^2$ are both methyl groups optionally substituted by halogen atom(s) (preferably, a fluorine atom), or
$R^1$ and $R^2$ form, together with the adjacent carbon atom, a cyclopropyl group or a cyclobutyl group;
$R^3$ is a hydrogen atom; and
$R^4$ is a hydrogen atom or a methyl group,
or a salt thereof.

As compound (I), the compounds described in the following Examples 1-21 or salts thereof are preferable, and particularly,
8-(3-fluorophenyl)-2,3,4,5-tetrahydrothieno[2,3-f][1,4]oxazepine or a salt thereof (Example 2),
8-cyclopropyl-2,3,4,5-tetrahydrothieno[2,3-f][1,4]oxazepine or a salt thereof (Example 3),
8-(1-methylethyl)-2,3,4,5-tetrahydrothieno[2,3-f][1,4]oxazepine or a salt thereof (Example 4),
8-cyclobutyl-2,3,4,5-tetrahydrothieno[2,3-f][1,4]oxazepine or a salt thereof (Example 5),
(2S)-8-(3-fluorophenyl)-2-methyl-2,3,4,5-tetrahydrothieno[2,3-f][1,4]oxazepine or a salt thereof (Example 12),
(2S)-2-methyl-8-(1-methylethyl)-2,3,4,5-tetrahydrothieno[2,3-f][1,4]oxazepine or a salt thereof (Example 15),
8-(2,2,2-trifluoro-1-methylethyl)-2,3,4,5-tetrahydrothieno[2,3-f][1,4]oxazepine or a salt thereof (Example 20), and
(2S)-2-methyl-8-(2,2,2-trifluoro-1-methylethyl)-2,3,4,5-tetrahydrothieno[2,3-f][1,4]oxazepine or a salt thereof (Example 21)
are preferable.

When compound (I) is a salt, examples of the salt include salt with inorganic base, ammonium salt, salt with organic base, salt with inorganic acid, salt with organic acid, salt with basic or acidic amino acid and the like.

Preferable examples of the salt with inorganic base include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Of these salts, pharmaceutically acceptable salts are preferable.

Compound (I) may be any of hydrate, non-hydrate, solvate and non-solvate.

Compounds labeled with an isotope (e.g., $^2$H, $^3$H, $^{11}$C, $^{14}$C, $^{18}$F, $^{35}$S, $^{125}$I etc.) and the like are also encompassed in compound (I).

In addition, a deuterium converter wherein $^1$H of compound (I) is converted to $^2$H(D) is also encompassed in compound (I).

The production methods of compound (I) of the present invention are explained in the following.

Compound (I) of the present invention can be produced, for example, using the following method A, method B, method B', method C, method D, or a method analogous thereto.

In each of the following production methods, the starting compound and production intermediate may be in the foam of a salt. Examples of such salt include those similar to the salt of the aforementioned compound (I) and the like.

In addition, the production intermediate obtained in each of the production methods can be used as a reaction mixture as it is or a crude product for the next reaction. It may be used after isolation and purification from the reaction mixture according to a conventional method and by a known means such as phase transfer, concentration, solvent extraction, fractionation, liquid conversion, crystallization, recrystallization, chromatography and the like.

When a compound of each formula is commercially available, the commercially available product can also be used directly.

Compound (I) can be produced, for example, according to method A shown below, or a method analogous thereto.

[Method A]

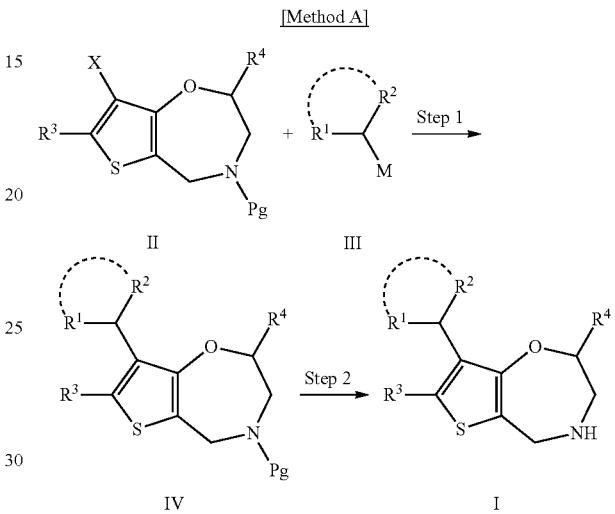

wherein Pg is a protecting group; X is a halogen atom; M is an optionally esterified boronic acid group, an optionally halogenated magnesium, an optionally halogenated zinc or an optionally alkylated tin; and other symbols are as defined above.

Examples of the "protecting group" for Pg include amino-protecting groups generally used for peptide synthesis and the like (e.g., a tert-butoxycarbonyl group, a benzyloxycarbonyl group, a formyl group, a p-nitrophenylsulfonyl group, a p-methoxybenzyl group) and the like, with preference given to a tert-butoxycarbonyl group.

Examples of the "halogen atom" for X include a fluorine atom, a chlorine atom, a bromine atom and an iodine atom, with preference given to a bromine atom.

step 1

In this step, a compound represented by the formula (II) or a salt thereof (hereinafter sometimes to be referred to as "compound (II)", same applies to other formulas) and compound (III) are subjected to a coupling reaction to give compound (IV).

This reaction can be carried out according to a method known per se [e.g., the method described in Chemical Reviews, 1995, vol. 95, page 2457, etc.] and, for example, in the presence of a transition metal catalyst and a base in a solvent that does not adversely influence the reaction.

The amount of compound (III) to be used varies depending on the substrate and other reaction conditions, and is generally 0.1 molar equivalent-20 molar equivalents, preferably 0.5 molar equivalents-10 molar equivalents, relative to compound (II).

As the transition metal catalyst, for example, palladium catalysts (e.g., palladium acetate, palladium chloride, tetrakis(triphenylphosphine)palladium, dichlorobis(triphenylphosphine)palladium etc.), nickel catalysts (e.g., nickel chloride etc.), iron catalysts (e.g., acetylacetone iron etc.) and the like are used, a ligand (e.g., tricyclohexylphosphine, triphenylphosphine, tri-tert-butylphosphine etc.) may be added where necessary, and metal oxide (e.g., copper oxide, silver oxide etc.) and the like may be used as a cocatalyst.

While the amount of the transition metal catalyst to be used varies depending on the kind of the catalyst, it is generally about 0.0001 molar equivalent-about 1 molar equivalent, preferably about 0.01 molar equivalent-about 0.5 molar equivalents, relative to compound (II). The amount of the ligand to be used is generally about 0.0001 molar equivalent-about 4 molar equivalents, preferably about 0.01 molar equivalent-about 2 molar equivalents, relative to compound (II). The amount of the cocatalyst to be used is generally about 0.0001 molar equivalent-about 4 molar equivalents, preferably about 0.01 molar equivalent-about 2 molar equivalents, relative to compound (II).

Examples of, the base include organic amines (e.g., trimethylamine, triethylamine, diisopropylethylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide etc.), alkali metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium hexamethyldisilazide, sodium hexamethyldisilazide, potassium hexamethyldisilazide etc.) and the like. Of these, alkali metal salts such as sodium carbonate, potassium carbonate, cesium carbonate, sodium phosphate, potassium phosphate and the like; alkali metal alkoxides such as sodium tert-butoxide, potassium tert-butoxide and the like; organic amines such as triethylamine, diisopropylethylamine and the like and the like are preferable.

The amount of the base to be used is generally about 0.1 molar equivalent-about 10 molar equivalents, preferably about 1 molar equivalent-about 5 molar equivalents, relative to compound (II).

Examples of the solvent that does not adversely influence the reaction include hydrocarbons (e.g., benzene, toluene, xylene etc.), halogenated hydrocarbons (e.g., chloroform, 1,2-dichloroethane etc.), nitriles (e.g., acetonitrile etc.), ethers (e.g., dimethoxyethane, tetrahydrofuran etc.), alcohols (e.g., methanol, ethanol etc.), aprotic polar solvents (e.g., N,N-dimethylformamide, dimethyl sulfoxide, hexamethylphosphoramide etc.), water and the like. These solvents may be used in a mixture at an appropriate ratio.

The reaction temperature is generally about −10° C. to about 200° C., preferably about 0° C. to about 150° C.

The reaction time is generally about 0.5 hr-48 hr, preferably 0.5 hr-20 hr.

step 2

In this step, compound (I) is produced by removing the protecting group of compound (IV). This reaction can be carried out by a method known per se. When the protecting group is a tert-butoxycarbonyl group in the preferable embodiment, this reaction can be generally carried out by reacting an acid in a solvent that does not adversely influence the reaction where necessary.

Examples of the acid include hydrochloric acid, hydrobromic acid, sulfuric acid, trifluoroacetic acid, trifluoromethanesulfonic acid, hydrogen chloride and the like.

The amount of the acid to be used is generally about 1 molar equivalent-about 1000 molar equivalents, preferably about 1 molar equivalent-about 100 molar equivalents, relative to compound (IV).

Examples of the solvent that does not adversely influence the reaction include alcohols (e.g., methanol etc.), ethers (e.g., tetrahydrofuran etc.), halogenated hydrocarbons (e.g., chloroform etc.), aromatic hydrocarbons (e.g., toluene etc.), amides (e.g., N,N-dimethylformamide etc.), sulfoxides (e.g., dimethyl sulfoxide etc.), esters (e.g., ethyl acetate etc.) and the like. These solvents may be used in a mixture at an appropriate ratio.

The amount of the solvent to be used is generally 1-fold volume-100-fold volume relative to compound (IV).

The reaction temperature is generally about −50° C. to about 250° C., preferably 0° C. to 120° C.

The reaction time is generally about 20 min-about 24 hr.

Compound (I) produced by such method can be isolated and purified, for example, by a known separation and purification means such as distillation, solvent extraction, crystallization, recrystallization, phase transfer, chromatography and the like.

In compound (I), the following compound (Ia) and compound (Ia') can also be produced according to method B or method B' shown below, respectively.

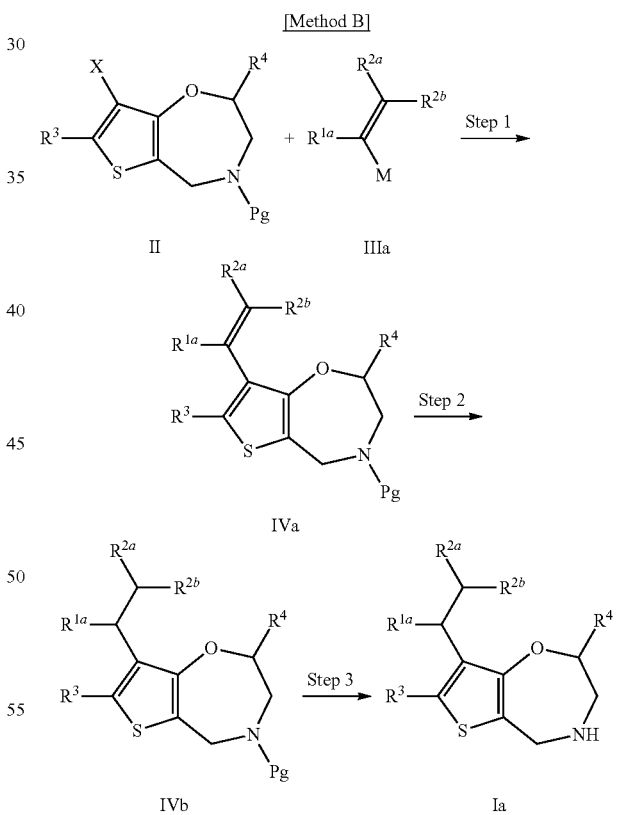

wherein $R^{1a}$ is a hydrogen atom or a $C_{1-3}$ alkyl group optionally substituted by halogen atom(s); $R^{2a}$ and $R^{2b}$ are the same or different and each is a hydrogen atom or a $C_{1-2}$ alkyl group (e.g., a methyl group, an ethyl group) optionally substituted by halogen atom(s) (when one of $R^{2a}$ and $R^{2b}$ is an ethyl group optionally substituted by halogen atom(s), the other is a hydrogen atom); and other symbols are as defined above.

step 1

In this step, compound (IVa) is produced by subjecting compound (II) and compound (IIIa) to a coupling reaction. This reaction can be carried out in the same manner as in the aforementioned method A, step 1, or according to a method analogous thereto.

step 2

In this step, compound (IVb) is produced by subjecting compound (IVa) to a reduction reaction.

This reaction can be carried out according to a method known per se [e.g., the method described in Manuals for organic chemical experiments (*Yuukikagaku Jikken no Tebiki*) 3, Synthesis reaction I, KAGAKUDOJIN, pages 38-40 etc.], and can be carried out, for example, in the presence of a metal catalyst and using a hydrogen source in a solvent that does not adversely influence the reaction.

Examples of the metal catalyst include platinum, palladium, rhodium, ruthenium, nickel, palladium oxide, palladium on carbon, Wilkinson complex and the like. While the amount of the metal catalyst to be used varies depending on the kind of the metal catalyst to be used, it is generally about 0.1 molar equivalent-about 5 molar equivalents, preferably about 0.1 molar equivalent-about 2 molar equivalents, relative to compound (IVa).

As the hydrogen source, hydrogen gas, ammonium formate, hydrazine and the like are generally used. The hydrogen gas is generally used under normal pressure or under pressurization.

Examples of the solvent that does not adversely influence the reaction include hydrocarbons (e.g., benzene, toluene, xylene etc.), nitriles (e.g., acetonitrile etc.), ethers (e.g., dimethoxyethane, tetrahydrofuran), alcohols (e.g., methanol, ethanol etc.), aprotic polar solvents (e.g., N,N-dimethylformamide, dimethyl sulfoxide, hexamethylphosphoramide etc.), water and the like. These solvents may be used in a mixture at an appropriate ratio.

The reaction temperature is generally about −100° C. to about 100° C., preferably about −78° C. to about 50° C.

The reaction time is generally about 0.5 hr-about 48 hr, preferably about 0.5 hr-about 16 hr.

step 3

In this step, compound (Ia) is produced by removing the protecting group of compound (IVb). When the protecting group is a tert-butoxycarbonyl group, this reaction can be carried out in the same manner as in the aforementioned method A, step 2, or according to a method analogous thereto.

Compound (Ia) produced by such method can be isolated and purified by a known separation and purification means, for example, distillation, solvent extraction, crystallization, recrystallization, phase transfer, chromatography and the like.

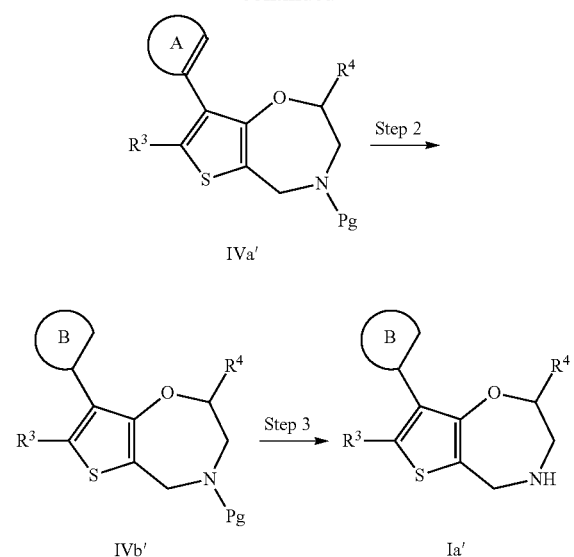

wherein ring A is a $C_{3-4}$ cycloalkenyl group; ring B is a $C_{3-4}$ cycloalkyl group; and other symbols are as defined above.

step 1

In this step, compound (IVa') is produced by subjecting compound (II) and compound (IIIa') to a coupling reaction. This reaction can be carried out in the same manner as in the aforementioned method A, step 1, or according to a method analogous thereto.

step 2

In this step, compound (IVb') is produced by subjecting compound (IVa') to a reduction reaction. This reaction can be carried out in the same manner as in the aforementioned method B, step 2, or according to a method analogous thereto.

step 3

In this step, compound (Ia') is produced by removing a protecting group of compound (IVb'). When the protecting group is a tert-butoxycarbonyl group, this step can be carried out in the same manner as in the aforementioned method B, step 3, or according to a method analogous thereto.

Compound (Ia') produced by such method can be isolated and purified by a known separation and purification means, for example, distillation, solvent extraction, crystallization, recrystallization, phase transfer, chromatography and the like.

In compound (I), the following compound (Ib) can also be produced by method C shown below or a method analogous thereto.

[Method B']

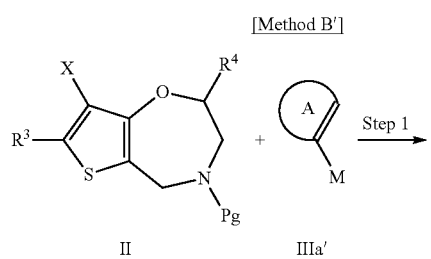

[Method C]

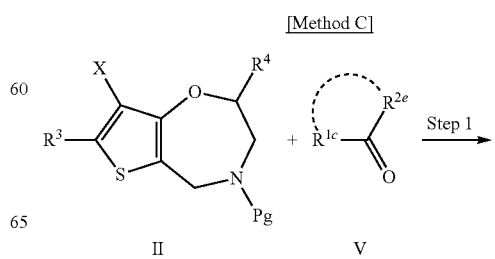

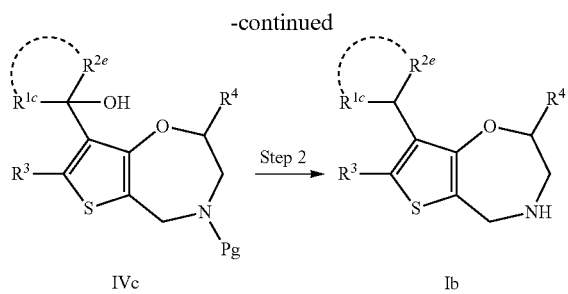

wherein $R^{1c}$ and $R^{2e}$ are the same or different and each is a hydrogen atom or a $C_{1-3}$ alkyl group optionally substituted by halogen atom(s) (at least one of $R^{1c}$ and $R^{2e}$ is a $C_{1-3}$ alkyl group optionally substituted by halogen atom(s)), or $R^{1c}$ and $R^{2e}$ form, together with the adjacent carbon atom, a $C_{3-4}$ cycloalkyl group; and other symbols are as defined above.

step 1

In this step, compound (IVc) is produced by subjecting compound (II) to an addition reaction to compound (V).

This reaction can be carried out according to a method known per se [e.g., the method described in Jikken Kagaku Kouza, 4th edition, organic synthesis II, alcohol.amine, Maruzen Company, Limited, pages 81-93, etc.] and, for example, by converting compound (II) to an organic metal compound, and adding the compound to compound (V) in a solvent that does not adversely influence the reaction.

The organic metal compound is obtained by reacting the above-mentioned compound (II) with a reagent to be a metal source (e.g., metal lithium, butyllithium, metal magnesium, isopropylmagnesium chloride etc.).

The amount of the reagent to be a metal source to be used is generally about 1 molar equivalent-about 5 molar equivalents, preferably about 1 molar equivalent-about 2 molar equivalents, relative to compound (II).

The amount of compound (V) to be used is generally about 0.2 molar equivalents-about 10 molar equivalents, preferably about 0.5 molar equivalents-about 5 molar equivalents, relative to compound (II).

Examples of the solvent that does not adversely influence the reaction include hydrocarbons (e.g., hexane etc.), ethers (e.g., diethyl ether, dimethoxyethane, tetrahydrofuran etc.) and the like. These solvents may be used in a mixture at an appropriate ratio.

The reaction temperature is generally about −100° C. to about 100° C., preferably about −78° C. to about 50° C.

The reaction time is generally about 0.5 hr-about 48 hr, preferably about 0.5 hr-about 16 hr.

step 2

In this step, compound (Ib) is produced by simultaneously or gradually subjecting compound (IVc) to a reduction reaction and deprotection.

The reduction reaction can be carried out by reacting compound (IVc) with a reducing agent in a solvent that does not adversely influence the reaction where necessary, or by subjecting compound (IVc) to a hydrogenation reaction using a metal catalyst. The reaction may be carried out in the presence of a hydroxyl group activator where necessary.

Examples of the reducing agent include silicon reagents (e.g., triethylsilane, trimethylsilane etc.), aluminum reagents (e.g., lithium aluminum hydride (LiAlH₄), diisobutylaluminum hydride (DIBAL-H), sodium bis(2-methoxyethoxy)aluminum hydride (Red-Al), alane (AlH₃) etc.), boron reagents (e.g., borane (BH₃), 9-borabicyclo[3.3.1]nonane (9-BBN), sodium borohydride (NaBH₄), sodium cyanoborohydride (NaBH₃CN), sodium triacetoxyborohydride (NaBH(OAc)₃) etc.) and the like. Of these, silicon reagents are preferable. The amount of the reducing agent to be used varies depending on the kind of the solvent and other reaction conditions, and is generally about 1 molar equivalent-about 20 molar equivalents, preferably about 1 molar equivalent-about 5 molar equivalents, relative to compound (IVc).

Examples of the metal catalyst to be used for the hydrogenation reaction include platinum, palladium, rhodium, ruthenium, nickel, palladium oxide, palladium on carbon, Wilkinson complex and the like. While the amount of the metal catalyst to be used varies depending on the kind of the catalyst, it is generally about 0.1 molar equivalent-about 5 molar equivalents, preferably about 0.1 molar equivalent-about 2 molar equivalents, relative to compound (IVc). In addition, as the hydrogen source to be used for the hydrogenation reaction, hydrogen gas, ammonium formate, hydrazine and the like are generally used. The hydrogen gas is generally used under normal pressure or under pressurization.

Examples of the solvent that does not adversely influence the reaction include alcohols (e.g., methanol, ethanol, propanol, 2-propanol, butanol, isobutanol, tert-butanol etc.), hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), carboxylic acids (e.g., acetic acid, trifluoroacetic acid etc.) and the like. These solvents may be used in a mixture at an appropriate ratio.

The reaction temperature is generally about −80° C. to about 200° C., preferably about −80° C. to about 100° C.

The reaction time varies depending on the kind of to compound (IVc), reaction temperature and the like, and is generally about 0.1 hr-about 100 hr, preferably about 0.5 hr-about 24 hr.

Examples of the hydroxyl group activator include acids (e.g., hydrochloric acid, hydrobromic acid, sulfuric acid, trifluoroacetic acid, trifluoromethanesulfonic acid, hydrogen chloride, methanesulfonic acid etc.), acid anhydrides (e.g., acetic anhydride etc.), and acid halides (e.g., acetyl chloride, p-toluenesulfonyl chloride etc.). Of these, an acid, particularly trifluoroacetic acid, is preferable. The amount of the acid to be used is generally about 0.1 molar equivalent-about 500 molar equivalents, preferably about 1 molar equivalent-about 100 molar equivalents, relative to compound (IVc).

As the activator, a base may also be used where necessary. Examples of such base include those mentioned in method A, step 1, above and the like.

When the activator is used, a protecting group-removal reaction may simultaneously proceed to give compound (Ib). In such a case, generally, deprotection shown below is not necessary.

When the deprotection is necessary, the reaction mixture of the aforementioned reduction reaction is directly, or after purification, subjected to deprotection to give compound (Ib). When the protecting group is a tert-butoxycarbonyl group, this reaction can be carried out in the same manner as in the aforementioned method A, step 2, or a method analogous thereto.

Compound (Ib) produced by such method can be isolated and purified by a known separation and purification means, for example, distillation, solvent extraction, crystallization, recrystallization, phase transfer, chromatography and the like.

In compound (I), compound (Ic) wherein $R^3$ is a $C_{1-3}$ alkyl group can also be produced by, for example, method D shown below.

[Method D]

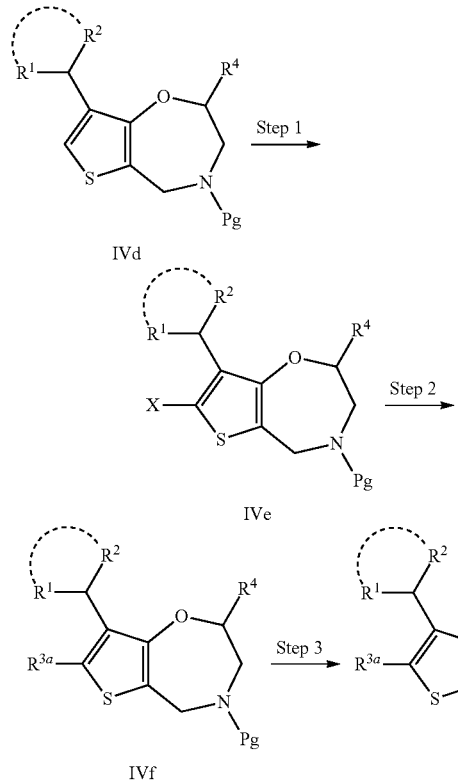

wherein R³ is a C$_{1-3}$ alkyl group, and other symbols are as defined above.

step 1

In this step, compound (IVe) is produced by subjecting compound (IVd) to a halogenation. This reaction can be carried out by a method known per se, and generally by reacting a halogenating agent in a solvent that does not adversely influence the reaction.

Examples of the halogenating agent include iodine, N-bromosuccinimide, bromine, pyridinium bromide perbromide, N-chlorosuccinimide and the like. The amount of the halogenating agent to be used is generally 0.5 molar equivalents-10 molar equivalents, preferably about 1 molar equivalent-about 100 molar equivalents, relative to compound (IVd).

Examples of the solvent that does not adversely influence the reaction include nitriles (e.g., acetonitrile etc.), ethers (e.g., tetrahydrofuran etc.), halogenated hydrocarbons (e.g., chloroform etc.), aromatic hydrocarbons (e.g., toluene etc.), amides (e.g., N,N-dimethylformamide etc.), sulfoxides (e.g., dimethyl sulfoxide etc.), esters (e.g., ethyl acetate etc.), acetic acid and the like. These solvents may be used in a mixture at an appropriate ratio. The amount of the solvent to be used is generally 1-fold volume-100-fold volume, relative to compound (IVd).

The reaction temperature is generally about −50° C. to about 250° C., preferably 0° C.-120° C.

The reaction time is generally about 0.5 hr-about 24 hr.

step 2

In this step, compound (IVf) is produced by subjecting compound (IVe) to an alkylation reaction. This reaction can be carried out by a method known per se or a method analogous thereto, and generally, a coupling reaction of compound (IVe) and a compound represented by the formula: R$^{3a}$-M wherein each symbol is as defined above is used. The coupling reaction can be carried out in the same manner as in the aforementioned method A, step 1, or according to a method analogous thereto.

step 3

In this step, compound (Ic) is produced by removing the protecting group of compound (IVf). When the protecting group is a tert-butoxycarbonyl group, this step can be carried out in the same manner as in the aforementioned method A, step 2, or according to a method analogous thereto.

Compound (Ic) produced by such method can be isolated and purified by a known separation and purification means, for example, distillation, solvent extraction, crystallization, recrystallization, phase transfer, chromatography and the like.

Compound (II) to be used for the production of compound (I) can be produced by method E or method F shown below.

[Method E]

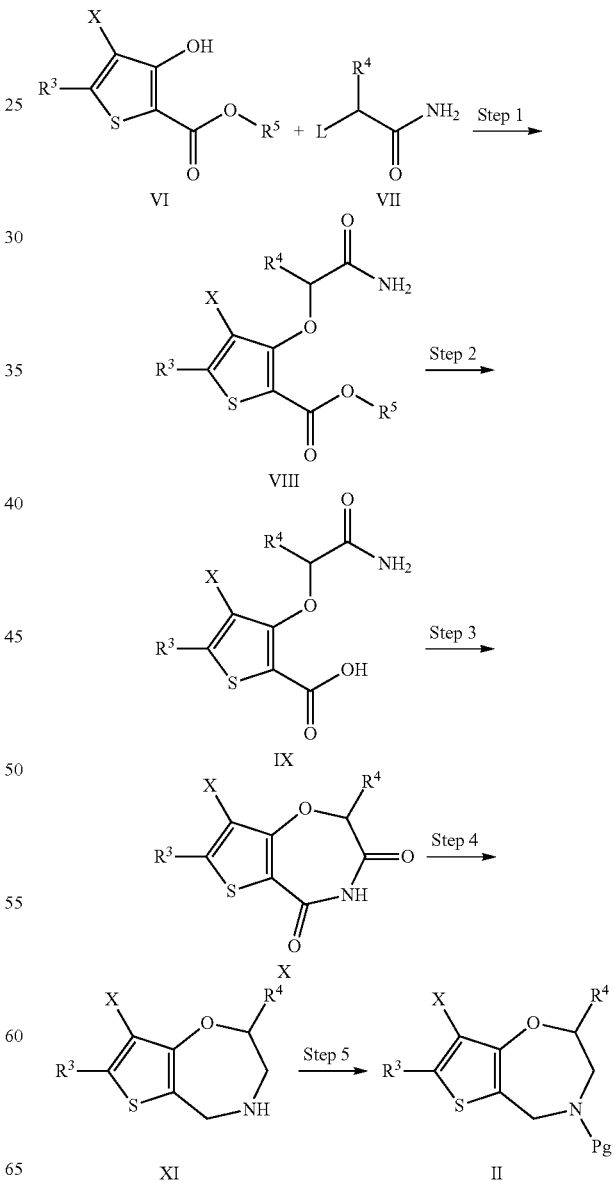

wherein $R^5$ is a $C_{1-6}$ alkyl group or a benzyl group; L is a leaving group (e.g., a chlorine atom, a bromine atom, a p-toluenesulfonyloxy group etc.); and other symbols are as defined above.

step 1

In this step, compound (VIII) is produced by reacting compound (VI) with compound (VII) in the presence of a base. This reaction can be carried out according to a method known per se, for example, in the presence of a base in a solvent that does not adversely influence the reaction.

As compound (VI) and compound (VII), commercially available products or those produced by a method known per se may be used directly or after purification. The amount of compound (VII) to be used is generally about 1 molar equivalent-about 5 molar equivalents, preferably about 1 molar equivalent-about 2 molar equivalents, relative to compound (VI).

Examples of the base include alkali metal hydrides (e.g., potassium hydride, sodium hydride etc.), inorganic bases (e.g., alkali metal hydroxides such as lithium hydroxide, sodium hydroxide, potassium hydroxide and the like; alkali metal hydrogencarbonates such as sodium hydrogen carbonate, potassium hydrogen carbonate and the like; alkali metal carbonates such as sodium carbonate, potassium carbonate and the like; alkali metal alkoxides such as sodium methoxide, sodium ethoxide and the like etc.), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridazine, 4-dimethylaminopyridine etc.) and the like. Of these, alkali metal hydrides such as sodium hydride and the like, inorganic bases such as potassium carbonate and the like are preferable. While the amount of the base to be used varies depending on the kind of the solvent and other reaction conditions, it is generally about 1 molar equivalent-about 10 molar equivalents, preferably about 1 molar equivalent-about 5 molar equivalents, relative to compound (VI).

Examples of the solvent that does not adversely influence the reaction include hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), nitriles (e.g., acetonitrile etc.), amides. (e.g., N,N-dimethylformamide, N,N-dimethylacetamide etc.), sulfoxides (e.g., dimethyl sulfoxide etc.), water and the like. These solvents may be used in a mixture at an appropriate ratio.

The reaction temperature is generally about −50° C. to about 200° C., preferably about 0° C. to about 150° C.

The reaction time varies depending on the kind of compound (VI), reaction temperature and the like, and is generally about 0.1 hr-about 100 hr, preferably about 0.5 hr-about 24 hr.

step 2

In this step, compound (IX) is produced by subjecting compound (VIII) to hydrolysis. This reaction can be carried out according to a conventional method in the presence of an acid or a base in an aqueous solvent.

Examples of the acid include hydrochloric acid, sulfuric acid, acetic acid, hydrobromic acid and the like.

Examples of the base include alkali metal carbonates such as potassium carbonate, sodium carbonate and the like; alkali metal alkoxides such as sodium methoxide and the like; alkali metal hydroxides such as potassium hydroxide, sodium hydroxide, lithium hydroxide and the like; and the like.

The amount of the acid or base to be used is generally an excess amount relative to compound (VIII). The amount of the acid to be used is preferably about 2 molar equivalents-about 50 molar equivalents, relative to compound (VIII). The amount of the base to be used is preferably about 1.2 molar equivalents-about 5 molar equivalents, relative to compound (VIII).

Examples of the aqueous solvent include alcohols such as methanol, ethanol and the like; ethers such as tetrahydrofuran, dioxane, diethyl ether and the like; a mixed solvent of one or more kinds of solvents selected from dimethyl sulfoxide, acetone and the like, and water, and the like. The amount of the aqueous solvent to be used is, for example, 1-fold volume 30-100-fold volume, relative to compound (VIII).

The reaction temperature is generally about −20° C. to about 150° C., preferably about −10° C. to about 100° C.

The reaction time is generally about 0.1 hr-20 hr.

step 3

In this step, compound (X) is produced by reacting compound (IX) with a condensing agent. This reaction can be carried out according to a method known per se.

Examples of the condensing agent include 1-ethyl-3-(3-dimethylaminopropyl)carbodiimide hydrochloride, N,N-dicyclohexylcarbodiimide, carbonyldiimidazole and the like.

The amount of the condensing agent to be used is generally about 1 molar equivalent-about 10 molar equivalents, preferably about 1 molar equivalent-about 5 molar equivalents, relative to compound (IX).

In this reaction, an additive may be used where necessary. Examples of the additive include 1-hydroxybenzotriazole and the like. The amount of the additive to be used is generally about 1 molar equivalent-about 5 molar equivalents, preferably about 1 molar equivalent-about 2 molar equivalents, relative to compound (IX).

In this reaction, a base may be used where necessary. Examples of the base include alkali metal hydrides (e.g., potassium hydride, sodium hydride etc.), inorganic bases (e.g., alkali metal hydroxides such as lithium hydroxide, sodium hydroxide, potassium hydroxide and the like; alkali metal hydrogencarbonates such as sodium hydrogen carbonate, potassium hydrogen carbonate and the like; alkali metal carbonates such as sodium carbonate, potassium carbonate and the like; alkali metal alkoxides such as sodium methoxide, sodium ethoxide and the like, etc.), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridazine, 4-dimethylaminopyridine etc.) and the like. While the amount of the base to be used varies depending on the kind of the solvent and other reaction conditions, it is generally about 0.1 molar equivalent-about 10 molar equivalents, preferably about 1 molar equivalent-about 5 molar equivalents, relative to compound (IX).

This reaction can be carried out, for example, in a solvent that does not adversely influence the reaction. Examples of the solvent that does not adversely influence the reaction include hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.), water and the like. These solvents may be used in a mixture at an appropriate ratio.

The reaction temperature is generally about −50° C. to about 200° C., preferably about 0° C. to about 150° C.

The reaction time varies depending on the kind of compound (IX), reaction temperature and the like, and is generally about 0.1 hr-about 100 hr, preferably about 0.5 hr-about 24 hr.

step 4

In this step, compound (XI) is produced by subjecting compound (X) to a reduction reaction. This reaction can be carried out according to a method known per se, and can be generally carried out in the presence of a reducing agent, where necessary, in a solvent that does not adversely influence the reaction.

Examples of the reducing agent include aluminum reagents (e.g., lithium aluminum hydride (LiAlH$_4$), diisobutylaluminum hydride (DIBAL-H), sodium bis(2-methoxyethoxy)aluminum hydride (Red-Al), alane (AlH$_3$) etc.), boron reagents (e.g., borane (BH$_3$), tetrahydrofuran-borane complex, 9-borabicyclo[3.3.1]nonane (9-BBN), sodium borohydride (NaBH$_4$), sodium cyanoborohydride (NaBH$_3$CN), sodium triacetoxyborohydride (NaBH(OAc)$_3$) etc.) and the like. Of these, aluminum reagents and boron reagents, particularly lithium aluminum hydride, tetrahydrofuran-borane complex and the like, are preferable. While the amount of the reducing agent to be used varies depending on the kind of the solvent and other reaction conditions, it is generally about 1 molar equivalent-about 10 molar equivalents, preferably about 1 molar equivalent-about 5 molar equivalents, relative to compound (X).

Examples of the solvent that does not adversely influence the reaction include alcohols (e.g., methanol, ethanol, propanol, 2-propanol, butanol, isobutanol, tert-butanol etc.), hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), carboxylic acids (e.g., acetic acid, trifluoroacetic acid etc.) and the like. These solvents may be used in a mixture at an appropriate ratio.

The reaction temperature is generally about −80° C. to about 200° C., preferably about −80° C. to about 100° C.

The reaction time varies depending on the kind of compound (X), reaction temperature and the like, and is generally about 0.1 hr-about 100 hr, preferably about 0.5 hr-about 24 hr.

step 5

In this step, compound (II) is produced by introducing a protecting group into compound (XI). This reaction can be carried out according to a conventional method for introduction of an objective protecting group. For example, when Pg is a tert-butoxycarbonyl group, this reaction is carried out using di-tert-butyl dicarbonate in the presence of a base in a solvent that does not adversely influence the reaction, where necessary.

The amount of the di-tert-butyl dicarbonate to be used is generally about 0.5 molar equivalents-about 10 molar equivalents, preferably about 1 molar equivalent-about 3 molar equivalents, relative to compound (XI).

Examples of the base include sodium hydroxide, triethylamine, tributylamine, diisopropylethylamine, potassium carbonate, sodium carbonate, sodium hydride, potassium hydride and the like. The amount of the base to be used is generally about 0.1 molar equivalent-about 10 molar equivalents, preferably about 1 molar equivalent-about 5 molar equivalents, relative to compound (XI).

Examples of the solvent that does not adversely influence the reaction include ethers such as tetrahydrofuran and the like; halogenated hydrocarbons such as chlorofo/m and the like; aromatic hydrocarbons such as toluene and the like; amides such as N,N-dimethylformamide and the like; sulfoxides such as dimethylsulfoxide and the like, and the like. These solvents may be used in a mixture at an appropriate ratio. The amount of the solvent to be used is generally 1-fold volume-100-fold volume, relative to compound (XI).

The reaction temperature is generally about −50° C. to about 250° C., preferably 0° C. to 120° C.

The reaction time is generally about 0.5-about 24 hr.

The thus-obtained compound (II) can be isolated and purified by a known separation and purification means, for example, concentration, concentration under reduced pressure, solvent extraction, crystallization, recrystallization, phase transfer, chromatography and the like.

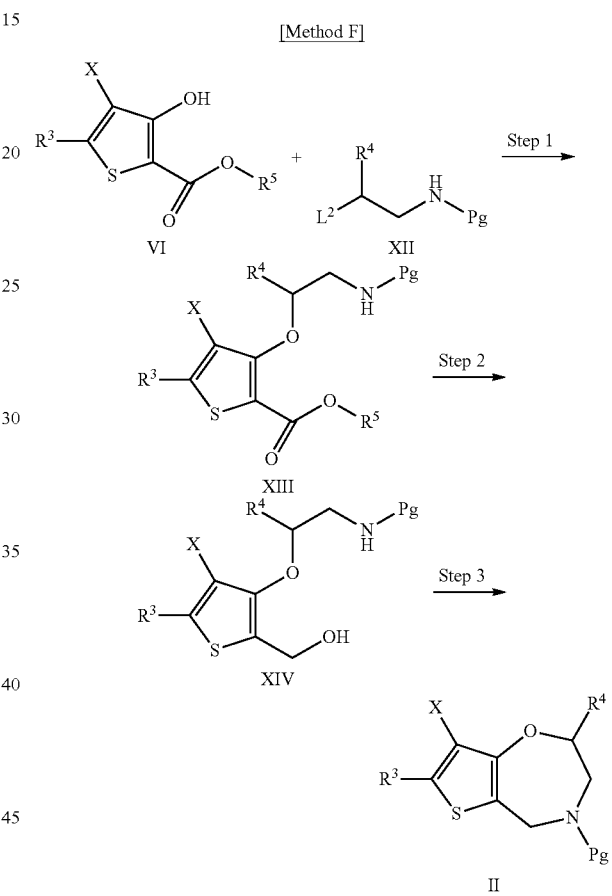

[Method F]

wherein L$^2$ is a leaving group (e.g., a chlorine atom, a bromine atom, a p-toluenesulfonyloxy group etc.) or a hydroxyl group, and other symbols are as defined above.

step 1

In this step, compound (XIII) is produced by reacting compound (VI) with compound (XII).

This reaction can be carried out according to a method known per se or a method analogous thereto. For example, when L$^2$ is a leaving group, the reaction can be carried out in the presence of a base in a solvent that does not adversely influence the reaction, where necessary. In this case, this reaction can be carried out in the same manner as in the aforementioned method E, step 1.

In addition, for example, when L$^2$ is a hydroxyl group, this step can be carried out by the Mitsunobu reaction. This reaction can be carried out according to a method known per se, for example, the method described in Synthesis, page 1 (1981) and the like, or a method analogous thereto. That is, this reaction is carried out in the presence of an organic phosphorus compound and electrophile in a solvent that does not adversely influence the reaction.

Examples of the organic phosphorus compound include triphenylphosphine, tri-n-butylphosphine and the like.

Examples of the electrophile include diethyl azodicarboxylate, diisopropyl azodicarboxylate, azodicarbonyldipiperazine and the like.

The amount of each of the organic phosphorus compound and electrophile to be used is generally 0.5 molar equivalents-10 molar equivalents, preferably about 1 molar equivalent-about 5 molar equivalents, relative to compound (VI).

Examples of the solvent that does not adversely influence the reaction include ethers such as diethyl ether, tetrahydrofuran, dioxane and the like; halogenated hydrocarbons such as chloroform, methylene chloride and the like; aromatic hydrocarbons such as benzene, toluene, xylene and the like; amides such as N,N-dimethylformamide and the like; sulfoxides such as dimethyl sulfoxide and the like, and the like. These solvents may be used in a mixture at an appropriate ratio. The amount of the solvent to be used is, for example, 1-fold volume-100-fold volume, relative to compound (VI).

The reaction temperature is generally about −50° C. to about 150° C., preferably about −10° C. to about 100° C.

The reaction time is generally about 0.5 hr-about 20 hr.

step 2

In this step, compound (XIV) is produced by subjecting compound (XIII) to a reduction reaction. This reaction can be carried out by a method known per se and, for example, by reacting a reducing agent in a solvent that does not adversely influence the reaction where necessary.

Examples of the reducing agent include aluminum reagents (e.g., lithium aluminum hydride (LiAlH$_4$), diisobutylaluminum hydride (DIBAL-H), sodium bis(2-methoxyethoxy)aluminum hydride (Red-Al), alane (AlH$_3$) etc.), boron reagents (e.g., borane (BH$_3$), 9-borabicyclo[3.3.1]nonane (9-BBN), sodium borohydride (NaBH$_4$), lithium borohydride (LiBH$_4$), sodium cyanoborohydride (NaBH$_3$CN), sodium triacetoxyborohydride (NaBH(OAc)$_3$) etc.) and the like. Of these, sodium borohydride and lithium borohydride are preferable. While the amount of the reducing agent to be used varies depending on the kind of the solvent and other reaction conditions, it is generally about 1 molar equivalent-about 10 molar equivalents, preferably about 1 molar equivalent-about 5 molar equivalents, relative to compound (XIII).

Examples of the solvent that does not adversely influence the reaction include alcohols (e.g., methanol, ethanol, propanol, 2-propanol, butanol, isobutanol, tert-butanol etc.), hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), carboxylic acids (e.g., acetic acid, trifluoroacetic acid etc.) and the like. These solvents may be used in a mixture at an appropriate ratio.

The reaction temperature is generally about −80° C. to about 200° C., preferably about −80° C. to about 100° C.

The reaction time varies depending on the kind of compound (XIII), reaction temperature and the like, and is generally about 0.1 hr-about 100 hr, preferably about 0.5 hr-about 24 hr.

In addition, this step can also be carried out by subjecting a reactive derivative obtained by activating carboxylic acid obtained by hydrolysis of compound (XIII) to the above-mentioned reduction reaction.

The hydrolysis is generally carried out using an acid or a base in a solvent that does not adversely influence the reaction, for example, in the same manner as in the aforementioned method E, step 2.

The obtained carboxylic acid is directly, or after isolation and purification, converted to a corresponding reactive derivative.

Examples of the reactive derivative include acid halides (e.g., acid chloride, acid bromide), mixed acid anhydride and activated ester, and these are produced by a method known per se.

For example, the conversion to the mixed acid anhydride can be carried out by reaction with chloroformic acid ester (e.g., methyl chloroformate, isobutyl chloroformate) in a solvent that does not adversely influence the reaction in the presence of a base (e.g., triethylamine, N,N-diisopropylethylamine) where necessary.

While the amount of the chloroformic acid ester to be used varies depending on the kind of the solvent and other reaction conditions, it is generally about 0.5 molar equivalents-about 50 molar equivalents, preferably about 1 molar equivalent-about 5 molar equivalents, relative to compound (XIII).

Examples of the solvent that does not adversely influence the reaction include hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.) and the like. These solvents may be used in a mixture at an appropriate ratio.

The reaction temperature is generally about −50° C. to about 150° C., preferably about 0° C. to about 80° C.

The reaction time varies depending on the kind of compound (XVI), reaction temperature and the like, and is generally about 0.1 hr-about 100 hr, preferably about 0.2 hr-about 24 hr.

The thus-obtained reactive derivative can be subjected to a reduction reaction directly in the form of a reaction mixture or after purification where necessary.

step 3

In this step, compound (II) is produced by activating a hydroxyl group of compound (XIV) and continuously subjecting the compound to a cyclization reaction. The cyclization reaction following activation of the hydroxyl group can be carried out simultaneously with the activation of the hydroxyl group, or in a stepwise manner.

Examples of a method for simultaneous cyclization reaction mentioned above with the activation of the hydroxyl group include a method including subjecting compound (XIV) to an intramolecular Mitsunobu reaction and the like. In this case, compound (II) is produced by a method similar to the Mitsunobu reaction in the above-mentioned step 1 or a method analogous thereto.

When the above-mentioned cyclization reaction is carried out in a stepwise manner from the activation of the hydroxyl group, the activation of the hydroxyl group is carried out according to a method generally used for activation of a hydroxyl group, for example, by reacting compound (XIV) with a sulfonylating agent in the presence of a base where necessary in a solvent that does not adversely influence the reaction.

Examples of the sulfonylating agent include methanesulfonyl chloride, methanesulfonic anhydride, p-toluenesulfonyl chloride and the like. While the amount of the sulfonylating agent to be used varies depending on the kind of the solvent and other reaction conditions, it is generally about 1 molar equivalent-about 10 molar equivalents, preferably about 1 molar equivalent-about 5 molar equivalents, relative to compound (XIV).

Examples of the base include organic amines (e.g., trimethylamine, triethylamine, diisopropylethylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide etc.), alkali metal hydrides (e.g., potassium hydride, sodium hydride etc.), alkali metal alkoxides (e.g., sodium methoxide, sodium ethoxide, sodium tert-butoxide, potassium tert-butoxide etc.), alkali metal disilazides (e.g., lithium hexamethyldisilazide, sodium hexamethyldisilazide, potassium hexamethyldisilazide etc.) and the like. Of these, organic amines such as triethylamine, diisopropylethylamine, 1,8-diazabicyclo[5.4.0]undec-7-ene and the like and the like are preferable. The amount of the base to be used is generally about 1 molar equivalent-about 100 molar equivalents, preferably about 1 molar equivalent-about 5 molar equivalents, relative to compound (XIV).

Examples of the solvent that does not adversely influence the reaction include hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), carboxylic acids (e.g., acetic acid, trifluoroacetic acid etc.) and the like. These solvents may be used in a mixture at an appropriate ratio.

The reaction temperature is generally about −80° C. to about 200° C., preferably about −80° C. to about 100° C.

The reaction time varies depending on the kind of compound (XIV), reaction temperature and the like, and is generally about 0.1 hr-about 100 hr, preferably about 0.5 hr-about 24 hr.

At the time point the hydroxyl group is activated as mentioned above, compound (XIV) can be used for the next cyclization reaction in the form of a reaction mixture without isolation. In addition, an activated form with an activated hydroxyl group may be isolated and purified by a known separation and purification means, for example, concentration, concentration under reduced pressure, solvent extraction, crystallization, recrystallization, phase transfer, chromatography and the like, and used for the next cyclization reaction.

The cyclization reaction can be carried out by a method known per se, and is generally carried out in the presence of a base, where necessary, in a solvent that does not adversely influence the reaction.

Examples of the base include alkali metal hydrides (e.g., potassium hydride, sodium hydride etc.), inorganic bases (e.g., alkali metal hydroxides such as lithium hydroxide, sodium hydroxide, potassium hydroxide and the like; alkali metal hydrogencarbonates such as sodium hydrogen carbonate, potassium hydrogen carbonate and the like; alkali metal carbonates such as sodium carbonate, potassium carbonate and the like; alkali metal alkoxides such as sodium methoxide, sodium ethoxide and the like etc.), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridazine, 4-dimethylaminopyridine etc.) and the like. Of these, alkali metal hydrides such as sodium hydride and the like are preferable. While the amount of the base to be used varies depending on the kind of the solvent and other reaction conditions, it is generally about 0.1 molar equivalent-about 10 molar equivalents, preferably about 0.1 molar equivalent-about 5 molar equivalents, relative to compound (XIV) before activating a hydroxyl group.

Examples of the solvent that does not adversely influence the reaction include alcohols (e.g., methanol, ethanol, propanol, 2-propanol, butanol, isobutanol, tert-butanol etc.), hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.), water and the like. These solvents may be used in a mixture at an appropriate ratio.

The reaction temperature is generally about −50° C. to about 200° C., preferably about 0° C. to about 150° C.

The reaction time varies depending on the kind of compound (XIV), reaction temperature and the like, and is generally about 0.1 hr-about 100 hr, preferably about 0.5 hr-about 24 hr.

The thus-obtained compound (II) can be isolated and purified by a known separation and purification means, for example, concentration, concentration under reduced pressure, solvent extraction, crystallization, recrystallization, phase transfer, chromatography and the like. In addition, compound (II) may be used for the next reaction without isolation.

Compound (VIII) to be used in the aforementioned method E can also be produced by method G shown below.

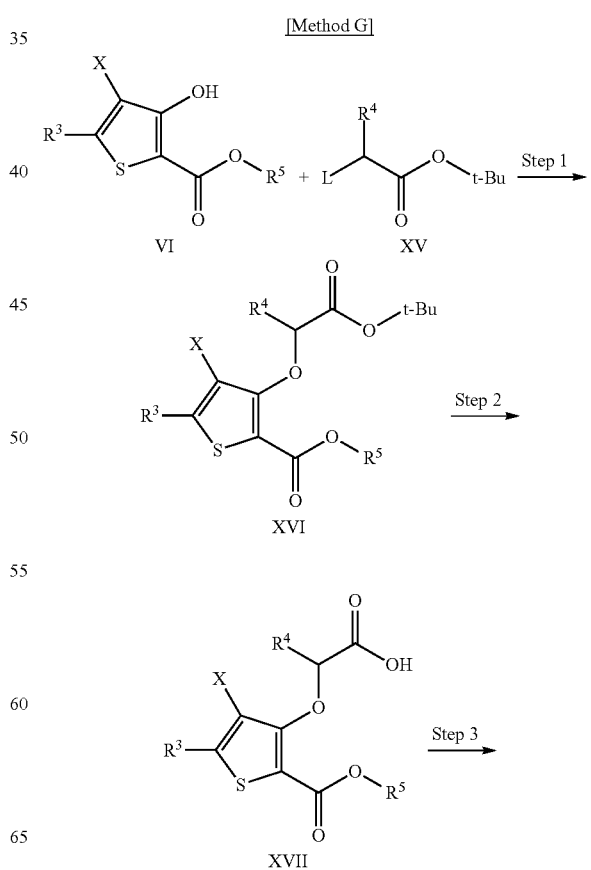

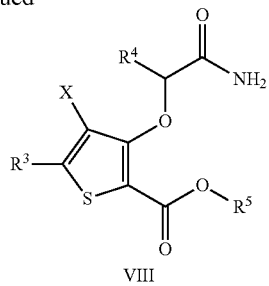

VIII wherein each symbol is as defined above.

step 1

In this step, compound (XVI) is produced by reacting compound (VI) with compound (XV). This reaction can be carried out according to a method known per se and, for example, in the presence of a base in a solvent that does not adversely influence the reaction.

As compound (XV), a commercially available product or one produced by a method known per se may be used directly or after purification. The amount of compound (XV) to be used is generally about 1 molar equivalent-about 5 molar equivalents, preferably about 1 molar equivalent-about 2 molar equivalents, relative to compound (VI).

Examples of the base include alkali metal hydrides (e.g., potassium hydride, sodium hydride etc.), inorganic bases (e.g., alkali metal hydroxides such as lithium hydroxide, sodium hydroxide, potassium hydroxide and the like; alkali metal hydrogencarbonates such as sodium hydrogen carbonate, potassium hydrogen carbonate and the like; alkali metal carbonates such as sodium carbonate, potassium carbonate and the like; alkali metal alkoxides such as sodium methoxide, sodium ethoxide and the like, etc.), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridazine, 4-dimethylaminopyridine etc.) and the like. Of these, alkali metal hydrides such as sodium hydride and the like, inorganic bases such as potassium carbonate and the like are preferable. While the amount of the base to be used varies depending on the kind of the solvent and other reaction conditions, it is generally about 1 molar equivalent-about 10 molar equivalents, preferably about 1 molar equivalent-about 5 molar equivalents, relative to compound (VI).

Examples of the solvent that does not adversely influence the reaction include hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.), water and the like. These solvents may be used in a mixture at an appropriate ratio.

The reaction temperature is generally about −50° C. to about 200° C., preferably about 0° C. to about 150° C.

The reaction time varies depending on the kind of compound (VI), reaction temperature and the like, and is generally about 0.1 hr-about 100 hr, preferably about 0.5 hr-about 24 hr.

step 2

In this step, compound (XVII) is produced by deprotecting compound (XVI). This reaction can be carried out according to a method known per se, for example, in the presence of an acid, where necessary, in a solvent that does not adversely influence the reaction.

Examples of the acid include hydrochloric acid, hydrobromic acid, sulfuric acid, trifluoroacetic acid, trifluoromethanesulfonic acid, hydrogen chloride, methanesulfonic acid and the like.

While the amount of the acid to be used varies depending on the kind of the solvent and other reaction conditions, it is generally about 0.5 molar equivalents-about 500 molar equivalents, preferably about 1 molar equivalent-about 100 molar equivalents, relative to compound (XVI).

Examples of the solvent that does not adversely influence the reaction include hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.) and the like. These solvents may be used in a mixture at an appropriate ratio.

The reaction temperature is generally about −50° C. to about 150° C., preferably about 0° C. to about 80° C.

The reaction time varies depending on the kind of compound (XVI), reaction temperature and the like, and is generally about 0.1 hr-about 100 hr, preferably about 0.5 hr-about 24 hr.

step 3

In this step, compound (VIII) is produced by subjecting compound (XVII) to an amidation reaction. This reaction can be carried out according to a method known per se. Examples thereof include a method including directly reacting compound (XVII) with ammonia using a condensing agent and a method including reacting a reactive derivative of compound (XVII) with ammonia.

Examples of the condensing agent include carbodiimide system condensation reagents such as dicyclohexylcarbodiimide (DCC), diisopropylcarbodiimide (DIPC), 1-ethyl-3-(3-dimethylaminopropyl)carbodiimide (EDC) and hydrochloride thereof and the like; phosphoric acid system condensation reagents such as diethyl cyanophosphate, diphenylphosphoryl azide and the like; carbonyldiimidazole, 2-chloro-1,3-dimethylimidazolium tetrafluoroborate, O-(7-azabenzotriazol-1-yl)-1,1,3,3-tetramethyluronium hexafluorophosphate (HATU) and the like.

Examples of the solvent to be used for the reaction using a condensing agent include amides such as N,N-dimethylformamide, N,N-dimethylacetamide, N-methylpyrrolidone and the like; sulfoxides such as dimethyl sulfoxide and the like; halogenated hydrocarbons such as chloroform, dichloromethane and the like; aromatic hydrocarbons such as benzene, toluene and the like; ethers such as tetrahydrofuran, dioxane, diethyl ether, dimethoxyethane and the like; esters such as methyl acetate, ethyl acetate and the like; nitriles such as acetonitrile, propionitrile and the like; water and the like. These solvents may be used in a mixture at an appropriate ratio.

The amount of the ammonia to be used is generally about 1% molar equivalent-about 50 molar equivalents, preferably about 1 molar equivalent-about 5 molar equivalents, relative to compound (XVII).

The amount of the condensing agent to be used is generally about 1 molar equivalent-about 50 molar equivalents, preferably about 1 molar equivalent-about 5 molar equivalents, relative to compound (XVII).

When a carbodiimide system condensation reagent is used as a condensing agent, the reaction efficiency can be improved by using a suitable condensation promoter (e.g., 1-hydroxy-7-azabenzotriazole, 1-hydroxybenzotriazole, N-hydroxysuccinimide, N-hydroxyphthalimide and the like) where necessary. In addition, when HATU or a phosphoric acid system condensation reagent is used as condensing agents, the reaction efficiency can be improved by using an organic amine base such as triethylamine, N,N-diisopropylethylamine and the like.

The amount of the above-mentioned condensation promoter and organic amine base to be used is generally about 1 molar equivalent-about 50 molar equivalents, preferably about 1 molar equivalent-about 5 molar equivalents, relative to compound (XVII).

In addition, when 1-hydroxybenzotriazole is used as a condensation promoter, 1H-benzotriazol-1-ol 1 ammonium salt may be used as a substitute of 1-hydroxybenzotriazole and ammonia.

The reaction temperature is generally −30° C. to 120° C., preferably −10° C. to 100° C.

The reaction time is generally 0.5-60 hr.

As the reactive derivative, those exemplified for method F, step 2, and the like are generally used, and they can be produced by a method known per se. In the reaction of a reactive derivative and ammonia, the reactive derivative is reacted with ammonia in a solvent that does not adversely influence the reaction where necessary in the presence of a base (e.g., triethylamine, N,N-diisopropylethylamine) where necessary.

The amount of the ammonia to be used is generally about 1 molar equivalent-about 50 molar equivalents, preferably about 1 molar equivalent-about 5 molar equivalents, relative to compound (XVII).

Examples of the solvent that does not adversely influence the reaction include amides such as N,N-dimethylformamide, N,N-dimethylacetamide, N-methylpyrrolidone and the like; sulfoxides such as dimethyl sulfoxide and the like; halogenated hydrocarbons such as chloroform, dichloromethane and the like; aromatic hydrocarbons such as benzene, toluene and the like; ethers such as tetrahydrofuran, dioxane, diethyl ether, dimethoxyethane and the like; esters such as methyl acetate, ethyl acetate and the like; nitriles such as acetonitrile, propionitrile and the like; water and the like. These solvents may be used in a mixture at an appropriate ratio.

The reaction temperature is generally −30° C. to 120° C., preferably −10 to 100° C.

The reaction time is generally 0.5-60 hr.

Compound (I) can be isolated and purified by a known means, for example, phase transfer, concentration, solvent extraction, fractionation, liquid conversion, crystallization, recrystallization, chromatography and the like. When compound (1) is obtained as a free compound, the compound can be converted to an objective salt according to a method known per se or a method analogous thereto. Conversely, when it is obtained as a salt, the salt can be converted to a free form or other objective salt by a method known per se or a method analogous thereto.

When compound (I) contains an isomer such as an optical isomer, a stereoisomer, a regioisomer, a rotamer or the like, any one isomer and mixtures thereof are also encompassed in compound (I). When an isomer due to conformation is present, such isomer and a mixture thereof are also encompassed in compound (I) of the present invention. These isomers are also encompassed in compound (I) and compound (I'), and can be obtained as a single product according to synthesis methods or separation methods known per se (e.g., concentration, solvent extraction, column chromatography, recrystallization, etc.). For example, when compound (I) has an optical isomer, an optical isomer resolved from this compound is also encompassed in compound (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) a Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method, etc.) and the like, and is subjected to a chemical treatment such as hydrolysis and the like to separate an optically active reagent moiety, whereby an optical isomer is obtained. For example, when compound (I) contains a hydroxyl group, or primary or secondary amino group(s) in a molecule, the compound and an optically active organic acid (e.g., MTPA [α-methoxy-α-(trifluoromethyl) phenylacetic acid], (−)-menthoxyacetic acid etc.) and the like are subjected to condensation reaction to give diastereomers in the ester form or in the amide form, respectively. When compound (I) has a carboxyl group in molecule, this compound and an optically active amine or an optically active alcohol are subjected to condensation reaction to give diastereomers in the amide form or in the ester form, respectively. The separated diastereomer is converted to an optical isomer of the original compound by acid hydrolysis or base hydrolysis.

Compound (I) may be a crystal, and both a single crystal and a crystal mixture are encompassed in compound (I).

The crystal of compound (I) can be produced by crystallization of compound (I) according to crystallization methods known per se.

Examples of the crystallization method include a method of crystallization from a solution, a method of crystallization from vapor, a method of crystallization from the melts and the like.

The crystal of compound (I) may be a pharmaceutically acceptable cocrystal or cocrystal salt. Here, the cocrystal or cocrystal salt means a crystalline substance consisting of, at room temperature, two or more (unique, distinct, special?) solids each having different physical properties (e.g., structure, melting point, melting heat, hygroscopicity, solubility, stability etc.). The cocrystal or cocrystal salt can be produced according to a cocrystallization method known per se.

The "method of crystallization from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrotheuual growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, isopropyl alcohol, etc.), water and the like. These solvents are used alone or in a combination of two or more at a suitable ratio (e.g., 1:1 to 1:100 (a volume ratio)). Where necessary, a seed crystal can be used.

The "method of crystallization from vapor" is, for example, a vaporization method (a sealed tube method, a gas stream method), a gas phase reaction method, a chemical transportation method and the like.

The "method of crystallization from the melts" is, for example, a normal freezing method (a Czockralski method, a temperature gradient method and a Bridgman method, etc.), a zone melting method (a zone leveling method and a floating zone method, etc.), a special growth method (a VLS method and a liquid phase epitaxy method, etc.) and the like.

Preferable examples of the crystallization method include a method of dissolving compound (I) in a suitable solvent (e.g., alcohols such as methanol, ethanol, etc., and the like) at a temperature of 20 to 120° C., and cooling the resulting solution to a temperature not higher than the temperature of dissolution (e.g., 0 to 50° C., preferably 0 to 20° C.) and the like.

The thus obtained crystals of compound (I) of the present invention can be isolated, for example, by filtration and the like.

An analysis method of the obtained crystal is generally a method of crystal analysis by powder X-ray diffraction. As a method of determining crystal orientation, a mechanical method, an optical method or the like can also be used.

The crystal of compound (I) obtained by the above-mentioned production method (hereinafter to be abbreviated as "the crystal of the present invention") has high purity, high quality, and low hygroscopicity, is not denatured even after a long-term preservation under general conditions, and is extremely superior in the stability. In addition, it is also superior in the biological properties (e.g., pharmacokinetics (absorption, distribution, metabolism, excretion), efficacy expression etc.) and is extremely useful as a medicament.

In the present specification, the melting point means a melting point measured using, for example, a micro melting point apparatus (YANACO, MP-500D), a DSC (differential scanning calorimetry) apparatus (SEIKO, EXSTAR6000) and the like.

Compound (I) may be also used as a prodrug. A prodrug of compound (I) means a compound which is converted to compound (I) with a reaction due to an enzyme, an gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug of compound (I) may be a compound obtained by subjecting an amino in compound (I) to an acylation, alkylation or phosphorylation [e.g., a compound obtained by subjecting an amino in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, etc.]; a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxy group in compound (I) to an esterification or amidation [e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, methylamidation, etc.] and the like. Any of these compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

Compound (I) or a prodrug thereof (hereinafter to be sometimes abbreviated as the compound of the present invention) has a superior serotonin 5-$HT_{2C}$ receptor activating action.

In addition, the compound of the present invention is useful as a medicament since it shows superior oral absorbability, low toxicity and safety.

Accordingly, compound (I) of the present invention having a superior serotonin 5-$HT_{2C}$ receptor activating action is useful for the improvement, prophylaxis or treatment of all serotonin 5-$HT_{2C}$ associated diseases in mammals (e.g., mouse, rat, hamster, rabbit, cat, dog, bovine, sheep, monkey, human and the like), for example, (1) Lower Urinary Tract Symptoms:

for example, overactive bladder, benign prostatic hyperplasia, interstitial cystitis, chronic prostatitis, storage symptom (e.g., day time urinary frequency, nocturia, urinary urgency, urinary incontinence, stress urinary incontinence, urge urinary incontinence, mixed urinary incontinence, enuresis, nocturnal enuresis, overflow urinary incontinence, other urinary incontinence, enhanced, decreased or missing bladder sensation etc.), voiding symptom (e.g., weak urinary stream, split urinary stream, spraying stream, intermittent urinary stream, voiding postponement, straining at urination, terminal dribbling etc.), post-micturition symptom (e.g., sense of residual urine, post-micturition dribble etc.), symptom due to sexual intercourse (e.g., coital pain, vaginal dryness, urinary incontinence etc.), symptom due to pelvic organ prolapse (e.g., foreign body sensation, lumbago etc.), genital organ pain or lower urinary tract pain (e.g., bladder pain, urethral pain, pudendalgia, vaginodynia, scrotal pain, perineal pain, pelvic pain etc.), genital organ or urinary tract pain syndrome (e.g., bladder pain syndrome, urethral pain syndrome, pudendalgia syndrome, vaginal syndrome, scrotal pain syndrome, perineal pain syndrome, pelvic pain syndrome etc.), symptom syndrome suggesting lower urinary tract dysfunction (e.g., overactive bladder syndrome, a lower urinary tract symptom suggesting bladder outlet obstruction etc.), polyuria, urolithiasis (e.g., ureteral calculus, urethral calculus);

(2) Metabolic Diseases:

for example, diabetes (insulin dependent diabetes, diabetic complications, diabetic retinopathy, diabetic microangiopathy, diabetic neuropathy etc.), impaired glucose tolerance, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity], benign prostatic hyperplasia, sexual dysfunction;

(3) Central Nervous System Diseases:

for example, neurodegenerative diseases (e.g., Alzheimer's disease, Down's disease, Parkinson's disease, Creutzfeldt-Jakob disease, amyotrophic lateral sclerosis (ALS), Huntington chorea, diabetic neuropathy, multiple sclerosis etc.), mental diseases (e.g., schizophrenia, depression, mania, anxiety neurosis, obsessive-compulsive neurosis, panic disorder, epilepsy, alcohol dependence, drug dependence, anxiety, anxious mental state, emotional abnormality, cyclothymia, nervous erethism, autism, faint, addiction, low sex drive etc.), disorders such as central nervous system and peripheral nerve disorders (e.g., head trauma, spinal damage, brain edema, disorders of sensory function, abnormality of sensory function, disorders of autonomic nervous function, abnormality of autonomic nervous function, whiplash injury etc.), memory disorders (e.g., senile dementia, amnesia, cerebrovascular dementia etc.), cerebrovascular disorders (e.g., cerebral hemorrhage, cerebral infarction and the like and sequelae or complication thereof, asymptomatic cerebrovascular accident, transient cerebral ischemic attack, hypertensive encephalopathia, blood-brain barrier disorder, etc.), recurrence and sequelae of cerebrovascular disorders (e.g., neural symptoms, mental symptoms, subjective symptoms, disorders of daily living activities etc.), central nervous system hypofunction after brain blood vessel occlusion, disorder or abnormality of autoregulation ability of brain circulation or renal circulation, sleep disorder;

(4) Genital Insufficiency Diseases:

for example, male erectile dysfunction, dyssperma, female genital insufficiency;

(5) Digestive Organ Diseases:

for example, an irritable bowel syndrome, inflammatory bowel disease, ulcerative colitis, Crohn's disease, diseases caused by a spiral urease-positive gram-negative bacterium (e.g., *Helicobacter pylori*, etc.) (e.g., gastritis, gastric ulcer, etc.), gastric cancer, postgastrostomy disorder, indigestion, esophageal ulcer, pancreatitis, polyp of the colon, cholelithiasis, hemorrhoids, peptic ulcer, situational ileitis, gluttony, constipation, diarrhea, borborygmus;

(6) Inflammatory or Allergic Diseases:

for example, allergic rhinitis, conjunctivitis, gastrointestinal allergy, pollinosis, anaphylaxis, dermatitis, herpes, psoriasis, bronchitis, expectoration, retinopathy, postoperative and posttraumatic inflammation, regression of puffiness, pharyngitis, cystitis, meningitides, inflammatory ocular disease;

(7) Osteoarthropathy Diseases:

for example, rheumatoid arthritis (e.g., chronic rheumatoid arthritis), arthritis deformans, rheumatoid myelitis, osteoporosis, abnormal growth of cells etc., bone fracture, bone refracture, osteomalacia, osteopenia, Paget's disease of bone, rigid myelitis, articular tissue destruction by gonarthrosis deformans and similar diseases thereto;

(8) respiratory diseases:

for example, cold syndrome, pneumonia, asthma, pulmonary hypertension, pulmonary thrombi/pulmonary obliteration, pulmonary sarcoidosis, pulmonary tuberculosis, interstitial pneumonia, silicosis, adult respiratory distress syndrome, chronic obstructive pulmonary disease, cough;

(9) infectious diseases:

for example, HIV infectious diseases, virus infectious diseases due to cytomegalo virus, influenza virus, herpes virus and the like, *rickettsia* infectious diseases, bacterial infectious diseases, sexually-transmitted diseases, *carinii pneumonia, Helicobacter pylori* infectious disease, systemic fungal infectious diseases, tuberculosis, invasive staphylococcal infectious diseases, acute viral encephalitis, acute bacterial meningitides, AIDS encephalitis, septicemia, sepsis, sepsis gravis, septic shock, endotoxin shock, toxic shock syndromes;

(10) cancers:

for example, primary, metastatic or recurrent breast cancer, prostatic cancer, pancreatic cancer, gastric cancer, lung cancer, large bowel cancer (e.g., colorectal cancer, rectal cancer, anal cancer), esophagus cancer, duodenal cancer, head and neck cancer (e.g., cancer of the tongue, pharynx cancer, laryngeal cancer), brain tumor, schwannoma, non-small cell lung cancer, small cell lung cancer, liver cancer, kidney cancer, biliary tract cancer, uterine cancer (e.g., uterine body cancer, cervical cancer), ovarian cancer, urinary bladder cancer, skin cancer, hemangioma, malignant lymphoma, malignant melanoma, thyroid cancer, bone tumor, hemangioma, vascular fibroma, retinosarcoma, penile cancer, solid cancer in childhood, Kaposi's sarcoma, Kaposi's sarcoma caused by AIDS, maxillary tumor, fibrous histiocytoma, leiomyosarcoma, rhabdomyosarcoma, liposarcoma, fibroid tumors of the uterus, osteoblastoma, osteosarcoma, chondrosarcoma, cancerous mesothelioma, tumors such as leukemia, Hodgkin's disease;

(11) circulatory diseases:

for example, acute coronary artery syndromes (e.g., acute myocardial infarction, unstable angina, etc.), peripheral arterial occlusion, Raynaud's disease, Buerger's disease, restenosis after coronary-artery intervention (e.g., percutaneous transluminal coronary angioplasty (PTCA), directional coronary atherectomy (DCA), stenting, etc.), restenosis after coronary-artery bypass operation, restenosis after intervention (e.g., angioplasty, atherectomy, stenting, etc.) or bypass operation in other peripheral artery, ischemic cardiac diseases (e.g., myocardial infarction, angina, etc.), myocarditis, intermittent claudication, lacunar infarction, arteriosclerosis (e.g., atherosclerosis, etc.), cardiac failure (acute cardiac failure, chronic cardiac failure including congestive cardiac failure), arrhythmia, progress of atherosclerotic plaque, thrombosis, hypertension, hypertensive tinnitus, hypotension;

(12) pains:

for example, headache, migraine, neuralgia, pelvic organ pain (including bladder pain);

(13) autoimmune diseases:

for example, collagen disease, systemic lupus erythematosus, scleroderma, polyarteritis, myasthenia gravis, multiple sclerosis, Sjogren's syndrome, Behcet's disease;

(14) hepatic diseases:

for example, hepatitis (including chronic hepatitis), cirrhosis, interstitial hepatic diseases;

(15) pancreatic diseases:
for example, pancreatitis (including chronic pancreatitis);
(16) renal diseases:
for example, nephritis, glomerulonephritis, glomerulosclerosis, renal failure, thrombotic microangiopathy, dialysis complications, organ disorders including nephropathia by radiation, diabetic nephropathy;
(17) endocrine diseases:
for example, Addison's disease, Cushing's syndrome, melanocytoma, primary aldosteronism and the like;
(18) gynecologic diseases:
for example, organ prolapse (e.g., pelvic organ prolapse, genital prolapse, uterine prolapse, bladder prolapse, rectal prolapse, urethral prolapse, urethral hypermobility, enterocele, rectocele, cystocele, laceration of perineal body, pelvic floor hernia etc.), climacteric disorder, gestational toxicosis, endometriosis, hysteromyoma, ovarian disease, mammary disease, premenstrual syndrome and the like;
(19) other diseases:
for example,
(a) transplant rejection [e.g., posttransplantational rejection, posttransplantational polycythemia, hypertension, organ disorder and/or vascular hypertrophy, graft-versus-host disease],
(b) abnormality in characteristic of blood and/or blood components [e.g., enhancement in platelet aggregation, abnormality of erythrocyte deformability, enhancement in leukocyte adhesiveness, increase in blood viscosity, polycythemia, vascular peliosis, autoimmune hemolytic anemia, disseminated intravascular coagulation syndrome (DIC), multiple myelopathy],
(c) dermatic diseases (e.g., keloid, hemangioma, psoriasis, pruritus),
(d) ophthalmic diseases (e.g., glaucoma, ocular hypertension disease),
(e) otolaryngological diseases (e.g., Menuel syndrome, tinnitus, gustation disorder, dizziness, disequilibrium, dysphagia),
(f) diseases due to environmental and/or occupational factors (e.g., radiation disorder, disorders by ultraviolet ray/infrared ray/laser ray, altitude sickness),
(g) ataxia, stiffness, tremor, movement disorder, akinesia,
(h) chronic fatigue syndrome,
(i) sudden infant death syndrome,
(j) hiccup,
(k) diseases causing palpitation, vertigo, heartburn etc.

The compound of the present invention is particularly useful as a serotonin 5-$HT_2$ receptor activator, a drug for the improvement, prophylaxis or treatment of lower urinary tract symptoms, a drug for the prophylaxis or treatment of obesity, or a drug for the prophylaxis or treatment of organ prolapse. When the lower urinary tract symptom is a target disease, the compound of the present invention is particularly useful as a drug for the improvement, prophylaxis or treatment of stress urinary incontinence.

A medicament containing the compound of the present invention (hereinafter to be abbreviated as "the medicament of the present invention") may be any form of a solid preparation such as powder, granule, tablet, capsule, orally disintegrable film and the like, or a liquid agent such as syrup, emulsion, injection and the like.

The medicament of the present invention can be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the agent of the present invention may be formed into a sustained-release preparation containing an active ingredient and a biodegradable polymer compound. The sustained-release preparation can be produced according to the method described in JP-A-9-263545.

In the medicament of the present invention, the content of the compound of the present invention varies depending on the forms of the preparations, but is generally in the order of 0.01 to 100% by weight, preferably 0.1 to 50% by weight, more preferably 0.5 to 20% by weight, relative to the total weight of each preparation.

The medicament of the present invention can be produced by using the compound of the present invention alone or in admixture with a suitable, pharmacologically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by a conventional method, and processing the mixture into a dosage form of tablets (including sugar-coated tablet, film-coated tablet, sublingual tablet, orally disintegrating tablet, buccal tablet and the like), pill, powder, granule, capsules (including soft capsule, microcapsule), troche, syrup, liquid, emulsion, suspension, controlled-release preparations (e.g., immediate-release preparation, sustained-release preparation, sustained-release microcapsule), aerosol, films (e.g., orally disintegrable film, oral mucosal patch film), injections (e.g., subcutaneous injection, intravenous injection, intramuscular injection, intraperitoneal injection), drip infusion, transdermal absorption type preparation, ointment, lotion, adhesive preparation, suppositories (e.g., rectal suppository, vaginal suppository), pellet, nasal preparations, pulmonary preparations (inhalant) or eye drop. The medicament of the present invention can be safely administered orally or parenterally (e.g., intravenous, intramuscular, subcutaneous, intraorgan, intranasal, intradermal, instillation, intracerebral, intrarectal, vaginal, intraperitoneal, and direct administration to lesion).

When the compound of the present invention is formed as a preparation for topical administration, it can also be directly administered to the affected part of an articular disease. In this case, an injection is preferable. The compound of the present invention can also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, the compound of the present invention is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension can be obtained by dispersing the compound of the present invention together with vegetable oil such as sesame oil, corn oil and the like or a mixture thereof with a phospholipid such as lecithin and the like, or medium-chain triglyceride (e.g., miglyol 812 etc.) to give an injection to be actually used.

While the does of the compound of the present invention varies depending on the kind of the compound of the present invention or a pharmaceutically acceptable salt thereof, administration route, symptom, age of the subject animal of administration (e.g., mammals such as human, rat, mouse, cat, dog, rabbit, bovine, pig and the like), and the like, it is, for example, about 0.005-50 mg, preferably about 0.05-10 mg, more preferably about 0.2-4 mg, as the compound of the present invention per kg body weight/day, for oral administration to an adult patient with stress urinary incontinence, obesity and/or pelvic organ prolapse, which can be administered in about one to three divided portions.

The compound of the present invention can be used along with other pharmaceutical composition.

As a drug that can be blended or combined with the compound of the present invention (hereinafter to be abbreviated as concomitant drug), the following drugs and the like can be used.

(1) Other Drugs for Treating Stress Urinary Incontinence

For example, adrenaline α1 receptor agonists (e.g., ephedrine hydrochloride, midodrine hydrochloride), adrenaline β2 receptor agonists (e.g., Clenbuterol), noradrenaline uptake inhibitory substances, noradrenaline and serotonin uptake inhibitory substances (e.g., duloxetine), tricyclic antidepressants (e.g., imipramine hydrochloride), anticholinergic agents or smooth muscle stimulants (e.g., oxybutynin hydrochloride, propiverine hydrochloride, celimeverine hydrochloride), female hormone drugs (e.g., conjugated estrogen (premarin), estriol).

(2) Agent for Treating Diabetes

For example, insulin preparations [e.g., animal insulin preparations extracted from the bovine or swine pancreas; human insulin preparations synthesized by a genetic engineering technique using *Escherichia coli* or a yeast; insulin zinc; protamine zinc insulin; a fragment or a derivative of insulin (e.g., INS-1, etc.), and the like], insulin sensitizers (e.g., pioglitazone hydrochloride, troglitazone, rosiglitazone or its maleate, JTT-501, MCC-555, YM-440, GI-262570, KRP-297, FK-614, CS-011, etc.), α-glucosidase inhibitors (e.g., voglibose, acarbose, miglitol, emiglitate, etc.), biguanides (e.g., phenformin, metformin, buformin, etc.), sulfonylureas (e.g., tolbutamide, glibenclamide, gliclazide, chlorpropamide, tolazamide, acetohexamide, glyclopyramide, glimepiride, etc.) and other insulin secretagogues (e.g., repaglinide, senaglinide, mitiglinide or its calcium salt hydrate, GLP-1, nateglinide, etc.), dipeptidylpeptidase IV inhibitors (e.g., vildagliptin, sitagliptin, saxagliptin, alogliptin, NVP-DPP-728, PT-100, P32/98, etc.), β3 agonists (e.g., CL-316243, SR-58611-A, UL-TG-307, AJ-9677, AZ40140, etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLT (sodium-glucose cotransporter) inhibitors (e.g., T-1095, etc.).

(3) Agent for Treating Diabetic Complications

For example, aldose reductase inhibitors (e.g., tolrestat, epalrestat, zenarestat, zopolrestat, fidarestat (SNK-860), minalrestat (ARI-509), CT-112, etc.), neurotrophic factors (e.g., NGF, NT-3, etc.), AGE inhibitors (e.g., ALT-945, pimagedine, pyratoxathine, N-phenacylthiazolium bromide (ALT-766), EXO-226, etc.), active oxygen scavengers (e.g., thioctic acid, etc.), cerebral vasodilators (e.g., tiapride, etc.).

(4) Antihyperlipidemic Agent

For example, statin compounds inhibiting cholesterol synthesis (e.g., pravastatin, simvastatin, lovastatin, atorvastatin, fluvastatin, cerivastatin or their salt (e.g., sodium salt, etc.), etc.), squalene synthase inhibitors, fibrate compounds having triglyceride lowering action (e.g., bezafibrate, clofibrate, simfibrate, clinofibrate, etc.).

(5) Hypotensive Agent

For example, angiotensin converting enzyme inhibitors (e.g., captopril, enalapril, delapril, etc.), angiotensin II antagonists (e.g., losartan, candesartan cilexetil, etc.), calcium antagonists (e.g., manidipine, nifedipine, amlodipine, efonidipine, nicardipine, etc.), clonidine.

(6) Antiobesity Agent

For example, antiobesity drugs acting on the central nervous system (e.g. dexfenfluramine, fenfluramine, phentermine, sibutramine, anfepramone, dexamphetamine, mazindol, phenylpropanolamine, clobenzorex, etc.), pancreatic lipase inhibitors (e.g. orlistat, etc.), β3 agonists (e.g. CL-316243, SR-58611-A, UL-TG-307, AJ-9677, AZ40140, etc.), anorectic peptides (e.g. leptin, CNTF (Ciliary Neurotrophic Factor), etc.), cholecystokinin agonists (e.g. lintitript, FPL-15849, etc.).

(7) Diuretic Agent

For example, xanthine derivatives (e.g., theobromine sodium salicylate, theobromine calcium salicylate, etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), antialdosterone preparations (e.g., is spironolactone, triamterene, etc.), carbonic anhydrase inhibitors (e.g., acetazolamide, etc.), chlorobenzenesulfonamide preparations (e.g., chlorthalidone, mefruside, indapamide, etc.), azosemide, isosorbide, ethacrynic acid, piretanide, bumetanide, furosemide.

(8) Chemotherapeutic Agent

For example, alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, taxol, etc.), cisplatin, carboplatin, etoposide, etc. Among these, 5-fluorouracil derivatives such as Furtulon and Neo-Furtulon are preferred.

(9) Immunotherapeutic Agent

For example, microorganism- or bacterium-derived components (e.g., muramyl dipeptide derivatives, Picibanil, etc.), immunopotentiator polysaccharides (e.g., lentinan, schizophyllan, krestin, etc.), genetically engineered cytokines (e.g., interferons, interleukins (IL), etc.), colony stimulating factors (e.g., granulocyte colony stimulating factor, erythropoietin, etc.) and the like. Among these, IL-1, IL-2 and IL-12 are preferred.

(10) Agent Recognized to Ameliorate Cachexia in Animal Models or Clinical Practice For example, progesterone derivatives (e.g., megestrol acetate) [Journal of Clinical Oncology, vol. 12, pp. 213-225, 1994], metoclopramide agents, tetrahydrocannabinol agents (the above references are applied to both), fat metabolism ameliorating drugs (e.g., eicosapentaenoic acid etc.) [British Journal of Cancer, vol. 68, pp. 314-318, 1993], growth hoiiuones, IGF-1, and antibodies to the cachexia-inducing factors such as TNF-α, LIF, IL-6 and oncostatin M.

(11) Antiinflammatory Agent

For example, steroids (e.g., dexamethasone, etc.), sodium hyaluronate, cyclooxygenase inhibitors (e.g., indomethacin, ketoprofen, loxoprofen, meloxicam, ampiroxicam, celecoxib, rofecoxib, etc.).

(12) Miscellaneous

For example, glycosylation inhibitors (e.g., ALT-711, etc.), nerve regeneration promoting drugs (e.g., Y-128, VX853, prosaptide, etc.), drugs acting on the central nervous system (e.g., antidepressants such as desipramine, amitriptyline, imipramine, fluoxetine, paroxetine, doxepin, etc.), anticonvulsants (e.g., lamotrigine, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), indoleamine uptake inhibitors (e.g., fluoxetine, paroxetine), narcotic analgesics (e.g., morphine), GABA receptor agonists (e.g., gabapentin), GABA uptake inhibitors (e.g., tiagabine), $\alpha_2$ receptor agonists (e.g., clonidine), local analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatriptan), serotonin receptor antagonists (e.g., cyproheptadine hydrochloride, ondansetron), serotonin uptake inhibitors (e.g., fluvoxamine maleate, fluoxetine, paroxetine), hypnotics (e.g., triazolam, zolpidem), anticholinergic agents, $\alpha_1$ receptor blocking agents (e.g., tamsulosin, silodosin, naftopidil), muscle relaxants (e.g., baclofen), potassium channel openers (e.g., nicorandil), calcium channel blocking agents (e.g., nifedipine), agents for preventing and/or treating Alzheimer's disease (e.g., donepezil, rivastigmine, galanthamine), agents for treating Parkinson's disease (e.g., L-dopa), agents for preventing and/or treating multiple sclerosis (e.g., interferon $\beta$-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonists (e.g., piperidine derivatives (GR159897, GR149861, SR48968 (saredutant), SR144190, YM35375, YM38336, ZD7944, L-743986, MDL105212A, ZD6021, MDL105172A, SCH205528, SCH62373, R-113281 etc.), perhydroisoindole derivatives (e.g., RPR-106145 etc.), quinoline derivatives (e.g., SB-414240 etc.), pyrrolopyrimidine derivatives (e.g., ZM-253270 etc.), pseudopeptide derivatives (e.g., MEN11420 (nepadutant), SCH217048, L-659877, PD-147714 (CAM-2291), MEN10376, 516474 etc.), others (GR100679, DNK333, GR94800, UK-224671, MEN10376, MEN10627), or a salt thereof etc.), agents for treating HIV infection (saquinavir, zidovudine, lamivudine, nevirapine), agents for treating chronic obstructive pulmonary diseases (salmeterol, thiotropium bromide, cilomilast).

Anticholinergic agents include, for example, atropine, scopolamine, homatropine, tropicamide, cyclopentolate, butylscopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrogen bromide, homatropine hydrogen bromide, cyclopentolate hydrochloride, flavoxate hydrochloride, pirenzepine hydrochloride, trihexyphenidyl hydrochloride, oxybutynin hydrochloride, tolterodine tartrate, etc.), and the like, preferably, oxybutynin, propiverine, darifenacin, tolterodine, temiverine, trospium chloride or a salt thereof (e.g., oxybutynin hydrochloride, tolterodine tartrate, etc.). In addition, acetylcholinesterase inhibitors (e.g., distigmine, etc.) and the like can be used.

As the noradrenaline uptake inhibitor, for example, Betanidine, Tesofensine, Trodusquemihe, PSN-602 and the like can be used. In addition, as the noradrenaline and serotonine uptake inhibitor, duloxetine, Venlafaxine and the like can be used.

In combination of the compound of the present invention and the concomitant drug, the administration time of the compound of the present invention and the concomitant drug is not restricted, and the compound of the present invention or a pharmaceutical composition thereof and the concomitant drug or a pharmaceutical composition thereof can be administered to the administration subject simultaneously, or may be administered at different times. The dosage of the concomitant drug may be determined according to the dose clinically used, and can be appropriately selected depending on the administration subject, administration route, disease, combination and the like.

The concomitant administration mode is not particularly restricted, and it is sufficient that the compound of the present invention and the concomitant drug are combined in administration. Examples of such administration mode include the following methods:

(1) The compound of the present invention and the concomitant drug are simultaneously produced to give a single preparation which is administered, (2) The compound of the present invention and the concomitant drug are separately produced to give two kinds of preparations which are administered simultaneously by the same administration route, (3) The compound of the present invention and the concomitant drug are separately produced to give two kinds of preparations which are administered by the same administration route at different times, (4) The compound of the present invention and the concomitant drug are separately produced to give two kinds of preparations which are administered simultaneously by different administration routes, (5) The compound of the present invention and the concomitant drug are separately produced to give two kinds of preparations which are administered by different administration routes at different times (e.g., after administering the compound of the present invention, the concomitant drug are administered in this order, or in the reverse order), and the like.

In the medicament using the compound of the present invention and a concomitant drug in combination (hereinafter to be abbreviated as "the combination drug of the present invention"), the mixing ratio of compound of the present invention and a concomitant drug can be appropriately determined according to the subject of administration, administration route, disease and the like.

For example, while the content of compound of the present invention in the combination drug of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the concomitant drug in the combination drug of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the additive such as a carrier and the like in the combination drug of the present invention varies depending on the form of the preparation, it is generally about 1 to about 99.99 wt %, preferably about 10 to about 90 wt %, relative to the whole preparation.

Similar contents can be employed when the compound of the present invention and the concomitant drug are independently formulated.

When the combination drug of the present invention is a sustained-release preparation, the dose varies depending on the kind and content of the compound of the present invention, dosage form, period of sustained drug release, subject animal of administration (e.g., mammals such as human, rat, mouse, cat, dog, rabbit, bovine, swine and the like) and administration object. For parenteral administration, for example, about 0.1 to about 100 mg of the compound of the present invention only needs to be released in one week from the administered preparation.

The dose of the concomitant drug may be set within the range such that it causes no problems of side effects. The daily dose as the concomitant drug varies depending on severity of symptoms, age, sex, weight and sensitivity of the subject to be administered, time and interval of administration, property, formulation and kinds of pharmaceutical preparation, kinds of active ingredients, etc., and is not particularly limited. In the case of oral administration, a daily dosage in terms of drugs is usually in the order of about 0.001 to 2000 mg, preferably about 0.01 to 500 mg, and more preferably about 0.1 to 100 mg, per 1 kg body weight of mammals, which may be administered once a day or in two to four divided portions a day.

When the combination drug of the present invention is administered, the compound of the present invention and the concomitant drug may be administered simultaneously or in a staggered manner. In the case of staggered administration, the time interval varies depending on the active ingredients to be administered, a formulation and an administration route. For example, when the concomitant drug is administered first, the compound of the present invention may be administered 1 minute to 3 days, preferably 10 minutes to 1 day, more preferably 15 minutes to 1 hour after administering the concomitant drug. When the compound of the present invention is administered first, the concomitant drug may be administered 1 minute to 1 day, preferably 10 minutes to 6 hours, more preferably 15 minutes to 1 hour after administering the compound of the present invention.

The medicament of the present invention shows low toxicity and can be used safely. Particularly, since the Example compounds shown below are superior in the absorption by oral administration, they can be advantageously used for oral preparations.

EXAMPLES

The present invention is further described in detail with reference to Examples, Formulation Examples and Experimental Examples which are not intended to restrict the invention and may be modified without departing from the scope of the invention.

In Examples, column chromatography was performed using Purif-8 or Purif-α2 manufactured by MORITEX and under observation by a UV detector. As silica gel for column chromatography, Purif-Pack manufactured by MORITEX was used. The room temperature referred herein means temperature generally from about 10° C. to 30° C.

The abbreviations in Examples mean the following.
LC: liquid chromatography
ESI-MS: electrospray ionization mass spectrometry
m/z: molecular ion peak
NMR: nuclear magnetic resonance spectrum
Hz: hertz
J: coupling constant
m: multiplet
q: quartet
t: triplet
d: doublet
dd: double doublet
s: singlet
dt: double triplet
brs: broad singlet
Boc: tert-butyloxycarbonyl group
N: normal concentration
DME: dimethoxyethane
DMF: N,N-dimethylfo.uuamide
DMSO: dimethyl sulfoxide
EtOH: ethanol
$Et_2O$: diethyl ether
MeOH: methanol
THF: tetrahydrofuran
$(Boc)_2O$: di-tert-butyl bicarbonate LC-MS in Examples was measured under the following conditions.
Analysis by LC-MS
measurement device: Waters LC-MS system
HPLC: Agilent HP1100
MS: Micromass ZQ
HPLC conditions
column: CAPCELL PAK C18UG120, S-3 μM, 1.5×35 mm (Shiseido Co., Ltd.)
solvent: SOLUTION A; 0.05% trifluoroacetic acid-containing water, SOLUTION B; 0.05% trifluoroacetic acid-containing acetonitrile
gradient cycle: 0.00 min (SOLUTION A/SOLUTION B=90/10), 2.00 min (SOLUTION A/SOLUTION B=5/95), 2.75 min (SOLUTION A/SOLUTION B=5/95), 2.76 min (SOLUTION A/SOLUTION B=90/10), 3.60 min (SOLUTION A/SOLUTION B=90/10)
injection volume: 2 μL, flow rate: 0.5 mL/min, detection method: UV220 nm
MS conditions
ionization method: electrospray method Purification by preparative HPLC in Example 21 was carried out under the following conditions.
apparatus: Gilson Inc., Preparative HPLC System
column: Waters SunFire Column C18S-5 μm, 30×50 mm
solvent: SOLUTION A; distilled water, SOLUTION B; acetonitrile
gradient cycle: 0.00 min (SOLUTION A/SOLUTION B=60/40), 1.00 min (SOLUTION A/SOLUTION B=60/40), 5.70 min (SOLUTION A/SOLUTION B=0/100), 8.00 min (SOLUTION A/SOLUTION B=0/100), 8.20 min (SOLUTION A/SOLUTION B=60/40), 8.50 min (SOLUTION A/SOLUTION B=60/40)
flow rate: 70 mL/min, detection method: UV 220 nm

Example 1

8-(furan-3-yl)-2,3,4,5-tetrahydrothieno[2,3-f][1,4]oxazepine 1 hydrochloride

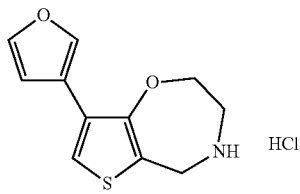 [SMILES: c1cc(-c2csc3c2OCCNC3)co1 ; Cl]

(step 1) 3-(2-amino-2-oxoethoxy)-4-bromothiophene-2-carboxylic acid

A solution of methyl 4-bromo-3-hydroxythiophene-2-carboxylate (53.0 g), potassium carbonate (46.2 g), 2-bromoacetamide (37.0 g) and DMF (500 ml) was stirred at 60° C. for 2 hr, and the solvent was evaporated under reduced pressure. Water (300 ml) was added to the residue, and the solid was collected by filtration. To the obtained solid were added potassium carbonate (61.6 g), water (20 ml) and MeOH (500 ml), and the mixture was stirred at 85° C. for 1 hr. After cooling to room temperature, the solid were collected by filtration. The obtained solid was dissolved in water (300 mL), and the mixture was adjusted with 6 N hydrochloric acid to pH 3. The obtained solid was collected by filtration, and washed with water to give the title compound (50.5 g, 80.8%) as a solid.

$^1$H-NMR (DMSO-$d_6$): δ4.90 (2H, s), 7.82 (1H, brs), 7.92 (1H, s), 8.00 (1H, brs), 13.46 (1H, brs).

(step 2) 8-bromothieno[2,3-f][1,4]oxazepine-3,5-(2H,4H)-dione

To a solution of 3-(2-amino-2-oxoethoxy)-4-bromothiophene-2-carboxylic acid (50.5 g), 1-hydroxybenzotriazole 1 hydrate (24.4 g) and DMF (500 mL) was added 1-ethyl-3-(3-dimethylaminopropyl)carbodiimide hydrochloride (34.5 g), and the mixture was stirred at room temperature for 4 hr. To the reaction mixture was added 1-ethyl-3-(3-dimethylaminopropyl)carbodiimide hydrochloride (34.5 g), and the mixture was stirred at room temperature for 12 hr. To the reaction mixture was added 1-ethyl-3-(3-dimethylaminopropyl)carbodiimide hydrochloride (34.5 g), and the mixture was stirred at room temperature for 7 hr. The solvent was evaporated under reduced pressure, and water (500 mL) was added to the residue to give the title compound (38.8 g, 82.2%) as a solid.

$^1$H-NMR (DMSO-$d_6$): δ4.96 (2H, s), 8.18 (1H, s), 11.60 (1H, s).

(step 3) tert-butyl 8-bromo-2,3-dihydrothieno[2,3-f][1,4]oxazepine-4(5H)-carboxylate To a solution of 8-bromothieno[2,3-f][1,4]oxazepine-3,5-(2H,4H)-dione (21.3 g) and THF (200 mL) was added 1N THF-borane complex-THF solution (500 ml), and the mixture was stirred at 65° C. for 3.5 hr. Under ice-cooling, to the reaction mixture was added 6N hydrochloric acid (236 ml,), and the mixture was stirred at 85° C. for 1 hr. The solvent was evaporated under reduced pressure. 8N Aqueous sodium hydroxide solution (250 mL) and water (100 ml) were added to the residue, and the mixture was extracted with ethyl acetate. The extract was washed with water, and dried over anhydrous magnesium sulfate, and the solvent was evaporated under reduced pressure. THF (300 ml), triethylamine (340 ml) and (Boc)$_2$O (35.4 g) were added to the residue, and the mixture was stirred at room temperature for 3 hr. To the reaction mixture were added water (20 mL) and 8 N aqueous sodium hydroxide solution (20 ml), and the mixture was stirred at room temperature for 12 hr. The solvent was evaporated under reduced pressure, the residue was poured into water, and the mixture was extracted with ethyl acetate. The extract was washed with water, and dried over anhydrous magnesium sulfate, and the solvent was evaporated under reduced pressure. The residue was purified by silica gel column chromatography (solvent gradient; 0→10% ethyl acetate/hexane) to give the title compound (19.3 g, 71.2%) as a solid.

$^1$H-NMR (CDCl$_3$): δ1.43 (9H, s), 3.82-3.85 (2H, m), 4.13 (2H, s), 4.47-4.55 (2H, m), 6.96 (1H, s).

(step 4) tert-butyl 8-(furan-3-yl)-2,3-dihydrothieno[2,3-f][1,4]oxazepine-4(5H)-carboxylate A mixture of tert-butyl 8-bromo-2,3-dihydrothieno[2,3-f][1,4]oxazepine-4(5H)-carboxylate (60.0 mg), 3-furanboronic acid (26.1 mg), EtOH (0.1 ml), 2N aqueous sodium carbonate solution (1 mL), tetrakis(triphenylphosphine)palladium (25 mg) and toluene (2 mL) was stirred at 95° C. for 12 hr under a nitrogen atmosphere, and the reaction mixture was poured into water. The mixture was extracted with ethyl acetate and the extract was washed with water, and dried over anhydrous magnesium sulfate. The solvent was evaporated under reduced pressure, and the residue was purified by silica gel column chromatography (solvent gradient; 0→33% ethyl acetate/hexane) to give the title compound (51.0 mg, 88.1%) as an oil.

$^1$H-NMR (CDCl$_3$): δ1.44 (9H, s), 3.85-3.88 (2H, m), 4.13-4.14 (2H, m), 4.48-4.56 (2H, m), 6.61-6.63 (1H, m), 6.94 (1H, s), 7.41-7.42 (1H, m), 7.86 (1H, s).

(step 5) 8-(furan-3-yl)-2,3,4,5-tetrahydrothieno[2,3-f][1,4]oxazepine 1 hydrochloride tert-Butyl 8-(furan-3-yl)-2,3-dihydrothieno[2,3-f][1,4]oxazepine-4(5H)-carboxylate (51.0 mg) was dissolved in ethyl acetate (2 ml,), and 4N hydrogen chloride-ethyl acetate solution (2 mL) was added. The mixture was stirred at room temperature for 1 hr, and the solvent was evaporated under reduced pressure. The residue was recrystallized from a mixed solvent of MeOH and Et$_2$O to give 8-(furan-3-yl)-2,3,4,5-tetrahydrothieno[2,3-f][1,4]oxazepine 1 hydrochloride (30.6 mg, 74.8%) as a solid.

$^1$H-NMR (CD$_3$OD): δ3.71-3.74 (2H, m), 4.37-4.39 (2H, m), 4.47 (2H, s), 4.88 (2H, brs), 6.76-6.77 (1H, m), 7.39 (1H, s), 7.50-7.51 (1H, m), 7.94-7.95 (1H, m).

ESI-MS (free base): m/z 222(M+H)$^+$.

Example 2

8-(3-fluorophenyl)-2,3,4,5-tetrahydrothieno[2,3-f][1,4]oxazepine 1 hydrochloride

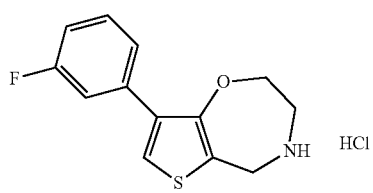 [SMILES: Fc1cccc(-c2csc3c2OCCNC3)c1 ; Cl]

(step 1) tert-butyl 8-(3-fluorophenyl)-2,3-dihydrothieno[2,3-f][1,4]oxazepine-4(5H)-carboxylate A mixture of tert-butyl 8-bromo-2,3-dihydrothieno[2,3-f][1,4]oxazepine-4(5H)-carboxylate (200 mg) obtained in Example 1, steps 1-3,3-fluorophenylboronic acid (126 mg), EtOH (0.4 mL), 2N aqueous sodium carbonate solution (4 mL), tetrakis(triphenylphosphine)palladium (83.1 mg) and toluene (8 ml) was stirred at 100° C. for 12 hr under a nitrogen atmosphere. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (solvent gradient; 0→10% ethyl acetate/hexane) to give the title compound (209 mg, 100%) as an oil.
$^1$H-NMR (CDCl$_3$): δ1.45 (9H, s), 3.85-3.88 (2H, m), 4.12 (2H, s), 4.51-4.59 (2H, m), 6.94-7.05 (2H, m), 7.24-7.33 (3H, m).

(step 2) 8-(3-fluorophenyl)-2,3,4,5-tetrahydrothieno[2,3-f][1,4]oxazepine 1 hydrochloride tert-Butyl 8-(3-fluorophenyl)-2,3-dihydrothieno[2,3-f][1,4]oxazepine-4(5H)-carboxylate (209 mg) was dissolved in ethyl acetate (2 ml), and 4 N hydrogen chloride-ethyl acetate solution (2 ml) was added. The mixture was stirred at room temperature for 1 hr, and the solvent was evaporated under reduced pressure. The residue was recrystallized from a mixed solvent of MeOH and Et$_2$O to give 8-(3-fluorophenyl)-2,3,4,5-tetrahydrothieno[2,3-f][1,4]oxazepine 1 hydrochloride (142 mg, 83.0%) as a solid.
$^1$H-NMR (DMSO-d$_6$): δ3.60 (2H, brs), 4.32 (2H, brs), 4.45 (2H, s), 7.14-7.18 (1H, m), 7.40-7.45 (3H, m), 7.74 (1H, s), 9.52 (2H, brs).
ESI-MS (free base): m/z 250(M+H)$^+$.
Elemental Analysis
Calculated (C$_{13}$H$_{12}$FNOS.HCl): C, 54.64; H, 4.59; N, 4.90. Found: C, 54.41; H, 4.60; N, 4.70.

Example 3

8-cyclopropyl-2,3,4,5-tetrahydrothieno[2,3-f][1,4]oxazepine 1 hydrochloride

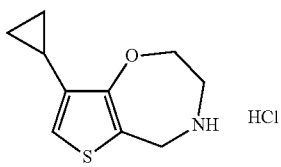 [SMILES: c1sc2c(c1C1CC1)OCCNC2 ; Cl]

(step 1) tert-butyl 8-cyclopropyl-2,3-dihydrothieno[2,3-f][1,4]oxazepine-4(5H)-carboxylate A mixture of tert-butyl 8-bromo-2,3-dihydrothieno[2,3-f][1,4]oxazepine-4(5H)-carboxylate (16.0 g) obtained in Example 1, steps 1-3, cyclopropylboronic acid (8.23 g), potassium tert-butoxide (12.5 g), tricyclohexylphosphine (1.88 g), palladium acetate (754 mg) and toluene (400 mL) was stirred at 100° C. for 8 hr, the reaction mixture was poured into water, the mixture was extracted with ethyl acetate. The extract was dried over anhydrous magnesium sulfate, and the solvent was evaporated under reduced pressure. The residue was purified by silica gel column chromatography (solvent gradient; 0→10% ethyl acetate/hexane) to give the title compound (10.6 g, 75.1%) as an oil.
$^1$H-NMR (CDCl$_3$): δ0.59-0.69 (2H, m), 0.77-0.86 (2H, m), 1.44 (9H, s), 1.75-1.84 (1H, m), 3.78-3.83 (2H, m), 4.09 (2H, brs), 4.44-4.52 (2H, m), 6.37 (1H, s).

(step 2) 8-cyclopropyl-2,3,4,5-tetrahydrothieno[2,3-f][1,4]oxazepine 1 hydrochloride tert-Butyl 8-cyclopropyl-2,3-dihydrothieno[2,3-f][1,4]oxazepine-4(5H)-carboxylate (10.6 g) was dissolved in ethyl acetate (100 ml), and 4N hydrogen chloride-ethyl acetate solution (100 mL) was added. The mixture was stirred at room temperature for 1 hr, and the precipitated solid was collected by filtration. This was recrystallized from a mixed solvent of MeOH and Et$_2$O to give 8-cyclopropyl-2,3,4,5-tetrahydrothieno[2,3-f][1,4]oxazepine 1 hydrochloride (4.30 g, 51.3%) as a solid.
$^1$H-NMR (DMSO-d$_6$): δ0.59-0.62 (2H, m), 0.80-0.86 (2H, m), 1.71-1.80 (1H, m), 3.51-3.53 (2H, m), 4.23-4.26 (2H, m), 4.32 (2H, s), 6.86 (1H, s), 9.20 (2H, brs).
ESI-MS (free base): m/z 196 (M+H)$^+$.
Elemental Analysis
Calculated (C$_{10}$H$_{15}$NOS.HCl): C, 51.38; H, 6.90; N, 5.99. Found: C, 51.38; H, 6.90; N, 5.93.

Example 4

8-(1-methylethyl)-2,3,4,5-tetrahydrothieno[2,3-f][1,4]oxazepine 1 hydrochloride

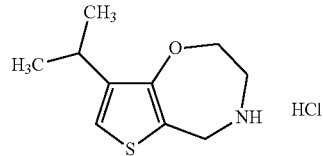

(step 1) tert-butyl 8-(1-methylethenyl)-2,3-dihydrothieno[2,3-f][1,4]oxazepine-4(5H)-carboxylate A mixture of tert-butyl 8-bromo-2,3-dihydrothieno[2,3-f][1,4]oxazepine-4(5H)-carboxylate (334 mg) obtained in Example 1, steps 1-3, isopropenylboronic acid pinacol ester (168 mg), saturated aqueous sodium carbonate solution (6 ml), tetrakis(triphenylphosphine)palladium (32.5 mg) and DME (9 ml) was stirred at 85° C. for 12 hr under a nitrogen atmosphere, and poured into water, and the mixture was extracted with ethyl acetate. The extract was dried over anhydrous magnesium sulfate, and the solvent was evaporated under reduced pressure. The residue was purified by silica gel column chromatography (solvent gradient; 0→30% ethyl acetate/hexane) to give the title compound (270 mg, 91.5%) as an oil.
$^1$H-NMR (CDCl$_3$): δ1.44 (9H, s), 2.07 (3H, s), 3.83-3.85 (2H, m), 4.08 (2H, brs), 4.45-4.53 (2H, m), 5.06 (1H, s), 5.58 (1H, s), 6.84 (1H, s).

(step 2) tert-butyl 8-(1-methylethyl)-2,3-dihydrothieno[2,3-f][1,4]oxazepine-4(5H)-carboxylate A mixture of tert-butyl 8-(1-methylethenyl)-2,3-dihydrothieno[2,3-f][1,4]oxazepine-4(5H)-carboxylate (270 mg), 10% palladium on carbon (50 mg) and EtOH (5 mL) was stirred for 12 hr under a hydrogen atmosphere. The insoluble material was filtered off, and the filtrate was concentrated to give the title compound (270 mg, 99.6%) as an oil.

$^1$H-NMR (CDCl$_3$): δ1.18 (6H, d, J=6.6 Hz), 1.43 (9H, s), 2.83-2.92 (1H, m), 3.81-3.83 (2H, m), 4.03-4.06 (2H, m), 4.44-4.52 (2H, m), 6.58 (1H, s).

(step 3) 8-(1-methylethyl)-2,3,4,5-tetrahydrothieno[2,3-f][1,4]oxazepine 1 hydrochloride tert-Butyl 8-(1-methylethyl)-2,3-dihydrothieno[2,3-f][1,4]oxazepine-4(5H)-carboxylate (270 mg) was dissolved in ethyl acetate (2 mL), 4N hydrogen chloride-ethyl acetate solution (6 mL) was added, and the mixture was stirred at room temperature for 1 hr. The solvent was evaporated under reduced pressure, and the residue was recrystallized from a mixed solvent of MeOH and Et$_2$O to give 8-(1-methylethyl)-2,3,4,5-tetrahydrothieno[2,3-f][1,4]oxazepine 1 hydrochloride (192 mg, 89.7%) as a solid.

$^1$H-NMR (DMSO-d$_6$): δ1.15 (6H, d, J=6.9 Hz), 2.78-2.87 (1H, m), 3.52-3.54 (2H, m), 4.22-4.25 (2H, m), 4.34 (2H, s), 7.04 (1H, s), 9.52 (2H, brs).

ESI-MS (free base): m/z 198 (M+H)$^+$.

Elemental Analysis

Calculated (C$_{10}$H$_{13}$NOS.HCl): C, 51.83; H, 6.09; N, 6.04. Found: C, 51.60; H, 6.00; N, 6.04.

Example 5

8-cyclobutyl-2,3,4,5-tetrahydrothieno[2,3-f][1,4]oxazepine 1 hydrochloride

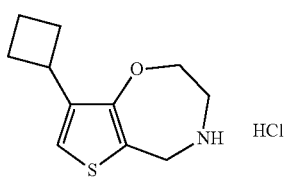 [SMILES: c1sc2c(c1C1CCC1)OCCNC2 ; Cl]

(step 1) 1-(2,3,4,5-tetrahydrothieno[2,3-f][1,4]oxazepin-8-yl)cyclobutanol

To a solution of tert-butyl 8-bromo-2,3-dihydrothieno[2,3-f][1,4]oxazepine-4(5H)-carboxylate (334 mg) obtained in Example 1, steps 1-3, and Et$_2$O (10 mL) was added dropwise 1.6 N hexane solution of n-butyllithium (72.4 ml) at −78° C., and the mixture was stirred at −78° C. for 15 min. Cyclobutanone (0.0747 ml) was added, and the mixture was stirred at −78° C. for 1 hr. To the reaction mixture was added water (10 mL), and the organic layer was separated and dried over anhydrous magnesium sulfate. The solvent was evaporated under reduced pressure, and the residue was purified by silica gel column chromatography (solvent gradient; 0→50% ethyl acetate/hexane) to give the title compound (190 mg, 58.5%) as an oil.

$^1$H-NMR (CDCl$_3$): δ1.44 (9H, s), 1.86-2.14 (2H, m), 2.26-2.45 (4H, m), 3.18 (1H, s), 3.82-3.85 (2H, m), 4.10-4.12 (2H, m), 4.46-4.53 (2H, m), 6.84 (1H, s).

(step 2) 8-cyclobutyl-2,3,4,5-tetrahydrothieno[2,3-f][1,4]oxazepine 1 hydrochloride To 1-(2,3,4,5-tetrahydrothieno[2,3-f][1,4]oxazepin-8-yl)cyclobutanol (1.00 g) were added triethylsilane (4.90 ml) and trifluoroacetic acid (4.73 ml) in this order under ice-cooling, and the mixture was stirred at 70° C. for 1 hr. The solvent was evaporated under reduced pressure, ice water (10 ml) and 8N aqueous sodium hydroxide solution (10 mL) were added to the residue, and the mixture was extracted with ethyl acetate. The extract was dried over anhydrous magnesium sulfate, the solvent was evaporated under reduced pressure, and the residue was purified by silica gel column chromatography (solvent gradient; 0→50% ethyl acetate/hexane) to give 8-cyclobutyl-2,3,4,5-tetrahydrothieno[2,3-f][1,4]oxazepine as an oil. Ethyl acetate (5 mL) and 4N hydrogen chloride-ethyl acetate solution (5 mL) were added thereto, and the solvent was evaporated under reduced pressure. The residue was recrystallized from a mixed solvent of MeOH and Et$_2$O to give 8-cyclobutyl-2,3,4,5-tetrahydrothieno[2,3-f][1,4]oxazepine 1 hydrochloride (360 mg, 47.7%) as a solid.

$^1$H-NMR (DMSO-d$_6$): δ1.82-2.25 (6H, m), 3.26-3.40 (1H, m), 3.50-3.52 (2H, m), 4.18-4.21 (2H, m), 4.33 (2H, s), 7.12 (1H, s), 9.21 (2H, brs).

ESI-MS (free base): m/z 210(M+H)$^+$.

Elemental Analysis

Calculated (C$_{11}$H$_{15}$NOS.HCl): C, 53.76; H, 6.56; N, 5.70. Found: C, 53.70; H, 6.65; N, 5.57.

Example 6

8-(3-methoxyphenyl)-2-methyl-2,3,4,5-tetrahydrothieno[2,3-f][1,4]oxazepine 1 hydrochloride

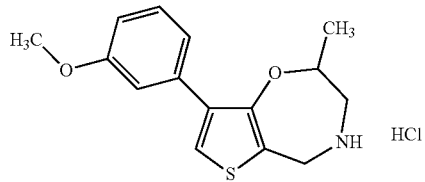 [SMILES: COc1cccc(-c2csc3c2OC(C)CNC3)c1 ; Cl]

(step 1) methyl 4-bromo-3-(2-tert-butoxy-1-methyl-2-oxoethoxy)thiophene-2-carboxylate A solution of methyl 4-bromo-3-hydroxythiophene-2-carboxylate (1.42 g), tert-butyl 2-bromopropanoate (1.2 mL), potassium carbonate (2.45 g) and DMF (30 mL) was stirred at 50° C. for 2 hr. The reaction mixture was cooled to room temperature, and poured into water, and the mixture was extracted with ethyl acetate. The extract was washed with water and saturated brine, and dried over magnesium sulfate, and the solvent was evaporated under reduced pressure. The residue was recrystallized from a mixed solvent of ethyl acetate and hexane to give the title compound (2.16 g, 99%) as colorless crystals.

$^1$H-NMR (CDCl$_3$): δ1.43 (9H, s), 1.58 (3H, d, J=6.8 Hz), 3.85 (3H, s), 5.16 (1H, q, J=6.8 Hz), 7.38 (1H, s).

(step 2) 2-{[4-bromo-2-(methoxycarbonyl)thiophen-3-yl]oxy}propanoic acid

A solution of methyl 4-bromo-3-(2-tert-butoxy-1-methyl-2-oxoethoxy)thiophene-2-carboxylate (890 mg) and trifluoroacetic acid (5 ml) was stirred at room temperature for 20 min. The reaction mixture was concentrated under reduced pressure, and the obtained residue was diluted with ethyl acetate, washed with water and saturated brine, and dried over magnesium sulfate, and the solvent was evaporated under reduced pressure. The residue was recrystallized from a mixed solvent of Et$_2$O and hexane to give the title compound (715 mg, 95%) as colorless crystals.

$^1$H-NMR (CDCl$_3$): δ1.69 (3H, d, J=7.1 Hz), 3.92 (3H, s), 5.18 (1H, q, J=7.1 Hz), 7.48 (1H, s).

(step 3) methyl 3-(2-amino-1-methyl-2-oxoethoxy)-4-bromothiophene-2-carboxylate

A solution of 2-{[4-bromo-2-(methoxycarbonyl)thiophen-3-yl]oxy}propanoic acid (220 mg), 1H-benzotriazol-1-ol 1 ammonium salt (162 mg), 1-ethyl-3-(3-dimethylaminopropyl)carbodiimide hydrochloride (205 mg) and DMF (4 mL) was stirred at room temperature for 1.5 hr. Water was poured into the reaction mixture, and the mixture was extracted with ethyl acetate. The extract was washed with water and saturated brine, and dried over magnesium sulfate, and the solvent was evaporated under reduced pressure. The residue was recrystallized from a mixed solvent of Et$_2$O and hexane to give the title compound (195 mg, 89%) as colorless crystals.

$^1$H-NMR (CDCl$_3$): δ1.59 (3H, d, J=6.8 Hz), 3.87 (3H, s), 5.13 (1H, q, J=6.8 Hz), 5.65 (1H, brs), 7.44 (1H, s), 7.72 (1H, brs).

ESI-MS: m/z 309(M+H)$^+$.

(step 4) 3-(2-amino-1-methyl-2-oxoethoxy)-4-bromothiophene-2-carboxylic acid

To a mixture of methyl 3-(2-amino-1-methyl-2-oxoethoxy)-4-bromothiophene-2-carboxylate (634 mg), MeOH (20 mL) and water (0.074 ml) was added potassium carbonate (853 mg), and the mixture was stirred at 65° C. for 1.5 hr. The reaction mixture was concentrated under reduced pressure, the residue was acidified (pH 1) with 1N hydrochloric acid, and the mixture was extracted with ethyl acetate. The extract was washed with water and saturated brine, and dried over magnesium sulfate, and the solvent was evaporated under reduced pressure. The residue was recrystallized from a mixed solvent of Et$_2$O and hexane to give the title compound (444 mg, 73%) as colorless crystals.

$^1$H-NMR (CDCl$_2$): δ1.50 (3H, d, J=6.8 Hz), 5.17 (1H, q, J=6.8 Hz), 7.69-7.86 (2H, m), 7.93 (1H, s).

ESI-MS: m/z 295(M+H)$^+$.

(step 5) 8-bromo-2-methylthieno[2,3-f][1,4]oxazepine-3,5(2H,4H)-dione

A solution of 3-(2-amino-1-methyl-2-oxoethoxy)-4-bromothiophene-2-carboxylic acid (400 mg), 1-ethyl-3-(3-dimethylaminopropyl)carbodiimide hydrochloride (521 mg), 1-hydroxybenzotriazole 1 hydrate (417 mg) and DMF (4 mL) was stirred at room temperature for 1.5 hr. Water was poured into the reaction mixture, and the mixture was extracted with ethyl acetate. The extract was washed with saturated aqueous sodium hydrogen carbonate solution and saturated brine, and dried over magnesium sulfate, and the solvent was evaporated under reduced pressure. The residue was recrystallized from a mixed solvent of Et$_2$O and hexane to give the title compound (290 mg, 77%) as colorless crystals.

$^1$H-NMR (CDCl$_3$): δ1.72 (3H, d, J=6.8 Hz), 4.79 (1H, q, J=6.8 Hz), 7.59 (1H, s), 8.22 (brs, 1H).

(step 6) tert-butyl 8-bromo-2-methyl-2,3-dihydrothieno[2,3-f][1,4]oxazepine-4(5H)-carboxylate To a solution of 8-bromo-2-methylthieno[2,3-f][1,4]oxazepine-3,5(2H,4H)-dione (5.0 g) and THF (100 ml,) was added 1M THF-borane complex-THF solution (73 ml) at 0° C., and the mixture was stirred at 65° C. for 1 hr. The reaction solution was cooled to 0° C., and the mixture was adjusted to pH 2 with 6 N hydrochloric acid. The mixture was stirred at 65° C. for 1 hr, and at room temperature for 15 hr. The reaction solution was cooled to 0° C., basified with 8 N sodium hydroxide, and extracted with ethyl acetate. The extract was washed with water and saturated brine, and dried over magnesium sulfate, and the solvent was evaporated under reduced pressure. To a solution of the residue in THF (100 ml) were added (Boc)$_2$O (5.14 g) and 1 N aqueous sodium hydroxide solution (25 mL), and the mixture was stirred at room temperature for 1.5 hr. Water was poured into the reaction mixture, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 5→13% ethyl acetate/hexane) to give the title compound (3.56 g, 56%) as a colorless oil.

$^1$H-NMR (CDCl$_3$): δ1.32-1.40 (3H, m), 1.43 (9H, s), 3.22-3.54 (1H, m), 3.87-4.41 (3H, m), 4.58-4.75 (1H, m), 6.95 (1H, s).

ESI-MS: m/z 250(M-Boc+H)$^+$.

(step 7) tert-butyl 8-(3-methoxyphenyl)-2-methyl-2,3-dihydrothieno[2,3-f][1,4]oxazepine-4(5H)-carboxylate A mixed solution of tert-butyl 8-bromo-2-methyl-2,3-dihydrothieno[2,3-f][1,4]oxazepine-4(5H)-carboxylate (348 mg), (3-methoxyphenyl)boronic acid (198 mg), dichlorobis(triphenylphosphine)palladium (35 mg) and potassium carbonate (415 mg) in DME-water (1:1, 10 mL) was stirred at 85° C. for 1.5 hr under a nitrogen stream. The reaction solution was cooled to room temperature, water was added, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 0→10% ethyl acetate/hexane) to give the title compound (294 mg, 78%) as a colorless oil.

$^1$H-NMR (CDCl$_3$): δ1.33 (3H, d, J=6.1 Hz), 1.44 (9H, s), 3.19-3.47 (1H, m), 3.83 (3H, s), 3.94-4.37 (3H, m), 4.65-4.87 (1H, m), 6.82-6.88 (1H, m), 7.05 (1H, s), 7.14-7.20 (2H, m), 7.27-7.33 (1H, m).

ESI-MS: m/z 276 (M-Boc+H)$^+$.

(step 8) 8-(3-methoxyphenyl)-2-methyl-2,3,4,5-tetrahydrothieno[2,3-f][1,4]oxazepine 1 hydrochloride tert-Butyl 8-(3-methoxyphenyl)-2-methyl-2,3-dihydrothieno[2,3-f][1,4]oxazepine-4(5H)-carboxylate (287 mg) was stirred in 4 N hydrogen chloride-ethyl acetate solution (5 mL) for 30 min. The reaction solution was concentrated under reduced pressure, and the residue was recrystallized from ethyl acetate to give 8-(3-methoxyphenyl)-2-methyl-2,3,4,5-tetrahydrothieno[2,3-f][1,4]oxazepine 1 hydrochloride (220 mg, 92%) as colorless crystals.

$^1$H-NMR (DMSO-d$_6$): δ1.36 (3H, d, J=6.4 Hz), 3.34-3.40 (1H, m), 3.60 (1H, d, J=14.0 Hz), 3.79 (3H, s), 4.26-4.46 (2H, m), 4.53 (1H, d, J=15.5 Hz), 6.86-6.95 (1H, m), 7.14-7.23 (2H, m), 7.29-7.39 (1H, m), 7.65 (1H, s), 9.70 (2H, brs).

ESI-MS (free base): m/z 276(M+H)$^+$.

Example 7

8-(3-fluorophenyl)-2-methyl-2,3,4,5-tetrahydrothieno[2,3-f][1,4]oxazepine 1 hydrochloride

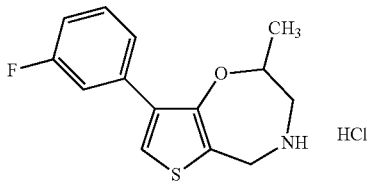 [SMILES: CC1CNCc2scc(-c3cccc(F)c3)c2O1 ; Cl]

(step 1) tert-butyl 8-(3-fluorophenyl)-2-methyl-2,3-dihydrothieno[2,3-f][1,4]oxazepine-4(5H)-carboxylate A mixed solution of tert-butyl 8-bromo-2-methyl-2,3-dihydrothieno[2,3-f][1,4]oxazepine-4(5H)-carboxylate (348 mg) obtained in Example 6, steps 1-6, (3-fluorophenyl)boronic acid (182 mg), dichlorobis(triphenylphosphine)palladium (35 mg) and potassium carbonate (415 mg) in DME-water (1:1, 10 ml) was stirred at 85° C. for 2 hr under a nitrogen stream. The reaction solution was cooled to room temperature, water was added, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 5-12% ethyl acetate/hexane) to give the title compound (281 mg, 77%) as a colorless oil.

$^1$H-NMR (CDCl$_3$): δ1.33 (3H, d, J=6.2 Hz), 1.44 (9H, s), 3.20-3.49 (1H, m), 3.94-4.37 (3H, m), 4.65-4.87 (1H, m), 6.94-7.03 (1H, m), 7.07 (1H, s), 7.28-7.40 (3H, m).

(step 2) 8-(3-fluorophenyl)-2-methyl-2,3,4,5-tetrahydrothieno[2,3-f][1,4]oxazepine 1 hydrochloride tert-Butyl 8-(3-fluorophenyl)-2-methyl-2,3-dihydrothieno[2,3-f][1,4]oxazepine-4(5H)-carboxylate (274 mg) was stirred in 4N hydrogen chloride-ethyl acetate solution (5 mL) for 30 min. The precipitated crystals were washed with ethyl acetate to give 8-(3-fluorophenyl)-2-methyl-2,3,4,5-tetrahydrothieno[2,3-f][1,4]oxazepine 1 hydrochloride (207 mg, 92%) as colorless crystals.

$^1$H-NMR (DMSO-d$_6$): δ1.37 (3H, d, J=6.4 Hz), 3.27-3.40 (1H, m), 3.56-3.66 (1H, m), 4.26-4.60 (3H, m), 7.12-7.23 (1H, m), 7.41-7.53 (3H, m), 7.75 (1H, s), 9.85 (2H, brs).

ESI-MS (free base): m/z 264 (M+H)$^+$.

Example 8

8-(2-fluorophenyl)-2-methyl-2,3,4,5-tetrahydrothieno[2,3-f][1,4]oxazepine 1 hydrochloride

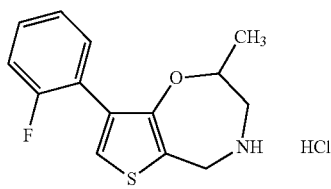 [SMILES: CC1CNCc2scc(-c3ccccc3F)c2O1 ; Cl]

(step 1) tert-butyl 8-(2-fluorophenyl)-2-methyl-2,3-dihydrothieno[2,3-f][1,4]oxazepine-4(5H)-carboxylate A mixed solution of tert-butyl 8-bromo-2-methyl-2,3-dihydrothieno[2,3-f][1,4]oxazepine-4(5H)-carboxylate (174 mg) obtained in Example 6, steps 1-6, (2-fluorophenyl)boronic acid (84 mg), dichlorobis(triphenylphosphine)palladium (18 mg) and potassium carbonate (207 mg) in DME-water (1:1, 5 ml,) was stirred at 85° C. for 2 hr under a nitrogen stream. The reaction solution was cooled to room temperature, water was added, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 0→10% ethyl acetate/hexane) to give the title compound (174 mg, 96%) as a colorless oil.

$^1$H-NMR (CDCl$_3$): δ1.24-1.30 (3H, m), 1.45 (9H, s), 3.12-3.43 (1H, m), 3.95-4.32 (3H, m), 4.67-4.93 (1H, m), 7.06-7.19 (3H, m). 7.24-7.33 (1H, m) 7.41-7.50 (1H, m).

(step 2) 8-(2-fluorophenyl)-2-methyl-2,3,4,5-tetrahydrothieno[2,3-f][1,4]oxazepine 1 hydrochloride tert-Butyl 8-(2-fluorophenyl)-2-methyl-2,3-dihydrothieno[2,3-f][1,4]oxazepine-4(5H)-carboxylate (168 mg) was stirred in 4 N hydrogen chloride-ethyl acetate solution (5 mL) for 30 min. The reaction solution was concentrated under reduced pressure, and the residue was recrystallized from ethyl acetate to give 8-(2-fluorophenyl)-2-methyl-2,3,4,5-tetrahydrothieno[2,3-f][1,4]oxazepine 1 hydrochloride (132 mg, 95%) as colorless crystals.

$^1$H-NMR (DMSO-d$_6$): δ1.27 (3H, d, J=6.4 Hz), 3.22-3.30 (1H, m), 3.60 (1H, d, J=14.0 Hz), 4.24-4.42 (2H, m), 4.54 (1H, d, J=15.2 Hz), 7.23-7.34 (2H, m), 7.37-7.48 (2H, m), 7.54 (1H, s), 9.77 (2H, brs).

ESI-MS (free base): m/z 264(M+H)$^+$.

Example 9

8-cyclopropyl-2-methyl-2,3,4,5-tetrahydrothieno[2,3-f][1,4]oxazepine 1 hydrochloride

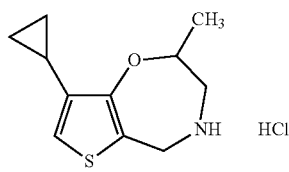

(step 1) tert-butyl 8-cyclopropyl-2-methyl-2,3-dihydrothieno[2,3-f][1,4]oxazepine-4(5H)-carboxylate A suspension of tert-butyl 8-bromo-2-methyl-2,3-dihydrothieno[2,3-f][1,4]oxazepine-4(5H)-carboxylate (348 mg) obtained in Example 6, steps 1-6, cyclopropylboronic acid (129 mg), palladium acetate (11.2 mg), tricyclohexylphosphine (28 mg), potassium tert-butoxide (337 mg) and toluene (5 mL) was stirred at 80° C. for 16 hr under an argon atmosphere. The reaction solution was cooled to room temperature, and filtered through celite. Water was added, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 0→10% ethyl acetate/hexane) to give the title compound (266 mg, 86%) as a pale-yellow oil.

$^1$H-NMR (CDCl$_3$): δ0.53-0.72 (2H, m), 0.77-0.89 (2H, m), 1.34 (3H, d, J=6.4 Hz), 1.42 (9H, s), 1.73-1.86 (1H, m), 3.16-3.51 (1H, m), 3.86-4.35 (3H, m), 4.54-4.77 (1H, m), 6.36 (1H, s).

(step 2) 8-cyclopropyl-2-methyl-2,3,4,5-tetrahydrothieno[2,3-f][1,4]oxazepine 1 hydrochloride tert-Butyl 8-cyclopropyl-2-methyl-2,3-dihydrothieno[2,3-f][1,4]oxazepine-4(5H)-carboxylate (254 mg) was stirred in 4N hydrogen chloride-ethyl acetate solution (5 ml,) for 20 min.

The reaction solution was concentrated under reduced pressure, and the residue was recrystallized from ethyl acetate to give 8-cyclopropyl-2-methyl-2,3,4,5-tetrahydrothieno[2,3-f][1,4]oxazepine 1 hydrochloride (184 mg, 91%) as colorless crystals.

$^1$H-NMR (DMSO-d$_6$): δ0.49-0.75 (2H, m), 0.76-0.90 (2H, m), 1.37 (3H, d, J=6.4 Hz), 1.70-1.84 (1H, m), 3.20-3.33 (1H, m), 3.56 (1H, d, J=14.0 Hz), 4.15-4.47 (3H, m), 6.86 (1H, s), 9.73 (2H, brs).

ESI-MS (free base): m/z 210(M+H)$^+$.

Example 10

2-methyl-8-(1-methylethyl)-2,3,4,5-tetrahydrothieno[2,3-f][1,4]oxazepine 1 hydrochloride

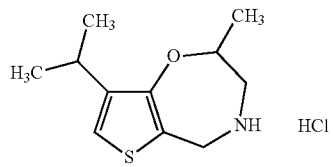

(step 1) tert-butyl 2-methyl-8-(1-methylethenyl)-2,3-dihydrothieno[2,3-f][1,4]oxazepine-4(5H)-carboxylate A mixed solution of tert-butyl 8-bromo-2-methyl-2,3-dihydrothieno[2,3-f][1,4]oxazepine-4(5H)-carboxylate (418 mg) obtained in Example 6, steps 1-6, isopropenylboronic acid pinacol ester (0.293 ml), dichlorobis(triphenylphosphine)palladium (42 mg) and potassium carbonate (498 mg) in DME-water (1:1, 10 mL) was stirred at 85° C. for 1 hr under a nitrogen stream. The reaction solution was cooled to room temperature, water was added, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 5→12% ethyl acetate/hexane) to give the title compound (274 mg, 74%) as a colorless oil.

$^1$H-NMR (CDCl$_3$): δ1.35 (3H, d, J=6.4 Hz), 1.43 (9H, s), 2.07 (3H, s), 3.16-3.48 (1H, m), 3.89-4.33 (3H, m), 4.57-4.80 (1H, m), 5.07 (1H, s), 5.66 (1H, s), 6.84 (1H, s).

(step 2) tert-butyl 2-methyl-8-(1-methylethyl)-2,3-dihydrothieno[2,3-f][1,4]oxazepine-4(5H)-carboxylate To a solution of tert-butyl 2-methyl-8-(1-methylethenyl)-2,3-dihydrothieno[2,3-f][1,4]oxazepine-4(5H)-carboxylate (269 mg) in THF-MeOH (2:1, 15 ml) was added 10% palladium on carbon (30 mg), and the mixture was stirred for 2 hr under a hydrogen atmosphere. The reaction solution was filtered and concentrated under reduced pressure. The residue was purified by silica gel column chromatography (solvent gradient; 0→10% ethyl acetate/hexane) to give the title compound (243 mg, 90%) as a colorless oil.

$^1$H-NMR (CDCl$_3$): δ1.16-1.22 (6H, m), 1.34 (3H, d, J=6.4 Hz), 1.43 (9H, s), 2.79-2.95 (1H, m), 3.12-3.43 (1H, m), 3.88-4.30 (3H, m), 4.60-4.82 (1H, m), 6.58 (1H, s).

(step 3) 2-methyl-8-(1-methylethyl)-2,3,4,5-tetrahydrothieno[2,3-f][1,4]oxazepine 1 hydrochloride tert-Butyl 2-methyl-8-(1-methylethyl)-2,3-dihydrothieno[2,3-f][1,4]oxazepine-4(5H)-carboxylate (235 mg) was stirred in 4N hydrogen chloride-ethyl acetate solution (5 mL) for 20 min. The reaction solution was concentrated under reduced pressure, and the residue was recrystallized from ethyl acetate to give 2-methyl-8-(1-methylethyl)-2,3,4,5-tetrahydrothieno[2,3-f][1,4]oxazepine 1 hydrochloride (146 mg, 78%) as colorless crystals.

$^1$H-NMR (DMSO-d$_6$): δ1.15 (6H, d, J=6.8 Hz), 1.37 (3H, d, J=6.6 Hz), 2.77-2.89 (1H, m), 3.22-3.29 (1H, m), 3.57 (1H, d, J=13.9 Hz), 4.15-4.30 (2H, m), 4.36-4.47 (1H, m), 7.04 (1H, s), 9.66 (2H, brs).

ESI-MS (free base): m/z 212 (M+H)$^+$.

Example 11

8-ethyl-2-methyl-2,3,4,5-tetrahydrothieno[2,3-f][1,4]oxazepine 1 hydrochloride

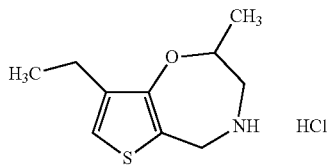

(step 1) tert-butyl 8-ethenyl-2-methyl-2,3-dihydrothieno[2,3-f][1,4]oxazepine-4(5H)-carboxylate A mixed solution of tert-butyl 8-bromo-2-methyl-2,3-dihydrothieno[2,3-f][1,4]oxazepine-4(5H)-carboxylate (418 mg) obtained in Example 6, steps 1-6, vinylboronic acid pinacol ester (0.221 mL), dichlorobis(triphenylphosphine)palladium (42 mg) and potassium carbonate (498 mg) in DME-water (1:1, 10 ml,) was stirred at 85° C. for 1.5 hr under a nitrogen stream. The reaction solution was cooled to room temperature, water was added, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 0→10% ethyl acetate/hexane) to give the title compound (239 mg, 68%) as a colorless oil.

¹H-NMR (CDCl₃): δ1.35 (3H, d, J=6.4 Hz), 1.43 (9H, s), 3.17-3.49 (1H, m), 3.88-4.35 (3H, m), 4.57-4.81 (1H, m), 5.17 (1H, d, J=11.4 Hz), 5.77 (1H, d, J=17.8 Hz), 6.57 (1H, dd, J=17.8, 11.4 Hz), 6.92 (1H, s).

(step 2) tert-butyl 8-ethyl-2-methyl-2,3-dihydrothieno[2,3-f][1,4]oxazepine-4(5H)-carboxylate To a solution of tert-butyl 8-ethenyl-2-methyl-2,3-dihydrothieno[2,3-f][1,4]oxazepine-4(5H)-carboxylate (231 mg) in THF-MeOH (2:1, 15 mL) was added 10% palladium on carbon (50 mg), and the mixture was stirred for 1 hr under a hydrogen atmosphere. The reaction solution was filtered and concentrated under reduced pressure. The residue was purified by silica gel column chromatography (solvent gradient; 0→15% ethyl acetate/hexane) to give the title compound (195 mg, 84%) as a colorless oil.

¹H-NMR (CDCl₃): δ1.17 (3H, t, J=7.5 Hz), 1.33 (3H, d, J=6.4 Hz), 1.43 (9H, s), 2.46 (2H, q, J=7.5 Hz), 3.14-3.48 (1H, m), 3.86-4.35 (3H, m), 4.57-4.80 (1H, m), 6.59 (1H, s).

(step 3) 8-ethyl-2-methyl-2,3,4,5-tetrahydrothieno[2,3-f][1,4]oxazepine 1 hydrochloride tert-Butyl 8-ethyl-2-methyl-2,3-dihydrothieno[2,3-f][1,4]oxazepine-4(5H)-carboxylate (190 mg) was stirred in 4N hydrogen chloride-ethyl acetate solution (5 mL) for 20 min. The reaction solution was concentrated under reduced pressure, and the residue was recrystallized from ethyl acetate to give 8-ethyl-2-methyl-2,3,4,5-tetrahydrothieno[2,3-f][1,4]oxazepine 1 hydrochloride (131 mg, 88%) as colorless crystals.

¹H-NMR (DMSO-d₆): δ1.12 (3H, t, J=7.4 Hz), 1.36 (3H, d, J=6.4 Hz), 2.36-2.47 (2H, m), 3.21-3.29 (1H, m), 3.56 (1H, d, J=14.0 Hz), 4.16-4.32 (2H, m), 4.37-4.48 (1H, m), 7.05 (1H, s), 9.72 (2H, brs).
ESI-MS (free base): m/z 198 (M+H)⁺.

Example 12

(2S)-8-(3-fluorophenyl)-2-methyl-2,3,4,5-tetrahydrothieno[2,3-f][1,4]oxazepine 1 hydrochloride

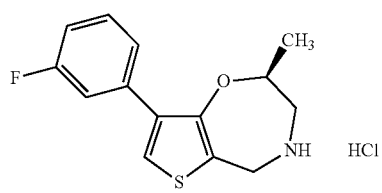 [SMILES: C[C@H]1CNCc2scc(-c3cccc(F)c3)c2O1 ; Cl]

(step 1) tert-butyl [(2R)-2-hydroxypropyl]carbamate

To a solution of (2R)-1-aminopropan-2-ol (1.85 g) and THF (100 mL) was added (Boc)₂O (5.91 g), and the mixture was stirred at room temperature for 2 hr. Water was added to the reaction solution, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 10-450% ethyl acetate/hexane) to give the title compound (3.76 g, 87%) as a colorless oil.

¹H-NMR (CDCl₃): δ1.18 (3H, d, J=6.4 Hz), 1.45 (9H, s), 2.28 (1H, brs), 2.93-3.07 (1H, m), 3.20-3.33 (1H, m), 3.83-3.97 (1H, m), 4.90 (1H, brs).

(step 2) methyl 4-bromo-3-{(1S)-2-[(tert-butoxycarbonyl)amino]-1-methylethoxy}thiophene-2-carboxylate To a solution of methyl 4-bromo-3-hydroxythiophene-2-carboxylate (237 mg), tert-butyl [(2R)-2-hydroxypropyl]carbamate (175 mg), tri-n-butylphosphine (0.75 mL) and THF (10 mL) was added dropwise diethyl azodicarboxylate (40% toluene solution, 1.4 mL) at room temperature, and the mixture was stirred for 2 hr. The reaction solution was concentrated under reduced pressure, and the residue was purified by silica gel column chromatography (solvent gradient; 0→15% ethyl acetate/hexane) to give the title compound (239 mg, 65%) as a colorless oil.

¹H-NMR (CDCl₃): δ1.33 (3H, d, J=6.4 Hz), 1.45 (9H, s), 3.35-3.42 (2H, m), 3.88 (3H, s), 4.67-4.79 (1H, m), 5.51-5.62 (1H, m), 7.41 (1H, s).
ESI-MS: m/z 296(M-Boc+H)⁺.

(step 3) tert-butyl [(2S)-2-{[4-bromo-2-(hydroxymethyl)thiophen-3-yl]oxy}propyl]carbamate To a solution of methyl 4-bromo-3-{(1S)-2-[(tert-butoxycarbonyl)amino]-1-methylethoxy}thiophene-2-carboxylate (15.36 g) in THF-MeOH (5:1, 180 mL) was added 8 N aqueous sodium hydroxide solution (7.5 mL) at room temperature, and the mixture was stirred at 50° C. for 1 hr. The reaction solution was cooled to room temperature, neutralized with 6 N hydrochloric acid (10 mL), and extracted with ethyl acetate. The extract was washed with water and saturated brine, and dried over magnesium sulfate, and the solvent was evaporated under reduced pressure. To a solution (250 ml) of the residue in THF were added isobutyl chloroformate (5.6 mL) and triethylamine (6.5 ml), and the mixture was stirred at room temperature for 30 min. The reaction solution was filtered, a solution (10 ml) of sodium borohydride (4.42 g) in water was added to the filtrate, and the mixture was stirred at room temperature for 30 min. Saturated aqueous ammonium solution was added to the reaction solution, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 10→25% ethyl acetate/hexane) to give the title compound (12.82 g, 90%) as a colorless oil.

¹H-NMR (CDCl₃): δ1.27 (3H, d, J=6.4 Hz), 1.44 (9H, s), 3.21-3.33 (1H, m), 3.39-3.50 (1H, m), 4.39-4.53 (1H, m), 4.61-4.84 (2H, m), 5.16 (1H, brs), 7.16 (1H, s).

(step 4) tert-butyl (2S)-8-bromo-2-methyl-2,3-dihydrothieno[2,3-f][1,4]oxazepine-4(5H)-carboxylate To a solution of tert-butyl [(2S)-2-{[4-bromo-2-(hydroxymethyl)thiophen-3-yl]oxy}propyl]carbamate (1.83 g), methanesulfonyl chloride (0.58 ml,) and THF (50 mL) was added 1,8-diazabicyclo[5.4.0]undec-7-ene (1.65 ml,), and the mixture was stirred at room temperature for 2 hr. Water was added to the reaction solution, and the mixture was extracted with ethyl acetate. The extract was washed with water and saturated brine, and dried over magnesium sulfate, and the solvent was evaporated under reduced pressure. To a solution (30 mL) of the residue in DMF was added sodium hydride (60% in oil, 0.4 g) at room temperature, and the mixture was stirred for 30 min. To the reaction mixture was added saturated aqueous ammonium chloride solution, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 5→20% ethyl acetate/hexane) to give the title compound (1.17 g, 67%) as a colorless oil.

$^1$H-NMR (CDCl$_3$): δ1.37 (3H, d, J=5.7 Hz), 1.43 (9H, s), 3.21-3.56 (1H, m), 3.85-4.42 (3H, m), 4.57-4.77 (1H, m), 6.95 (1H, s). ESI-MS: m/z 250(M-Boc+H)$^+$.

(step 5) tert-butyl (2S)-8-(3-fluorophenyl)-2-methyl-2,3-dihydrothieno[2,3-f][1,4] oxazepine-4(5H)-carboxylate A mixed solution of tert-butyl (2S)-8-bromo-2-methyl-2,3-dihydrothieno[2,3-f][1,4]oxazepine-4(5H)-carboxylate (434 mg), (3-fluorophenyl)boronic acid (227 mg), dichlorobis(triphenylphosphine)palladium (44 mg) and potassium carbonate (518 mg) in DME-water (1:1, 12 mL) was stirred at 85° C. for 2 hr under a nitrogen stream. The reaction solution was cooled to room temperature, water was added, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 5→15% ethyl acetate/hexane) to give the title compound (430 mg, 95%) as a colorless oil.

$^1$H-NMR (CDCl$_3$): δ1.33 (3H, d, J=6.0 Hz), 1.44 (9H, s), 3.19-3.49 (1H, m), 3.93-4.38 (3H, m), 4.64-4.86 (1H, m), 6.93-7.03 (1H, m), 7.07 (1H, s), 7.28-7.40 (3H, m).

(step 6) (2S)-8-(3-fluorophenyl)-2-methyl-2,3,4,5-tetrahydrothieno[2,3-f][1,4]oxazepine 1 hydrochloride tert-Butyl (2S)-8-(3-fluorophenyl)-2-methyl-2,3-dihydrothieno[2,3-f][1,4]oxazepine-4(5H)-carboxylate (416 mg) was stirred in 4N hydrogen chloride-ethyl acetate solution (5 mL) for 20 min. The reaction solution was concentrated under reduced pressure, and the residue was recrystallized from ethyl acetate to give (2S)-8-(3-fluorophenyl)-2-methyl-2,3,4,5-tetrahydrothieno[2,3-f][1,4]oxazepine 1 hydrochloride (315 mg, 92%) as colorless crystals.

$^1$H-NMR (DMSO-d$_6$): δ1.37 (3H, d, J=6.4 Hz), 3.24-3.44 (1H, m), 3.61 (1H, d, J=14.0 Hz), 4.24-4.60 (3H, m), 7.08-7.25 (1H, m), 7.39-7.55 (3H, m), 7.75 (1H, s), 9.78 (2H, brs). ESI-MS (free base): m/z 264 (M+H)$^+$.

Example 13

(2S)-8-(2-fluorophenyl)-2-methyl-2,3,4,5-tetrahydrothieno[2,3-f][1,4]oxazepine 1 hydrochloride

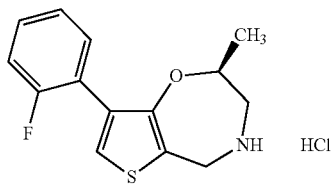 [SMILES: C[C@H]1CNCc2scc(-c3ccccc3F)c2O1 ; Cl]

(step 1) tert-butyl (2S)-8-(2-fluorophenyl)-2-methyl-2,3-dihydrothieno[2,3-f][1,4]oxazepine-4(5H)-carboxylate A mixed solution of tert-butyl (2S)-8-bromo-2-methyl-2,3-dihydrothieno[2,3-f][1,4]oxazepine-4(5H)-carboxylate (681 mg) obtained in Example 12, steps 1-4, (2-fluorophenyl)boronic acid (356 mg), dichlorobis(triphenylphosphine)palladium (68 mg) and potassium carbonate (809 mg) in DME-water (1:1, 20 mL) was stirred at 85° C. for 4 hr under a nitrogen stream. The reaction solution was cooled to room temperature, and water was added. The mixture was filtered through celite, and extracted with ethyl acetate. The extract was washed with water and saturated brine, and dried over magnesium sulfate, and the solvent was evaporated under reduced pressure. The residue was purified by silica gel column chromatography (solvent gradient; 5→15% ethyl acetate/hexane) to give the title compound (694 mg, 98%) as a colorless oil.

$^1$H-NMR (CDCl$_3$): δ1.27 (3H, d, J=6.0 Hz), 1.45 (9H, s), 3.11-3.41 (1H, m), 3.94-4.32 (3H, m), 4.67-4.92 (1H, m), 7.05-7.19 (3H, m), 7.24-7.33 (1H, m) 7.41-7.50 (1H, m). ESI-MS: m/z 264 (M-Boc+H)$^+$.

(step 2) (2S)-8-(2-fluorophenyl)-2-methyl-2,3,4,5-tetrahydrothieno[2,3-f][1,4]oxazepine 1 hydrochloride tert-Butyl (2S)-8-(2-fluorophenyl)-2-methyl-2,3-dihydrothieno[2,3-f][1,4]oxazepine-4(5H)-carboxylate (694 mg) was stirred in 4 N hydrogen chloride-ethyl acetate solution (7 mL) for 1.5 hr. The reaction solution was concentrated under reduced pressure, and the residue was recrystallized from ethyl acetate to give (2S)-8-(2-fluorophenyl)-2-methyl-2,3,4,5-tetrahydrothieno[2,3-f][1,4]oxazepine 1 hydrochloride (531 mg, 93%) as colorless crystals.

$^1$H-NMR (DMSO-d$_6$): δ1.27 (3H, d, J=6.4 Hz), 3.23-3.31 (1H, m), 3.60 (1H, d, J=14.0 Hz), 4.25-4.42 (2H, m), 4.54 (1H, d, J=15.2 Hz), 7.23-7.34 (2H, m), 7.37-7.48 (2H, m), 7.54 (1H, s), 9.70 (2H, brs). ESI-MS (free base): m/z 264 (M+H)$^+$.

Example 14

(2S)-8-cyclopropyl-2-methyl-2,3,4,5-tetrahydrothieno[2,3-f][1,4]oxazepine 1 hydrochloride

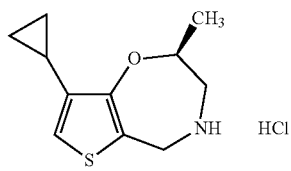

(step 1) tert-butyl (2S)-8-cyclopropyl-2-methyl-2,3-dihydrothieno[2,3-f][1,4]oxazepine-4(5H)-carboxylate A suspension of tert-butyl (2S)-8-bromo-2-methyl-2,3-dihydrothieno[2,3-f][1,4]oxazepine-4(5H)-carboxylate (616 mg) obtained in Example 12, steps 1-4, cyclopropylboronic acid (228 mg), palladium acetate (20 mg), tricyclohexylphosphine (50 mg), potassium tert-butoxide (595 mg) and toluene (20 ml) was stirred at 80° C. for 14 hr under an argon atmosphere. The reaction solution was cooled to room temperature, and filtered through celite. Water was added, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 0→10% ethyl acetate/hexane) to give the title compound (453 mg, 83%) as a colorless oil.

$^1$H-NMR (CDCl$_3$): δ0.53-0.72 (2H, m), 0.79-0.89 (2H, m), 1.34 (3H, d, J=6.8 Hz), 1.42 (9H, s), 1.74-1.85 (1H, m), 3.16-3.50 (1H, m), 3.87-4.36 (3H, m), 4.56-4.77 (1H, m), 6.36 (1H, s).

(step 2) (2S)-8-cyclopropyl-2-methyl-2,3,4,5-tetrahydrothieno[2,3-f][1,4]oxazepine 1 hydrochloride tert-Butyl (2S)-8-cyclopropyl-2-methyl-2,3-dihydrothieno[2,3-f][1,4]oxazepine-4(5H)-carboxylate (453 mg) was stirred in 4N hydrogen chloride-ethyl acetate solution (5 mL) for 20 min. The reaction solution was concentrated under reduced pressure, and the residue was recrystallized from ethyl acetate to give (2S)-8-cyclopropyl-2-methyl-2,3,4,5-tetrahydrothieno[2,3-f][1,4]oxazepine 1 hydrochloride (308 mg, 86%) as colorless crystals.

$^1$H-NMR (DMSO-d$_6$): δ0.49-0.75 (2H, m), 0.77-0.90 (2H, m), 1.37 (3H, d, J=6.4 Hz), 1.71-1.83 (1H, m), 3.20-3.29 (1H, m), 3.56 (1H, d, J=14.0 Hz), 4.15-4.53 (3H, m), 6.86 (1H, s), 9.66 (2H, brs).

ESI-MS (free base): m/z 210 (M+H)$^+$.

Example 15

(2S)-2-methyl-8-(1-methylethyl)-2,3,4,5-tetrahydrothieno[2,3-f][1,4]oxazepine 1 hydrochloride

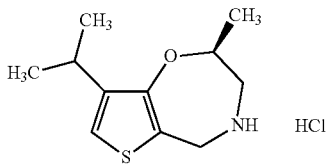

(step 1) tert-butyl (2S)-2-methyl-8-(1-methylethyl)-2,3-dihydrothieno[2,3-f][1,4]oxazepine-4(5H)-carboxylate A mixed solution of tert-butyl (2S)-8-bromo-2-methyl-2,3-dihydrothieno[2,3-f][1,4]oxazepine-4(5H)-carboxylate (1.15 g) obtained in Example 12, steps 1-4, isopropenylboronic acid pinacol ester (0.807 mL), dichlorobis(triphenylphosphine)palladium (116 mg) and potassium carbonate (1.37 g) in DME-water (1:1, 30 mL) was stirred at 85° C. for 2 hr under a nitrogen stream. The reaction solution was cooled to room temperature, water was added, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 5→12% ethyl acetate/hexane) to give a colorless oil. To a solution of the obtained oil in THF-MeOH (2:1, 30 mL) was added 10% palladium on carbon (100 mg), and the mixture was stirred for 1 hr under a hydrogen atmosphere. The reaction solution was filtered, and concentrated under reduced pressure. The residue was purified by silica gel column chromatography (solvent gradient; 0→10% ethyl acetate/hexane) to give the title compound (926 mg, 90%) as a colorless oil.

$^1$H-NMR (CDCl$_3$): δ1.15-1.24 (6H, m), 1.34 (3H, d, J=6.4 Hz), 1.43 (9H, s), 2.28-2.97 (1H, m), 3.11-3.44 (1H, m), 3.86-4.30 (3H, m), 4.58-4.84 (1H, m), 6.58 (1H, s).

(step 2) (2S)-2-methyl-8-(1-methylethyl)-2,3,4,5-tetrahydrothieno[2,3-f][1,4]oxazepine 1 hydrochloride tert-Butyl (2S)-2-methyl-8-(1-methylethyl)-2,3-dihydrothieno[2,3-f][1,4]oxazepine-4(5H)-carboxylate (261 mg) was stirred in 4N hydrogen chloride-ethyl acetate solution (5 ml) for 2 hr. The precipitated crystals were washed with ethyl acetate to give (2S)-2-methyl-8-(1-methylethyl)-2,3,4,5-tetrahydrothieno[2,3-f][1,4]oxazepine 1 hydrochloride (183 mg, 88%) as colorless crystals.

$^1$H-NMR (DMSO-d$_6$): δ1.16 (6H, dd, J=6.8, 0.6 Hz), 1.37 (3H, d, J=6.4 Hz), 2.75-2.91 (1H, m), 3.22-3.30 (1H, m), 3.57 (1H, d, J=13.9 Hz), 4.15-4.29 (2H, m), 4.36-4.48 (1H, m), 7.04 (1H, s), 9.63 (2H, brs).

ESI-MS (free base): m/z 212 (M+H)$^+$.
Elemental Analysis
Calculated (C$_{11}$H$_{17}$NOS.HCl): C, 53.32; H, 7.32; N, 5.65. Found: C, is 53.33; H, 7.21; N, 5.60.

Example 16

(2S)-2-methyl-8-propyl-2,3,4,5-tetrahydrothieno[2,3-f][1,4]oxazepine 1 hydrochloride

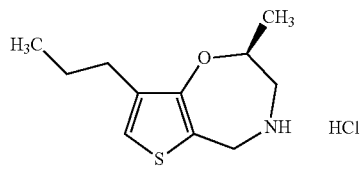

(step 1) tert-butyl (2S)-2-methyl-8-[(1Z)-prop-1-en-1-yl]-2,3-dihydrothieno[2,3-f][1,4]oxazepine-4(5H)-carboxylate A mixed solution of tert-butyl (2S)-8-bromo-2-methyl-2,3-dihydrothieno[2,3-f][1,4]oxazepine-4(5H)-carboxylate (599 mg) obtained in Example 12, steps 1-4, cis-propenylboronic acid (192 mg), dichlorobis(triphenylphosphine)palladium (60 mg) and potassium carbonate (713 mg) in DME-water (1:1, 20 mL) was stirred at 85° C. for 4 hr under a nitrogen stream. The reaction solution was cooled to room temperature, water was added, and the mixture was extracted with ethyl acetate. The extract was washed with water and saturated brine, and dried over magnesium sulfate, and the solvent was evaporated under reduced pressure. The residue was purified by silica gel column chromatography (solvent gradient; 5→15% ethyl acetate/hexane) to give the title compound (399 mg, 75%) as a colorless oil.

$^1$H-NMR (CDCl$_3$): δ1.28-1.39 (3H, m), 1.43 (9H, s), 1.79-1.97 (3H, m), 3.17-3.50 (1H, m), 3.87-4.38 (3H, m), 4.56-4.79 (1H, m), 5.72-5.86 (1H, m), 6.19-6.33 (1H, m), 6.90 (1H, s).

(step 2) tert-butyl (2S)-2-methyl-8-propyl-2,3-dihydrothieno[2,3-f][1,4]oxazepine-4(5H)-carboxylate To a solution of tert-butyl (2S)-2-methyl-8-[(1Z)-prop-1-en-1-yl]-2,3-dihydrothieno[2,3-f][1,4]oxazepine-4(5H)-carboxylate (390 mg) in THF-MeOH (2:1, 15 ml) was added 10% palladium on carbon (50 mg), and the mixture was stirred for 1 hr under a hydrogen atmosphere. The reaction solution was filtered, and concentrated under reduced pressure. The residue was purified by silica gel column chromatography (solvent gradient; 0→15% ethyl acetate/hexane) to give the title compound (366 mg, 93%) as a colorless oil.

$^1$H-NMR (CDCl$_3$): δ0.93 (3H, t, J=7.4 Hz), 1.33 (3H, d, J=6.4 Hz), 1.42 (9H, s), 1.50-1.65 (2H, m), 2.33-2.48 (2H, m), 3.15-3.46 (1H, m), 3.87-4.33 (3H, m), 4.57-4.81 (1H, m), 6.58 (1H, s).

(step 3) (2S)-2-methyl-8-propyl-2,3,4,5-tetrahydrothieno[2,3-f][1,4]oxazepine 1 hydrochloride tert-Butyl (2S)-2-methyl-8-propyl-2,3-dihydrothieno[2,3-f][1,4]oxazepine-4(5H)-carboxylate (365 mg) was stirred in 4 N hydrogen chloride-ethyl acetate solution (5 ml) for 20 min. The reaction solution was concentrated under reduced pressure, and the residue was recrystallized from ethyl acetate to give (2S)-2-methyl-8-propyl-2,3,4,5-tetrahydrothieno[2,3-f][1,4]oxazepine 1 hydrochloride (250 mg, 86%) as colorless crystals.

$^1$H-NMR (DMSO-d$_6$): δ0.89 (3H, t, J=7.4 Hz), 1.35 (3H, d, J=6.8 Hz), 1.43-1.61 (2H, m), 2.38 (2H, t, J=7.4 Hz), 3.21-3.29 (1H, m), 3.56 (1H, d, J=14.0 Hz), 4.13-4.29 (2H, m), 4.35-4.51 (1H, m), 7.05 (1H, s), 9.60 (2H, brs).

ESI-MS (free base): m/z 212 (M+H)$^+$.

Example 17

8-cyclopropyl-7-methyl-2,3,4,5-tetrahydrothieno[2,3-f][1,4]oxazepine 1 hydrochloride

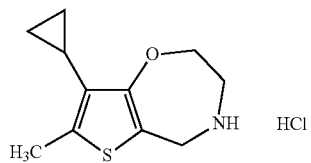

(step 1) tert-butyl 7-bromo-8-cyclopropyl-2,3-dihydrothieno[2,3-f][1,4]oxazepine-4(5H)-carboxylate A solution of tert-butyl 8-cyclopropyl-2,3-dihydrothieno[2,3-f][1,4]oxazepine-4(5H)-carboxylate (375 mg) obtained in Example 3, step 1, N-bromosuccinimide (237 mg) and acetonitrile (3 ml) was stirred at room temperature for 2 hr, 10% aqueous sodium thiosulfate solution was added, and the mixture was extracted with ethyl acetate. The extract was dried over anhydrous magnesium sulfate, and the solvent was evaporated under reduced pressure. The residue was purified by silica gel column chromatography (solvent gradient; 2→10% ethyl acetate/hexane) to give the title compound (359 mg, 75%) as an oil.

$^1$H-NMR (CDCl$_3$): δ0.78-0.86 (2H, m), 0.95-1.03 (2H, m), 1.43 (9H, s), 1.69-1.79 (1H, m), 3.74-3.80 (2H, m), 3.93-4.03 (2H, m), 4.30-4.42 (2H, m).

ESI-MS: m/z 318 (M-C$_4$H$_8$+H)$^+$.

(step 2) tert-butyl 8-cyclopropyl-7-methyl-2,3-dihydrothieno[2,3-f][1,4]oxazepine-4(5H)-carboxylate A solution of tert-butyl 7-bromo-8-cyclopropyl-2,3-dihydrothieno[2,3-f][1,4]oxazepine-4(5H)-carboxylate (264 mg), methylboronic acid (169 mg), potassium phosphate (600 mg), tetrakis(triphenylphosphine)palladium (81.7 mg) and DME (3 mL) was stirred at 80° C. for 20 hr, the reaction mixture was poured into water, and the mixture was extracted with ethyl acetate. The extract was dried over anhydrous magnesium sulfate, and the solvent was evaporated under reduced pressure. The residue was purified by silica gel column chromatography (solvent gradient; 2→10% ethyl acetate/hexane) to give the title compound (166 mg, 76%) as an oil.

$^1$H-NMR (CDCl$_3$): δ0.70-0.81 (4H, m), 1.43 (9H, s), 1.50-1.60 (1H, m), 2.34 (3H, s), 3.74-3.81 (2H, m), 4.00 (2H, brs), 4.31-4.51 (2H, m).

ESI-MS: m/z 254 (M-C$_4$H$_8$+H)$^+$.

(step 3) 8-cyclopropyl-7-methyl-2,3,4,5-tetrahydrothieno[2,3-f][1,4]oxazepine 1 hydrochloride To tert-butyl 8-cyclopropyl-7-methyl-2,3-dihydrothieno[2,3-f][1,4]oxazepine-4(5H)-carboxylate (166 mg) was added 4N hydrogen chloride-ethyl acetate solution (3 mL), the mixture was stirred at room temperature for 1 hr, and the solvent was evaporated under reduced pressure. The residue was recrystallized from a mixed solvent of MeOH, EtOH and Et$_2$O to give 8-cyclopropyl-7-methyl-2,3,4,5-tetrahydrothieno[2,3-f][1,4]oxazepine 1 hydrochloride (94.0 mg, 71%) as a solid.

$^1$H-NMR (DMSO-d$_6$): δ0.67-0.74 (2H, m), 0.74-0.83 (2H, m), 1.53-1.65 (1H, m), 2.32 (3H, s), 3.43-3.52 (2H, m), 4.13-4.19 (2H, m), 4.24 (2H, s), 9.50 (2H, brs).

ESI-MS (free base): m/z 210 (M+H)$^+$.

Elemental Analysis

Calculated (C$_{11}$H$_{15}$NOS.HCl): C, 53.76; H, 6.56; N, 5.70. Found: C, 53.56; H, 6.48; N, 5.72.

Example 18

2,7-dimethyl-8-(1-methylethyl)-2,3,4,5-tetrahydrothieno[2,3-f][1,4]oxazepine 1 hydrochloride

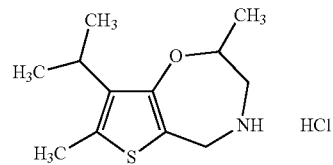

(step 1) tert-butyl 7-bromo-2-methyl-8-(1-methylethyl)-2,3-dihydrothieno[2,3-f][1,4]oxazepine-4(5H)-carboxylate A solution of tert-butyl 2-methyl-8-(1-methylethyl)-2,3-dihydrothieno[2,3-f][1,4]oxazepine-4(5H)-carboxylate (763 mg) obtained in Example 10, steps 1 and 2, N-bromosuccinimide (458 mg) and acetonitrile (6 mL) was stirred at room temperature for 2 hr, 10% aqueous sodium thiosulfate solution was added, and the mixture was extracted with ethyl acetate. The extract was washed with saturated brine, and dried over anhydrous magnesium sulfate, and the solvent was evaporated under reduced pressure. The residue was purified by silica gel column chromatography (solvent gradient; 3→7% ethyl acetate/hexane) to give the title compound (797 mg, 83%) as an oil.

$^1$H-NMR (CDCl$_3$): δ1.23 (3H, d, J=2.7 Hz), 1.26 (3H, d, J=2.7 Hz), 1.35 (3H, d, J=6.4 Hz), 1.43 (9H, s), 2.99-3.36 (2H, m), 3.83-4.23 (3H, m), 4.46-4.78 (1H, m).

ESI-MS: m/z 290 (M-Boc+H)$^+$.

(step 2) tert-butyl 2,7-dimethyl-8-(1-methylethyl)-2, 3-dihydrothieno[2,3-f][1,4]oxazepine-4(5H)-carboxylate A solution of tert-butyl 7-bromo-2-methyl-8-(1-methylethyl)-2,3-dihydrothieno[2,3-f][1,4]oxazepine-4(5H)-carboxylate (390 mg), methylboronic acid (239 mg), potassium phosphate (849 mg), tetrakis(triphenylphosphine)palladium (116 mg) and DME (4 mL) was stirred at 80° C. for 20 hr, the reaction mixture was poured into water, and the mixture was extracted with ethyl acetate. The extract was washed with saturated brine, and dried over anhydrous magnesium sulfate, and the solvent was evaporated under reduced pressure. The residue was purified by silica gel column chromatography (solvent gradient; 3→7% ethyl acetate/hexane) to give the title compound (266 mg, 82%) as a solid.

$^1$H-NMR (CDCl$_3$): δ1.22 (3H, d, J=3.5 Hz), 1.25 (3H, d, J=3.5 Hz), 1.35 (3H, d, J=6.4 Hz), 1.44 (9H, s), 2.28 (3H, s), 2.88-3.03 (1H, m), 3.04-3.19 (1H, m), 3.84-4.01 (1H, m), 4.04-4.23 (2H, m), 4.50-4.66 (1H, m).

ESI-MS: m/z 226 (M-Boc+H)$^+$.

(step 3) 2,7-dimethyl-8-(1-methylethyl)-2,3,4,5-tetrahydrothieno[2,3-f][1,4]oxazepine 1 hydrochloride To tert-butyl 2,7-dimethyl-8-(1-methylethyl)-2,3-dihydrothieno[2,3-f][1,4]oxazepine-4(5H)-carboxylate (266 mg) was added 4 N hydrogen chloride-ethyl acetate solution (2 ml), the mixture was stirred at room temperature for 1.5 hr, and the solvent was evaporated under reduced pressure. The residue was washed with ethyl acetate to give 2,7-dimethyl-8-(1-methylethyl)-2,3,4,5-tetrahydrothieno[2,3-f][1,4]oxazepine 1 hydrochloride (182 mg, 85%) as a solid.

$^1$H-NMR (DMSO-d$_5$): δ1.18 (6H, d, J=7.0 Hz), 1.36 (3H, d, J=6.4 Hz), 2.26 (3H, s), 2.87-3.06 (1H, m), 3.17-3.29 (1H, m), 3.53 (1H, d, J=13.8 Hz), 4.05-4.20 (2H, m), 4.27 (1H, s), 9.52 (1H, brs).

ESI-MS (free base): m/z 226 (M+H)$^+$.

Example 19

(2S)-2,7-dimethyl-8-(1-methylethyl)-2,3-dihydrothieno[2,3-f][1,4]oxazepine 1 hydrochloride

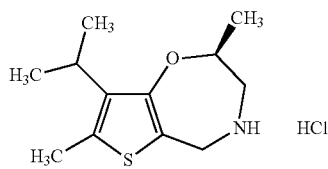

(step 1) tert-butyl (2S)-7-bromo-2-methyl-8-(1-methylethyl)-2,3-dihydrothieno[2,3-f][1,4]oxazepine-4 (5H)-carboxylate A solution of tert-butyl (2S)-2-methyl-8-(1-methylethyl)-2,3-dihydrothieno[2,3-f][1,4]oxazepine-4(5H)-carboxylate (839 mg) obtained in Example 15, step 1, N-bromosuccinimide (503 mg) and acetonitrile (10 mL) was stirred at room temperature for 1.5 hr, 10% aqueous sodium thiosulfate solution was added, and the mixture was extracted with ethyl acetate. The extract was washed with saturated brine, and dried over anhydrous magnesium sulfate, and the solvent was evaporated under reduced pressure. The residue was purified by silica gel column chromatography (solvent gradient; 3→7% ethyl acetate/hexane) to give the title compound (908 mg, 86%) as a solid.

$^1$H-NMR (CDCl$_3$): δ1.24 (3H, d, J=2.6 Hz), 1.26 (3H, d, J=2.6 Hz), 1.36 (3H, d, J=6.4 Hz), 1.44 (9H, s), 2.99-3.35 (2H, m), 3.84-4.21 (3H, m), 4.46-4.78 (1H, m).

ESI-MS: m/z 290 (M-Boc+H)$^+$.

(step 2) tert-butyl (2S)-2,7-dimethyl-8-(1-methylethyl)-2,3-dihydrothieno[2,3-f][1,4]oxazepine-4 (5H)-carboxylate A solution of tert-butyl (2S)-7-bromo-2-methyl-8-(1-methylethyl)-2,3-dihydrothieno[2,3-f][1,4]oxazepine-4(5H)-carboxylate (400 mg), methylboronic acid (245 mg), potassium phosphate (870 mg), tetrakis(triphenylphosphine) palladium (118 mg) and DME (6 mL) was stirred at 80° C. for 16 hr, the reaction mixture was poured into water, and the mixture was extracted with ethyl acetate. The extract was washed with saturated brine, and dried over anhydrous magnesium sulfate, and the solvent was evaporated under reduced pressure. The residue was purified by silica gel column chromatography (solvent gradient; 3→7% ethyl acetate/hexane) to give the title compound (310 mg, 93%) as a solid.

$^1$H-NMR (CDCl$_3$): δ1.13-1.29 (6H, m), 1.34 (3H, d, J=6.6 Hz), 1.43 (9H, s), 2.27 (3H, s), 2.86-3.02 (1H, m), 3.04-3.36 (1H, m). 3.80-4.24 (3H, m), 4.48-4.78 (1H, m).

ESI-MS: m/z 226 (M-Boc+H)$^+$.

(step 3) (2S)-2,7-dimethyl-8-(1-methylethyl)-2,3-dihydrothieno[2,3-f][1,4]oxazepine 1 hydrochloride To tert-butyl (2S)-2,7-dimethyl-8-(1-methylethyl)-2,3-dihydrothieno[2,3-f][1,4]oxazepine-4(5H)-carboxylate (310 mg) was added 4 N hydrogen chloride-ethyl acetate solution (3 mL), the mixture was stirred at room temperature for 1 hr, and the solvent was evaporated under reduced pressure. The residue was washed with ethyl acetate to give (2S)-2,7-dimethyl-8-(1-methylethyl)-2,3-dihydrothieno[2,3-f][1,4]oxazepine 1 hydrochloride (228 mg, 91%) as a solid.

$^1$H-NMR (DMSO-d$_6$): δ1.19 (6H, d, J=6.0 Hz), 1.37 (3H, d, J=6.4 Hz), 2.27 (3H, s), 2.88-3.07 (1H, m), 3.24 (1H, dd, J=14.3, 9.8 Hz), 3.54 (1H, d, J=14.3 Hz), 4.07-4.23 (2H, m), 4.24-4.40 (1H, m), 9.46 (2H, brs).

ESI-MS (free base): m/z 226 (M+H)$^+$.

Example 20

8-(2,2,2-trifluoro-1-methylethyl)-2,3,4,5-tetrahydrothieno[2,3-f][1,4]oxazepine 1 hydrochloride

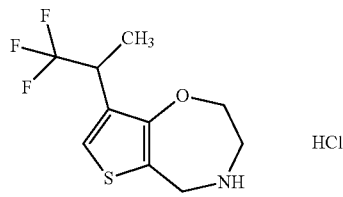 [SMILES: CC(c1csc2c1OCCNC2)C(F)(F)F ; Cl]

(step 1) tert-butyl 8-(4,4,5,5-tetramethyl-1,3,2-dioxaborolan-2-yl)-2,3-dihydrothieno[2,3-f][1,4]oxazepine-4(5H)-carboxylate A mixture of tert-butyl 8-bromo-2,3-dihydrothieno[2,3-f][1,4]oxazepine-4(5H)-carboxylate (1.00 g) obtained in Example 1, steps 1-3, bis(pinacolato)diborane (1.52 g), [1,1'-bis(diphenylphosphino)ferrocene]palladium(II) dichloride-dichloromethane complex (1:1) (123 mg), potassium acetate (883 mg) and dimethoxyethane (10 mL) was stirred at 90° C. for 12 hr under a nitrogen atmosphere. The reaction mixture was poured into water, and the mixture was extracted with ethyl acetate. The extract was washed with water, and dried over anhydrous magnesium sulfate, and the solvent was evaporated under reduced pressure. The residue was purified by silica gel column chromatography (hexane:ethyl acetate=4:1) to give the title compound (1.03 g, 90.4%) as an oil.

$^1$H-NMR (CDCl$_3$): δ1.62 (6H, s), 1.32 (9H, s), 1.42 (6H, s), 3.80-3.83 (2H, m), 4.10-4.15 (2H, m), 4.45-4.55 (2H, m), 7.48 (1H, s).

(step 2) tert-butyl 8-[1-(trifluoromethyl)vinyl]-2,3-dihydrothieno[2,3-f][1,4]oxazepine-4(5H)-carboxylate A mixture of tert-butyl 8-(4,4,5,5-tetramethyl-1,3,2-dioxaborolan-2-yl)-2,3-dihydrothieno[2,3-f][1,4]oxazepine-4(5H)-carboxylate (300 mg), 2-bromo-3,3,3-trifluoropropene (0.2 ml), tetrakis(triphenylphosphine)palladium(0) (25.5 mg), saturated aqueous sodium carbonate solution (7 ml) and dimethoxyethane (10 ml) was stirred at 85° C. for 12 hr under an argon atmosphere. The reaction mixture was poured into water, and the mixture was extracted with ethyl acetate. The extract was washed with water, and dried over anhydrous magnesium sulfate, and the solvent was evaporated under reduced pressure. The residue was purified by silica gel column chromatography (hexane:ethyl acetate=9:1) to give the title compound (140 mg, 50.9%) as an oil.

$^1$H-NMR (CDCl$_3$): δ1.44 (9H, s), 3.83-3.86 (2H, m), 4.06-4.09 (2H, m), 4.47-4.55 (2H, m), 5.97 (1H, s), 6.06 (1H, s), 7.07 (1H, s).

(step 3) tert-butyl 8-(2,2,2-trifluoro-1-methylethyl)-2,3-dihydrothieno[2,3-f][1,4]oxazepine-4(5H)-carboxylate A mixture of tert-butyl 8-[1-(trifluoromethyl)vinyl]-2,3-dihydrothieno[2,3-f][1,4]oxazepine-4(5H)-carboxylate (140 mg), 10% palladium on carbon (50 mg) and ethanol (10 ml) was stirred for 12 hr under a hydrogen atmosphere. The reaction mixture was filtered, and the filtrate was concentrated under reduced pressure to give the title compound (140 mg, 99.3%) as an oil.

$^1$H-NMR (CDCl$_3$): δ1.40-1.43 (12H, m), 3.51-4.10 (5H, m), 4.39-4.58 (2H, m), 6.90 (1H, s).

(step 4) 8-(2,2,2-trifluoro-1-methylethyl)-2,3,4,5-tetrahydrothieno[2,3-f][1,4]oxazepine 1 hydrochloride tert-Butyl 8-(2,2,2-trifluoro-1-methylethyl)-2,3-dihydrothieno[2,3-f][1,4]oxazepine-4(5H)-carboxylate (140 mg) was dissolved in ethyl acetate (2 mL), 4 N hydrogen chloride-ethyl acetate solution (2 mL) was added, and the mixture was stirred at room temperature for 1 hr. The solvent was evaporated under reduced pressure, and the residue was recrystallized from a mixed solvent of methanol and ether to give the title compound (88.4 mg, 76.9%) as a solid.

$^1$H-NMR (DMSO-d$_6$): δ1.39 (3H, d, J=7.2 Hz), 3.54-3.57 (2H, m), 3.65-3.73 (1H, m), 4.19-4.25 (2H, m), 4.34-4.45 (2H, m), 7.49 (1H, s), 9.40 (2H, brs).

ESI-MS (free base): m/z 252 (M+H)$^+$.

Elemental Analysis

Calculated (C$_{10}$H$_{12}$NOSF$_3$.HCl): C, 41.74; H, 4.55; N, 4.87. Found: C, 41.65; H, 4.60; N, 4.96.

Example 21

(2S)-2-methyl-8-(2,2,2-trifluoro-1-methylethyl)-2,3,4,5-tetrahydrothieno[2,3-f][1,4]oxazepine 1 hydrochloride

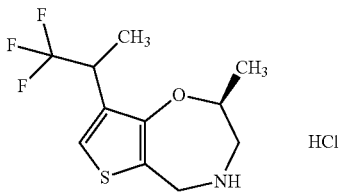 [SMILES: CC(c1csc2c1O[C@@H](C)CNC2)C(F)(F)F ; Cl]

(step 1) tert-butyl (2S)-2-methyl-8-(2,2,2-trifluoro-1-methylethyl)-2,3-dihydrothieno[2,3-f][1,4]oxazepine-4(5H)-carboxylate A solution of tert-butyl (2S)-8-bromo-2-methyl-2,3-dihydrothieno[2,3-f][1,4]oxazepine-4(5H)-carboxylate (697 mg) obtained in Example 12, steps 1-4, bis(pinacolato)diborane (559 mg), bis(dibenzylideneacetone)palladium (35 mg), tricyclohexylphosphine (40 mg), potassium acetate (294 mg) and 1,2-dimethoxyethane (20 mL) was stirred at 80° C. for 15 hr under an argon atmosphere. The reaction mixture was cooled to room temperature, filtered through celite, and extracted with ethyl acetate. The organic layer was washed with saturated brine, dried over magnesium sulfate, and concentrated. To a mixed solution (1:1, 20 mL) of the obtained residue in 1,2-dimethoxyethane-water were added 2-bromo-3,3,3-trifluoroprop-1-ene (0.25 mL), dichlorobis(triphenylphosphine)palladium (70 mg) and potassium carbonate (829 mg), and the mixture was stirred at 80° C. for 4 hr under an argon atmosphere. The reaction solution was cooled to room temperature, water was added, and the mixture was extracted with ethyl acetate. The organic layer was washed with water and saturated brine, dried over magnesium sulfate, and concentrated. The residue was purified by silica gel column chromatography (solvent gradient; 0→15% ethyl acetate/hexane) to give a pale-yellow oil. To a solution (10 mL) of the obtained oil in methanol was added 10% palladium on carbon (50 mg), and the mixture was stirred for 2 hr under a hydrogen atmosphere. The reaction solution was filtered, and the filtrate was concentrated. The residue was purified by high performance liquid chromatography to give the title compound (220 mg, 30%) as a colorless oil.

$^1$H-NMR (CDCl$_3$): δ1.29-1.36 (3H, m), 1.38-1.47 (12H, m), 3.12-3.35 (1H, m), 3.48-3.67 (1H, m), 3.88-4.36 (3H, m), 4.60-4.82 (1H, m), 6.90 (1H, s).

ESI-MS: m/z 309 (M-C$_4$H$_8$+H)$^+$.

(step 2) (2S)-2-methyl-8-(2,2,2-trifluoro-1-methyl-ethyl)-2,3,4,5-tetrahydrothieno[2,3-f][1,4]oxazepine 1 hydrochloride tert-Butyl (2S)-2-methyl-8-(2,2,2-trifluoro-1-methyl-ethyl)-2,3-dihydrothieno[2,3-f][1,4]oxazepine-4(5H)-carboxylate (475 mg) was stirred in 4 N hydrogen chloride-ethyl acetate solution (10 mL) for 15 min. The reaction solution was concentrated, and the residue was recrystallized from diethyl ether to give the title compound (365 mg, 93%) as colorless crystals.

$^1$H-NMR (DMSO-d$_6$): δ1.32-1.45 (6H, m), 3.23-3.41 (1H, m), 3.51-3.82 (2H, m), 4.10-4.34 (2H, m), 4.42-4.55 (1H, m), 7.40-7.56 (1H, m) 9.51 (2H, brs).

ESI-MS (free base): m/z 266 (M+H)$^+$.

Formulation Examples

Formulation Example 1

| (1) The compound of Example 1 | 10 mg |
| (2) Lactose | 60 mg |
| (3) Cornstarch | 35 mg |
| (4) Hydroxypropylmethylcellulose | 3 mg |
| (5) Magnesium stearate | 2 mg |

A mixture of 10 mg of the compound obtained in Example 1, 60 mg of lactose and 35 mg of corn starch is granulated using 0.03 ml of an aqueous solution of 10 wt % hydroxypropylmethylcellulose (3 mg as hydroxypropylmethylcellulose), and then dried at 40° C. and sieved. The obtained granules are mixed with 2 mg of magnesium stearate, and the mixture is compressed. The obtained uncoated tablets are sugar-coated with an aqueous suspension of sucrose, titanium dioxide, talc and gum arabic. The thus-coated tablets are glazed with beeswax to give finally-coated tablets.

Formulation Example 2

| (1) The compound of Example 1 | 10 mg |
| (2) Lactose | 70 mg |
| (3) Cornstarch | 50 mg |
| (4) Soluble starch | 7 mg |
| (5) Magnesium stearate | 3 mg |

The compound (10 mg) obtained in Example 1 and 3 mg of magnesium stearate are granulated with 0.07 mL of an aqueous solution of soluble starch (7 mg as soluble starch), dried, and mixed with 70 mg of lactose and 50 mg of corn starch. The mixture is compressed to give tablets.

Reference Formulation Example 1

| (1) Rofecoxib | 5.0 mg |
| (2) Sodium chloride | 20.0 mg |
| (3) Distilled water | amount to make total volume 2.0 mL |

Rofecoxib (5.0 mg) and 20.0 mg of Sodium chloride are dissolved in distilled water, and water is added to make the total volume 2.0 mL. The solution is filtered, and filled into 2 ml of ampoule under sterile condition. The ampoule is sterilized, and then sealed to give a solution for injection.

Reference Formulation Example 2

| (1) Rofecoxib | 50 mg |
| (2) Lactose | 34 mg |
| (3) Cornstarch | 10.6 mg |
| (4) Cornstarch (paste) | 5 mg |
| (5) Magnesium stearate | 0.4 mg |
| (6) Calcium carboxymethylcellulose | 20 mg |
| total | 120 mg |

The above-mentioned (1) to (6) are mixed according to a conventional method and the mixture is tableted by a tableting machine to give a tablet.

Formulation Example 3

The formulation prepared in Formulation Example 1 or 2, and the formulation prepared in Reference Formulation Example 1 or 2 are combined.

Experimental Example 1

The serotonin 5-HT$_{2C}$ receptor agonist activity of the compound of the present invention was evaluated based on the changes in the intracellular calcium concentration by the following method. After transcription, 5-HT$_{2C}$ undergoes RNA editing of the second intracellular loop, which results in the change of three amino acids and 14 receptor isoforms. 5-HT$_{2C}$ stably expressing CHO cell that expresses isoform type VSV stably was purchased from Euroscreen S.A., and cultured in UltraCHO (BioWhittaker) medium containing 1% dialyzed bovine serum and 400 μg/mL G418. The cells were plated in a 384-well black clear bottom plate (PE Biosystems) at 5000 cells/well, and cultured for 24 hr in a CO$_2$ incubator, and changes in the intracellular calcium concentration mediated by the 5-HT$_{2C}$ receptor were evaluated using Calcium Kit-Fluo 3 (Dojindo Laboratories). A calcium kit buffer containing 2.5 mM probenecid, 0.04% Pluronic F-127 and 2.5 μg Fluo-3 AM (calcium indicator fluorescent dye) was prepared and used as a Fluo-3 loading solution (contained in Dojindo Laboratories Calcium Kit). The loading solution was incubated at 37° C., the medium in the wells of the cell culture plate was removed, and the loading solution was added to each well by 40 μL. The cells were reacted at 37° C. for 1 hr to allow uptake of Fluo-3 AM into the cells and washed.

The compound of the present invention was diluted with a calcium kit buffer, and dispensed to each well of the 384-well plate (REMP) by 40 μL to give a test compound plate. The cell culture plate and test compound plate were set on a Fluometric Imaging Plate Reader (FLIPR, Molecular Devices), and changes in the intracellular calcium concentration were measured. An increase in the fluorescence intensity of Fluo-3 matches with an increase in the intracellular calcium concentration mediated by a receptor. The changes in the intracellular fluorescence intensity were measured every second with a CCD camera of FLIPR and, after measurement for 5 seconds before addition of the compound, a diluted solution of the compound of the present invention was added by 20 μL to each well of the cell culture plate using an automatic dispenser in FLIPR.

The agonist activity was evaluated based on the difference in the fluorescence level obtained by subtracting the fluorescence intensity before addition of the compound from the maximum fluorescence intensity after the addition thereof. The results are shown in Table 1. The activity of the test compound is shown by the ratio (%) relative to the maximum response by 5-HT.

TABLE 1

| Ex. No. of test compound | ratio to maximum response by 5-HT (1 μM) |
|---|---|
| 2 | 101 |
| 3 | 98 |
| 4 | 99 |
| 5 | 107 |
| 6 | 97 |
| 12 | 101 |
| 14 | 100 |
| 15 | 96 |
| 16 | 97 |
| 17 | 91 |
| 20 | 85 |
| 21 | 94 |

Experimental Example 2

The oral absorbability of the compound of the present invention can be evaluated by measuring the bioavailability in oral administration as shown below.

The compound of the present invention is intravenously and orally administered to IGS rat, the plasma concentration is measured over time using a liquid chromatography-tandem type mass spectrometer (LC/MS/MS) as an analyzer, and the bioavailability in oral administration is calculated from the ratio of each area under the (blood concentration-time) curve.

Experimental Example 3

The phototoxicity of the compound of the present invention is evaluated by measuring the survival rate of the cells between light irradiation and non-irradiation according to the method shown below or the method described in OECD Guideline for testing of chemicals: 432 in vitro 3T3 NRU phototoxicity test (Apr. 13, 2004), or a method analogous thereto.

Mouse fetus-derived cell line BALB/3T3 clone A31 is seeded in a 10% calf serum-containing DMEM (Dulbecco's Modified Eagle Medium) in a 384 well plate at $2.5 \times 10^3$ cell/well, and cultivated in a 5% $CO_2$ incubator at 37° C. for 1 day. The culture medium is removed, and the compound of the present invention diluted with EBSS (Earle's Balanced Salt Solution) added with 10 mM HEPES (4-(2-hydroxyethyl)-1-piperazineethanesulfonic acid) buffer is added. After culture in a 5% $CO_2$ incubator at 37° C. for 1 hr, and a light irradiation treatment is applied by using a solar light irradiation apparatus (SXL-2500V2 type, Seric). As a control, an irradiation non-treatment group is prepared. The compound is removed, 10% calf serum-containing DMEM medium is added, and the cell is cultivated in a 5% $CO_2$ incubator at 37° C. for 1 day. The intracellular ATP content is quantified by ATPLite™-M (PerkinErmer), and the survival rates of the non-irradiation group and the irradiation group are compared.

Experimental Example 4

The phototoxicity of the compound of the present invention is measured by evaluating the presence or absence of a skin response on light irradiation by the method shown below or the methods shown in the cited documents based on U.S. Dept of Health and Human Services Food and Drug Administration, (CDER). Guidance for Industry: photosafety testing; May 2003. Rockville (MD); for example, (1) Forbes, P. D., Urbach, F. and Davies, R. E. (1977). Phototoxicity Testing of Fragrance Raw Materials. Fd. Cosmet. Toxicol., Vol. 15, pp. 55-60, (2) Sambuco, C. P. and Forbes, P. D. (1984). Quantitative Assessment of Phototoxicity in the Skin of Hairless Mice. Fd. Chem. Toxic., Vol. 22, no. 3, pp. 233-236 etc.

An administration solution obtained by suspending the compound of the present invention in a methylcellulose solution with 2000 mg/kg as the maximum dose is orally administered to female hairless mice (Hos: HR-1, about 8-week-old, body weight 10-30 g). After the administration, the mice are anesthetized by intraperitoneal administration of an aqueous chloral hydrate solution (60 mg/ml, about 0.15 mL/mouse). The mice are fixed in the prone position and the whole body is covered with an aluminum foil with a hole with diameter of about 1.3 cm. UV corresponding to 0.5 MED (minimal erythema dose), which is generated by a solar light irradiation system (SXL-5009V1 type, Seric), is irradiated through the 1.3 cm diameter hole to the center of the back for 0.5 hr, in synchronization with Tmax of the compound of the present invention. The presence or absence of a skin response on the irradiation site of the mice is observed for 3 days after the irradiation, based on which the phototoxicity of the compound of the present invention is determined. The skin response observation results of 0.5 w/v % methylcellulose solution oral administration group as a negative control and Lomefloxacin 1 hydrochloride 100 mg/kg oral administration group as a positive control are used for the determination.

Experimental Example 5

The effect of the compound of the present invention against stress urinary incontinence can be measured by comparison of the leak point pressure before and after compound administration, as shown below.

SD female rats (body weight 180-350 g) are anesthetized with urethane (Wako Pure Chemical Industries, Ltd.), and the spinal cord is cut at T8-9 level to eliminate the micturition reflex. During the operation, halothane (Takeda Pharmaceutical Company Limited) anesthesia is added as necessary. The rats are fixed at a dorsal position, and two catheters (PE-100; Clay Adams) are indwelled in the bladder. One of the catheters is filled with saline stained with Evans Blue dye (Merck), and connected to a 50 ml syringe (TERUMO CORPORATION) fixed on an infusion pump (KD Scientific) via a three-way cock. The other catheter is connected to a pressure transducer (DX-100; NIHON KOHDEN CORPORATION), and signals of the transducer are transmitted to computer via an amplifier (blood pressure amplification unit AP-641G; NIHON KOHDEN CORPORATION) and a data analyzer (BIOPAC; MP100), and recorded on a hard disk. The data is analyzed on the computer using a software (BIOPAC; Acq-Knowledge). Saline is injected into the bladder using the infusion pump at a rate of 360 ml/hr, infusion is stopped on the moment fluid leakage from the urethral meatus is observed, and the solution in the bladder is discharged by opening the three-way cock. The maximum intravesical pressure during infusion is taken as a leak point pressure, which is measured repeatedly until the value is stabilized, and the average value of the last three measures is taken as the data. The compound of the present invention is dissolved in DMA/PEG400 (1:1), the solution is intravenously administered at 0.5 ml/kg, and the leak point pressure is compared before and after the administration.

Experimental Example 6

The effect of the compound of the present invention against obesity can be measured by using the food consumption calculated as follows as an index.

Male F344 rats (CLEA Japan, Inc.) are received at 5 weeks of age, and reared by groups on a solid high-fat diet with lipid content 45 kcal % (D12451, ResearchDiets). When the rats reach sufficient obesity (40-60 weeks of age), they are individually fed on a powder high-fat diet with lipid content 45 kcal % (D12451M, ResearchDiets) in a food bottle. The rats are grouped using the body weight and food consumption (18:00-8:00) one day before administration as indices. The compound of the present invention is dissolved in 0.5% methylcellulose solution, and the solution is administered by gavage at a dose of 2 mL/kg at 18:00. A 0.5% methylcellulose solution is administered to a control group. After administration of the drug, a food bottle weighed in advance is placed in a breeding cage. The food bottle is weighed 3, 14 and 24 hr after administration, and the food consumption is calculated (Williams test or t-test).

Experimental Example 7

The effect of the compound of the present invention against organ prolapse can be measured by examining the enhancement of the urinary tract closing reaction of the pelvic floor muscles (iliococcygeal muscle, pubococcygeal muscle etc.), which is induced by the intravesical pressure increase, by the compound administration, as shown below.

SD female rats (body weight 200-310 g) are anesthetized with urethane (Wako Pure Chemical Industries, Ltd.), and the spinal cord is cut at T8-9 level to eliminate the micturition reflex. During the operation, halothane (Takeda Pharmaceutical Company Limited) anesthesia is added as necessary. The abdomen is opened, the bladder neck is ligated with a suture thread, and then, the hypogastric nerve and the pudendal nerve are bilaterally cut. A catheter (PE-90, Clay Adams) is inserted in the bladder, and the other end of the bladder catheter is connected to the pressure transducer and an aquatic reservoir (60 ml syringe) of saline via a three-way cock. A microchip transducer catheter (SPR-524, Millar Instruments Inc.) is inserted from the urethral orifice toward the bladder, and the transducer part is adjusted to be in the urethra at 10.0-15.0 mm from the urethral orifice using the scale on the catheter surface.

The topical changes in the urethral pressure (hereinafter to be referred to as urethral pressure for convenience) measured by the microchip transducer are input into a computer via an amplifier (blood pressure amplification unit AP-641G; NIHON KOHDEN CORPORATION) and a data analyzer (MP-100; biopack; sampled at 500 Hz), and recorded on a hard disk. The bladder pressure is rapidly increased to 50 cm $H_2O$ for 30 seconds by raising the position of the saline aquatic reservoir by 50 cm, and changes in the urethral pressure are observed. The response of the urethra induced by the increased bladder pressure is measured 3 times, and the average value of the last two measures is taken as the value before drug administration. The evaluation item is reflective urethral closure response, and the average urethral pressure per second is calculated by a smoothing treatment of the recorded value at 500 points. Then, the value immediately before bladder pressure increase is subtracted from the maximum value during bladder pressure increase and taken as the urethral closing responses. The value before drug administration is measured, the compound of the present invention is dissolved in N,N-dimethylformamide/polyethylene glycol 400 (1:1), the solution is intravenously administered at 0.5 mL/kg and, 10 min later, the urethral closure response is evaluated again.

INDUSTRIAL APPLICABILITY

Since the compound of the present invention has a superior serotonin 5-$HT_{2C}$ receptor activating action, they are useful as a drug for the prophylaxis or treatment of any serotonin 5-$HT_{2C}$-related diseases, for example, lower urinary tract symptom, obesity and/or organ prolapse.

This application is based on a patent application No. 2009-181360 filed in Japan, the contents of which are incorporated in full herein by this reference.

The invention claimed is:

1. A compound represented by the formula (I)

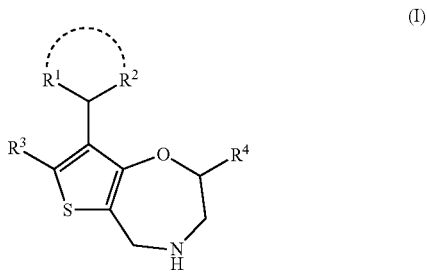

(I)

wherein
R$^1$ and R$^2$ are the same or different and each is a hydrogen atom, or a $C_{1-3}$ alkyl group optionally substituted by a halogen atom(s) (at least one of R$^1$ and R$^2$ is a $C_{1-3}$ alkyl group optionally substituted by halogen atom(s)), or
R$^1$ and R$^2$ form, together with the adjacent carbon atom, (a) a $C_{3-4}$ cycloalkyl group optionally substituted by halogen atom(s), (b) a phenyl group substituted by substituent(s) selected from a halogen atom and a $C_{1-3}$ alkoxy group, or (c) a furyl group; and
R$^3$ and R$^4$ are the same or different and each is a hydrogen atom or a $C_{1-3}$ alkyl group,
or a salt thereof.

2. The compound according to claim 1, wherein R$^1$ and R$^2$ are the same or different and each is a hydrogen atom, or a $C_{1-3}$ alkyl group optionally substituted by halogen atom(s) (at least one of R$^1$ and R$^2$ is a $C_{1-3}$ alkyl group optionally substituted by halogen atom(s)), or
R$^1$ and R$^2$ form, together with the adjacent carbon atom, a $C_{3-4}$ cycloalkyl group, or a phenyl group substituted by substituent(s) selected from a halogen atom and a $C_{1-3}$ alkoxy group; and $R^3$ and $R^4$ are the same or different and each is a hydrogen atom or a $C_{1-3}$ alkyl group, or a salt thereof.

3. The compound according to claim 1, wherein $R^1$ and $R^2$ are (1) both methyl groups optionally substituted by halogen atom(s), or (2) one is an ethyl group and the other is a hydrogen atom, or $R^1$ and $R^2$ form, together with the adjacent carbon atom, a cyclopropyl group, a cyclobutyl group, a 3-fluorophenyl group or a 3-methoxyphenyl group; and $R^3$ and $R^4$ are the same or different and each is a hydrogen atom or a methyl group, or a salt thereof.

4. The compound according to claim 1, wherein $R^1$ and $R^2$ are the same or different and each is a $C_{1-3}$ alkyl group optionally substituted by halogen atom(s), or $R^1$ and $R^2$ form, together with the adjacent carbon atom, a $C_{3-4}$ cycloalkyl group, or a phenyl group substituted by halogen atom(s); and $R^3$ and $R^4$ are the same or different and each is a hydrogen atom or a $C_{1-3}$ alkyl group, or a salt thereof.

5. The compound according to claim 1, wherein $R^1$ and $R^2$ are both methyl groups optionally substituted by halogen atom(s), or $R^1$ and $R^2$ form, together with the adjacent carbon atom, a cyclopropyl group, a cyclobutyl group or a 3-fluorophenyl group;

$R^3$ is a hydrogen atom; and $R^4$ is a hydrogen atom or a methyl group, or a salt thereof.

6. 8-(3-Fluorophenyl)-2,3,4,5-tetrahydrothieno[2,3-f][1,4]oxazepine or a salt thereof.

7. 8-Cyclopropyl-2,3,4,5-tetrahydrothieno[2,3-f][1,4]oxazepine or a salt thereof.

8. 8-(1-Methylethyl)-2,3,4,5-tetrahydrothieno[2,3-f][1,4]oxazepine or a salt thereof.

9. 8-Cyclobutyl-2,3,4,5-tetrahydrothieno[2,3-f][1,4]oxazepine or a salt thereof.

10. (2S)-8-(3-Fluorophenyl)-2-methyl-2,3,4,5-tetrahydrothieno[2,3-f][1,4]oxazepine or a salt thereof.

11. (2S)-2-Methyl-8-(1-methylethyl)-2,3,4,5-tetrahydrothieno[2,3-f][1,4]oxazepine or a salt thereof.

12. 8-(2,2,2-Trifluoro-1-methylethyl)-2,3,4,5-tetrahydrothieno[2,3-f][1,4]oxazepine or a salt thereof.

13. (2S)-2-Methyl-8-(2,2,2-trifluoro-1-methylethyl)-2,3,4,5-tetrahydrothieno[2,3-f][1,4]oxazepine or a salt thereof.

14. A pharmaceutical composition comprising the compound according to claim 1 or a salt thereof and a pharmacologically acceptable carrier.

15. A method for the treatment of a lower urinary tract symptom, obesity and/or organ prolapse in a mammal, comprising administering an effective amount of the compound according to claim 1 or a salt thereof to the mammal.

* * * * *